(12) United States Patent
Wendt et al.

(10) Patent No.: US 7,910,742 B2
(45) Date of Patent: Mar. 22, 2011

(54) SURVIVIN INHIBITORS

(75) Inventors: Michael D. Wendt, Vernon Hills, IL (US); Chaohong Sun, Gurnee, IL (US); Daryl R. Sauer, Trevor, WI (US); Steven W. Elmore, Northbrook, IL (US); Aaron R. Kunzer, Schaumburg, IL (US)

(73) Assignee: Abbott Laboratories, Abbott Park, IL (US)

( * ) Notice: Subject to any disclaimer, the term of this patent is extended or adjusted under 35 U.S.C. 154(b) by 1101 days.

(21) Appl. No.: 11/529,845

(22) Filed: Sep. 29, 2006

(65) Prior Publication Data

US 2007/0072833 A1    Mar. 29, 2007

Related U.S. Application Data

(60) Provisional application No. 60/721,634, filed on Sep. 29, 2005.

(51) Int. Cl.
*C07D 401/12* (2006.01)
(52) U.S. Cl. ........................................ 546/194
(58) Field of Classification Search .................. 546/194; 514/318
See application file for complete search history.

(56) References Cited

OTHER PUBLICATIONS

Balant et al., "Metabolic Considerations, etc.,"Burger's Medicinal Chemistry, 5th ed., 1, Wolff ed. NY: John Wiley & Sons, 1995, pp. 949-982.*

A. Burkle, et al., "Ageing and PARP", *Pharmacological Research*, 52: 93-99 (2005).
A. Chiarugi, et al., "Poly(ADP-ribosyl)ation and Stroke", *Pharmacological Research*, 52: 15-24 (2005).
S. Cuzzocrea, et al., "Role of Poly(ADP-ribose) Glycohydrolase (PARG) in Shock, Ischemia and Reperfusion", *Pharmacological Research*, 52: 100-108 (2005).
S. Cuzzocrea, et al., "Shock, Inflammation and PARP", *Pharmacological Research*, 52: 72-82 (2005).
K. Devalaraja-Narashimha, et al. "Poly(ADP-ribose) Polymerase-Medicated Cell Injury in Acute Renal Failure", *Pharmacological Research*, 52: 44-59 (2005).
G. Graziani, et al., "Clinical Perspectives of PARP Inhibitors", *Pharmacological Research*, 52: 109-118 (2005).
G. Graziani, et al., "PARP-1 Inhibition to Treat Cancer, Ischemia, Inflammation", *Pharmacological Research*, 52: 1-4 (2005).
D.W. Koh, et al. "Mediation of Cell Death by Poly (ADP-ribose) Polymerase-1", *Pharmacological Research*, 52: 5-14 (2005).
C. Szabo, et al., "Cardioprotective Effects of Poly(ADP-ribose) Polynerase Inhibition", *Pharmacological Research*, 52: 34-43 (2005).
C. Szabo, et al., "Roles of Poly(ADP-ribose) Polymerase Activiation in the Pathogenesis of Diabetes Mellitus and its Complications", *Pharmacological Research*, 52: 60-71 (2005).
L. Tentori, et al., "Chemopotentiation by PARP Inhibitors in Cancer Therapy", *Pharmacological Research*, 52: 25-33 (2005).
L. Virag, et al., "Poly(ADP-ribosyl)ation in Asthma and Other Lung Diseases", *Pharmacological Research*, 52: 25-33 (2005).

* cited by examiner

*Primary Examiner* — Patricia L Morris
(74) *Attorney, Agent, or Firm* — Oona Manzari

(57) ABSTRACT

Compounds that inhibit survivin, compositions containing the compounds and methods of treating diseases in which survivin is unregulated or overexpressed are disclosed.

1 Claim, No Drawings

SURVIVIN INHIBITORS

This application claims priority to U.S. Provisional Application Ser. No. 60/721,634, filed Sep. 29, 2005.

FIELD OF THE INVENTION

This invention pertains to compounds that bind to survivin, compositions containing the compounds and methods of treating diseases in which survivin is unregulated or overexpressed.

BACKGROUND OF THE INVENTION

Survivin is a member of the IAP (inhibitors of apoptosis) family of proteins (Ambrosini G. et al. *Nature Med.* 1997, 3, 917-21). Survivin, like other IAP family members, has been implicated in protection from apoptosis. In cell culture systems, survivin overexpression has been associated with inhibition of both the intrinsic and extrinsic cell death pathways. (Mahotka C. et al. *Cancer Res.* 1999, 59, 6097-6102; Tamm, I. et al. *Cancer Res.* 1998, 58, 5315-20; Altieri D., *Nat. Rev. Cancer* 2003, 3, 46-54). There is also experimental evidence that survivin is important in cell division. Survivin shows a clear cell-cycle-dependent expression at mitosis. Survivin has also been shown to exist in distinct subcellular pools (Fortugno et al, *J. Cell. Sci.* 2003, 115, 575-85), and a nuclear pool of survivin has been shown to have an essential role in mitotic spindle function and cell cleavage. Survivin is a member of the group of chromosomal passenger proteins including INCENP, Aurora B kinase and Borealin. These proteins have been grouped based on their subcellular localization patterns and on demonstrated binding in vitro and in vivo (Bolton M. A. et al. *Mol. Biol. Cell* 2002, 13, 3064-77; Wheatley S. P. et al. *Curr. Biol.* 2001, 11, 886-90; Uren A. G. et al. *Curr. Biol.* 2000, 10, 1319-28; Honda, R. et al. *Mol. Biol. Cell* 2003, 14, 3325-41; Adams R. R. et al. *Trends Cell Biol.* 2001, 11, 49-54). In particular, survivin has been shown to be important for localization of Aurora B kinase to the mitotic machinery (Chen J. et al. *J. Biol. Chem* 2003, 278, 486-90), and this complex is important in communicating lack of tension to microtubules (Lens, S. and Medema, R. H. *Cell Cycle* 2003, 2, 507-10; Beardmore V. A. et al. *J. Cell. Sci.* 2004, 117, 4033-42). The chromosomal passenger proteins associate with centromeres at metaphase, central spindle microtubules at anaphase, and remain located at the cytokinesis remains at end of telophase. Survivin is highly overexpressed in transformed cell lines but is undetectable in terminally differentiated adult tissues (Chiou S. K. et al. *Med. Sci. Monit.* 2003, 9, 125-9). Thus survivin is an attractive therapeutic target in cancer due to both its differential expression in tumors compared to normal tissues and its ability to promote tumor growth and survival by multiple pathways involving multiple mechanisms.

SUMMARY OF THE INVENTION

One embodiment of this invention, therefore, pertains to compounds and therapeutically acceptable salts, prodrugs or salts of prodrugs thereof, that bind to survivin, the compounds having formula (I)

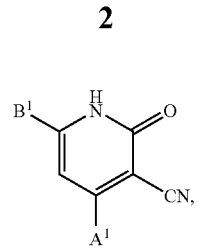

I wherein $A^1$ and $B^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NR^1C(O)NHR^1$, $NR^1C(O)N(R^1)_2$, $SO_2NHR^1$, $SO_2N(R^1)_2$, $NHSO_2R^1$ or $NHSO_2NHR^1$;

$R^1$ is $R^2$, $R^3$, $R^4$ or $R^5$;

$R^2$ is phenyl that is unfused or fused with benzene, heteroarene, cycloalkane or heterocycloalkane;

$R^3$ is heteroaryl that is unfused or fused with benzene, heteroarene, cycloalkane or heterocycloalkane;

$R^4$ is cycloalkyl, cycloalkenyl, heterocycloalkyl or heterocycloalkenyl, each of that is unfused or fused with benzene, heteroarene cycloalkane, cycloalkene, heterocycloalkane or heterocycloalkene;

$R^5$ is alkyl, alkenyl or alkynyl, each of which is unsubstituted or substituted with one or two or three of independently selected $R^6$, $R^7$, $OR^7$, $SR^7$, $S(O)R^7$, $SO_2R^7$, $NHR^7$, $N(R^7)_2$, $N(CH_3)(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NR^7SO_2R^7$, $NHC(O)OR^7$, $NR^7C(O)OR^7$, $SO_2NH_2$, $SO_2NHR^7$, $SO_2N(R^7)_2$, $NHC(O)NH_2$, $NHC(O)NHR^7$, $NHC(O)N(R^7)_2$, $NR^7C(O)N(R^7)_2$, $OH$, $(O)$, $C(O)OH$, $N_3$, $CN$, $NH_2$, $CF_3$, $CF_2CF_3$, $F$, $Cl$, $Br$ or $I$;

$R^6$ is spiroalkyl, spiroalkenyl, spiroheteroalkyl or spiroheteroalkenyl;

$R^7$ is $R^8$, $R^9$, $R^{10}$ or $R^{11}$;

$R^8$ is phenyl that is unfused or fused with benzene, heteroarene, cycloalkane, cycloalkene, heterocycloalkane or heterocycloalkene;

$R^9$ is heteroaryl that is unfused or fused with benzene, heteroarene, cycloalkane, cycloalkene, heterocycloalkane or heterocycloalkene;

$R^{10}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

wherein $R^2$, $R^3$, $R^4$, $R^8$, $R^9$ and $R^{10}$ are independently unsubstituted or substituted with one or two or three or four or five of independently selected $R^{20}$, $OR^{20}$, $SR^{20}$, $S(O)R^{20}$, $SO_2R^{20}$, $C(O)R^{20}$, $C(O)OR^{20}$, $CO(O)R^{20}$, $OC(O)R^{20}$, $OC(O)OR^{20}$, $NH_2$, $NHR^{20}$, $N(R^{20})_2$, $NHC(O)R^{20}$, $NR^{20}C(O)R^{20}$, $C(O)NH_2$, $C(O)NHR^{20}$, $C(O)N(R^{20})_2$, $C(O)NHOH$, $C(O)NHOR^{20}$, $SO_2NH_2$, $SO_2NHR^{20}$, $SO_2N(R^{20})_2$, $CF_3$, $CF_2CF_3$, $C(O)H$, $C(O)OH$, $C(N)NH_2$, $C(N)NHR^{20}$, $C(N)N(R^{20})_2$, $OH$, $(O)$, $N_3$, $CN$, $NO_2$, $CF_3$, $CF_2CF_3$, $OCF_3$, $OCF_2CF_3$, $F$, $Cl$, $Br$ or $I$;

$R^{20}$, is $R^{21}$, $R^{22}$, $R^{23}$ or $R^{24}$;

$R^{21}$ is phenyl that is unfused or fused with benzene, heteroarene, cycloalkane, cycloalkene, heterocycloalkane or heterocycloalkene;

$R^{22}$ is heteroaryl that is unfused or fused with benzene, heteroarene, cycloalkane, cycloalkene, heterocycloalkane or heterocycloalkene;

$R^{23}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{24}$ is alkyl, alkenyl or alkynyl, each of which is unsubstituted or substituted with one or two or three of independently selected $R^{25}$, $OR^{25}$, $SR^{25}$, $S(O)R^{25}$, $SO_2R^{25}$, $NH_2$, $NHR^{25}$, $N(R^{25})_2$, $C(O)R^{25}$, $C(O)OR^{25}$, $C(O)NH_2$, $C(O)NHR^{25}$, $NHC(O)R^{25}$, $NR^{25}C(O)R^{25}$, $NHSO_2R^{25}$, $NR^{25}SO_2R^{25}$, $NHC(O)OR^{25}$, $SO_2NH_2$, $SO_2NHR^{25}$, $SO_2N(R^{25})_2$, $NHC(O)NH_2$, $NHC(O)NHR^{25}$, OH, (O), C(O)OH, $N_3$, CN, $NH_2$, $CF_3$, $OCF_3$, $CF_2CF_3$, $OCF_2CF_3$, F, Cl, Br or I;

$R^{25}$ is $R^{26}$, $R^{27}$, $R^{28}$ or $R^{29}$;

$R^{26}$ is phenyl that is unfused or fused with benzene, heteroarene, cycloalkane, cycloalkene, heterocycloalkane or heterocycloalkene;

$R^{27}$ is heteroaryl that is unfused or fused with or benzene, heteroarene, cycloalkane, cycloalkene, heterocycloalkane or heterocycloalkene;

$R^{28}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{29}$ is alkyl, alkenyl or alkynyl, each of which is unsubstituted or substituted with one or two or three or independently selected $R^{30}$, $R^{31}$, $OR^{31}$, $SR^{31}$, $S(O)R^{31}$, $SO_2R^{31}$, $NHR^{31}$, $N(R^{31})_2$, $C(O)R^{31}$, $C(O)NH_2$, $C(O)NHR^{31}$, $NHC(O)R^{31}$, $NHSO_2R^{31}$, $NHC(O)R^{31}$, $SO_2NH_2$, $SO_2NHR^{31}$, $SO_2N(R^{31})_2$, $NHC(O)NH_2$, $NHC(O)NHR^{31}$, OH, (O), C(O)OH, $N_3$, CN, $NH_2$, $CF_3$, $OCF_3$, $CF_2CF_3$, $OCF_2CF_3$, F, Cl, Br or I;

$R^{30}$ is spiroalkyl or spiroheteroalkyl;

$R^{31}$ is $R^{32}$, $R^{33}$, $R^{34}$ or $R^{35}$;

$R^{32}$ is phenyl that is unfused or fused with benzene, heteroarene, cycloalkane, cycloalkene, heterocycloalkane or heterocycloalkene;

$R^{33}$ is heteroaryl that is unfused or fused with or benzene, heteroarene, cycloalkane, cycloalkene, heterocycloalkane or heterocycloalkene;

$R^{34}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{35}$ is alkyl, alkenyl or alkynyl, each of which is unsubstituted or substituted with one or two or three of independently selected $R^{36}$, $OR^{36}$, $SR^{36}$, $S(O)R^{36}$, $SO_2R^{36}$, $NH_2$, $NHR^{36}$, $N(R^{36})_2$, $C(O)R^{36}$, $C(O)OR^{36}$, $C(O)NH_2$, $C(O)NHR^{36}$, $NHC(O)R^{36}$, $NR^{36}C(O)R^{36}$, $NHSO_2R^{36}$, $NHC(O)OR^{36}$, $SO_2NH_2$, $SO_2NHR^{36}$, $SO_2N(R^{36})_2$, $NHC(O)NH_2$, $NHC(O)NHR^{36}$, OH, (O), C(O)OH, $N_3$, CN, $NH_2$, $CF_3$, $OCF_3$, $CF_2CF_3$, $OCF_2CF_3$, F, Cl, Br or I;

$R^{36}$ is $R^{37}$, $R^{38}$, $R^{39}$, or $R^{40}$;

$R^{37}$ is phenyl that is unfused or fused with benzene, heteroarene, cycloalkane, cycloalkene, heterocycloalkane or heterocycloalkene;

$R^{38}$ is heteroaryl that is unfused or fused with or benzene, heteroarene, cycloalkane, cycloalkene, heterocycloalkane or heterocycloalkene;

$R^{39}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{40}$ is alkyl, alkenyl or alkynyl, each of which is unsubstituted or substituted with one or two of independently selected phenyl, heteroaryl, cycloalkyl, cycloalkenyl, heterocycloalkyl or heterocycloalkenyl;

wherein $R^{21}$, $R^{22}$, $R^{23}$, $R^{26}$, $R^{27}$, $R^{28}$, $R^{32}$, $R^{33}$, $R^{34}$, $R^{37}$, $R^{38}$ and $R^{39}$ are independently unsubstituted or substituted with one or two or three or four or five of independently selected $R^{41}$, $OR^{41}$, $SR^{41}$, $S(O)R^{41}$, $SO_2R^{41}$, $C(O)R^{41}$, $C(O)OR^{41}$, $CO(O)R^{41}$, $OC(O)R^{41}$, $OC(O)OR^{41}$, $NH_2$, $NHR^{41}$, $N(R^{41})_2$, $NHC(O)R^{41}$, $NR^{41}C(O)R^{41}$, $C(O)NH_2$, $C(O)NHR^{41}$, $C(O)N(R^{41})_2$, $C(O)NHOH$, $C(O)NHOR^{41}$, $SO_2NH_2$, $SO_2NHR^{41}$, $SO_2N(R^{41})_2$, $CF_3$, $CF_2CF_3$, C(O)H, C(O)OH, $C(N)NH_2$, $C(N)NHR^{41}$, $C(N)N(R^{41})_2$, OH, (O), $N_3$, CN, $NO_2$, $CF_3$, $CF_2CF_3$, $OCF_3$, $OCF_2CF_3$, F, Cl, Br or I;

$R^{41}$ is $R^{42}$, $R^{43}$, $R^{44}$ or $R^{45}$;

$R^{42}$ is phenyl that is unfused or fused with benzene, heteroarene, cycloalkane, cycloalkene, heterocycloalkane or heterocycloalkene;

$R^{43}$ is heteroaryl that is unfused or fused with or benzene, heteroarene, cycloalkane, cycloalkene, heterocycloalkane or heterocycloalkene;

$R^{44}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{45}$ is alkyl, alkenyl or alkynyl, each of which is unsubstituted or substituted with one or two of independently selected $R^{46}$, $R^{47}$, $OR^{48}$, $SR^{48}$, $S(O)R^{48}$, $SO_2R^{48}$, $NH_2$, $NHR^{48}$, $N(R^{48})_2$, $CF_3$ or $NO_2$;

$R^{46}$ is phenyl or heteroaryl;

$R^{47}$ is cycloalkyl, cycloalkenyl, heterocycloalkyl or heterocycloalkenyl;

$R^{48}$ is alkyl substituted with one or two of independently selected phenyl, heteroaryl, cycloalkyl, cycloalkenyl, heterocycloalkyl, heterocycloalkenyl, OH, $OCH_3$, $NH_2$, $NHCH_3$, $N(CH_3)_2$, F, Cl, Br or I;

wherein $R^{42}$, $R^{43}$, $R^{44}$, $R^{46}$ and $R^{47}$ are independently unsubstituted or substituted with one or two or three or four or five of independently selected $R^{49}$, $OR^{49}$, $SR^{49}$, $S(O)R^{49}$, $SO_2R^{49}$, $C(O)R^{49}$, $C(O)OR^{49}$, $CO(O)R^{49}$, $OC(O)R^{49}$, $OC(O)OR^{49}$, $NH_2$, $NHR^{49}$, $N(R^{49})_2$, $NHC(O)R^{49}$, $NR^{49}C(O)R^{49}$, $C(O)NH_2$, $C(O)NHR^{49}$, $C(O)N(R^{49})_2$, $C(O)NHOH$, $C(O)NHOR^{49}$, $SO_2NH_2$, $SO_2NHR^{49}$, $SO_2N(R^{49})_2$, $CF_3$, $CF_2CF_3$, C(O)H, C(O)OH, $C(N)NH_2$, $C(N)NHR^{49}$, $C(N)N(R^{49})_2$, OH, (O), $N_3$, CN, $NO_2$, $CF_3$, $CF_2CF_3$, $OCF_3$, $OCF_2CF_3$, F, Cl, Br or I; and $R^{49}$ is alkyl, alkenyl or alkynyl.

Another embodiment pertains to compounds having formula (I) wherein $A^1$ and $B^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NR^1C(O)NHR^1$, $NR^1C(O)N(R^1)_2$, $SO_2NHR^1$, $SO_2N(R^1)_2$, $NHSO_2R^1$ or $NHSO_2NHR^1$;

$R^1$ is $R^2$, $R^3$ or $R^4$ or $R^5$;

$R^2$ is phenyl that is unfused or fused with benzene or cycloalkane;

$R^3$ is heteroaryl that is unfused or fused with benzene;

$R^4$ is cycloalkyl or cycloalkenyl;

$R^5$ is alkyl, alkenyl or alkynyl, each of which is unsubstituted or substituted with one or two of independently selected $R^6$, $R^7$, $OR^7$, $SR^7$, $S(O)R^7$, $SO_2R^7$, $NHR^7$, $N(R^7)_2$, F, Cl, Br or I;

$R^6$ is spiroalkyl or spiroalkenyl;

$R^7$ is $R^8$, $R^9$, $R^{10}$ or $R^{11}$;

$R^8$ is phenyl that is unfused or fused with benzene;

$R^9$ is heteroaryl that is unfused or fused with benzene;

$R^{10}$ is cycloalkyl or cycloalkenyl, each of which is unfused or fused with benzene;

wherein $R^2$, $R^3$, $R^4$, $R^8$, $R^9$ and $R^{10}$ are independently unsubstituted or substituted with one or two or three or four or five of independently selected $R^{20}$, $OR^{20}$, $SR^{20}$, $S(O)R^{20}$, $SO_2R^{20}$, $C(O)R^{20}$, $C(O)OR^{20}$, $NH_2$, $NHR^{20}$, $N(R^{20})_2$, $NHC(O)R^{20}$, $C(O)NHR^{20}$, $C(O)N(R^{20})_2$, $CF_3$, $CF_2CF_3$, C(O)H, C(O)OH, OH, (O), $N_3$, CN, $NO_2$, $CF_3$, $CF_2CF_3$, $OCF_3$, $OCF_2CF_3$, F, Cl, Br or I;

$R^{20}$ is $R^{21}$, $R^{22}$, $R^{23}$ or $R^{24}$;

$R^{21}$ is phenyl that is unfused or fused with benzene;

$R^{22}$ is heteroaryl that is unfused or fused with benzene;

$R^{23}$ is cycloalkyl, cycloalkenyl, heterocycloalkyl or heterocycloalkenyl, each of which is unfused or fused with benzene;

$R^{24}$ is alkyl, alkenyl or alkynyl, each of which is unsubstituted or substituted with one or two or three of independently selected $R^{25}$, $OR^{25}$, $SR^{25}$, $S(O)R^{25}$, $SO_2R^{25}$, $NH_2$, $NHR^{25}$, $N(R^{25})_2$, $C(O)R^{25}$, $C(O)OR^{25}$, $NHC(O)R^{25}$, $NR^{25}C(O)R^{25}$, $NR^{25}SO_2R^{25}$, $NHC(O)OR^{25}$, $OH$, $(O)$, $C(O)OH$, $N_3$, $CN$, $NH_2$, $CF_3$, $OCF_3$, $CF_2CF_3$, $OCF_2CF_3$, $F$, $Cl$, $Br$ or $I$;

$R^{25}$ is $R^{26}$, $R^{27}$, $R^{28}$ or $R^{29}$;

$R^{26}$ is phenyl that is unfused or fused with benzene;

$R^{27}$ is heteroaryl that is unfused or fused with or benzene, cycloalkane;

$R^{28}$ is cycloalkyl, cycloalkenyl, heterocycloalkyl or heterocycloalkenyl, each of which is unfused or fused with benzene;

$R^{29}$ is alkyl, alkenyl or alkynyl, each of which is unsubstituted or substituted with one or two or three or independently selected $R^{30}$, $R^{31}$, $OR^{31}$, $SR^{31}$, $S(O)R^{31}$, $SO_2R^{31}$, $NHR^{31}$, $N(R^{31})_2$, $C(O)R^{31}$, $C(O)NH_2$, $C(O)NHR^{31}$, $NHC(O)R^{31}$, $NHSO_2R^{31}$, $OH$, $(O)$, $C(O)OH$, $N_3$, $CN$, $NH_2$, $CF_3$, $OCF_3$, $CF_2CF_3$, $OCF_2CF_3$, $F$, $Cl$, $Br$ or $I$;

$R^{30}$ is spiroalkyl or spiroheteroalkyl;

$R^{31}$ is $R^{32}$, $R^{33}$, $R^{34}$ or $R^{35}$;

$R^{32}$ is phenyl that is unfused or fused with benzene;

$R^{33}$ is heteroaryl that is unfused or fused with or benzene;

$R^{34}$ is heterocycloalkyl or heterocycloalkenyl, each of which is unfused or fused with benzene;

$R^{35}$ is alkyl, alkenyl or alkynyl, each of which is unsubstituted or substituted with one or two or three of independently selected $R^{36}$, $OR^{36}$, $SR^{36}$, $S(O)R^{36}$, $SO_2R^{36}$, $NH_2$, $NHR^{36}$, $N(R^{36})_2$, $C(O)R^{36}$, $F$, $Cl$, $Br$ or $I$;

$R^{36}$ is $R^{37}$, $R^{38}$, $R^{39}$, or $R^{40}$;

$R^{37}$ is phenyl that is unfused or fused with benzene;

$R^{38}$ is heteroaryl that is unfused or fused with benzene;

$R^{39}$ is cycloalkyl or cycloalkenyl each of which is unfused or fused with benzene, heteroarene, cycloalkane, cycloalkene, heterocycloalkane or heterocycloalkene;

$R^{40}$ is alkyl, alkenyl or alkynyl;

wherein $R^{21}$, $R^{22}$, $R^{23}$, $R^{26}$, $R^{27}$, $R^{28}$, $R^{32}$, $R^{33}$, $R^{34}$, $R^{37}$, $R^{38}$ and $R^{39}$ are independently unsubstituted or substituted with one or two or three or four or five of independently selected $R^{41}$, $OR^{41}$, $SR^{41}$, $S(O)R^{41}$, $SO_2R^{41}$, $C(O)R^{41}$, $C(O)OR^{41}$, $CO(O)R^{41}$, $OC(O)R^{41}$, $OC(O)OR^{41}$, $NH_2$, $NHR^{41}$, $N(R^{41})_2$, $NHC(O)R^{41}$, $NR^{41}C(O)R^{41}$, $C(O)NH_2$, $C(O)NHR^{41}$, $C(O)N(R^{41})_2$, $(O)$, $N_3$, $CN$, $NO_2$, $CF_3$, $CF_2CF_3$, $OCF_3$, $OCF_2CF_3$, $F$, $Cl$, $Br$ or $I$;

$R^{41}$ is $R^{42}$, $R^{43}$, $R^{44}$ or $R^{45}$;

$R^{42}$ is phenyl that is unfused or fused with benzene;

$R^{43}$ is heteroaryl that is unfused or fused with or benzene;

$R^{44}$ is heterocycloalkyl or heterocycloalkenyl, each of which is unfused or fused with benzene;

$R^{45}$ is alkyl, alkenyl or alkynyl, each of which is unsubstituted or substituted with one or two of independently selected $R^{46}$, $R^{47}$, $OR^{48}$, $SR^{48}$, $S(O)R^{48}$, $SO_2R^{48}$, $NH_2$, $NHR^{48}$, $N(R^{48})_2$, $CF_3$ or $NO_2$;

$R^{46}$ is phenyl or heteroaryl;

$R^{47}$ is cycloalkyl or cycloalkenyl;

$R^{48}$ is alkyl substituted with one or two of independently selected phenyl, $OH$, $OCH_3$, $NH_2$, $NHCH_3$, $N(CH_3)_2$, $F$, $Cl$, $Br$ or $I$;

wherein $R^{42}$, $R^{43}$, $R^{44}$, $R^{46}$ and $R^{47}$ are independently unsubstituted or substituted with one or two or three or four or five of independently selected $R^{49}$, $OR^{49}$, $SR^{49}$, $S(O)R^{49}$, $SO_2R^{49}$, $C(O)R^{49}$, $NH_2$, $NHR^{49}$, $N(R^{49})_2$, $F$, $Cl$, $Br$ or $I$; and $R^{49}$ is alkyl, alkenyl or alkynyl.

Still another embodiment pertains to compounds having formula (I) wherein $A^1$ and $B^1$ are independently selected $R^2$, $R^3$ or $R^4$ or $R^5$;

$R^2$ is phenyl that is unfused or fused with benzene or cycloalkane;

$R^3$ is heteroaryl that is unfused or fused with benzene;

$R^4$ is cycloalkenyl;

$R^5$ is alkyl or alkenyl each of which is unsubstituted or substituted with one or two of independently selected $R^6$ or $R^7$;

$R^6$ is spiroalkyl;

$R^7$ is phenyl;

wherein $R^2$, $R^3$, $R^4$ and $R^7$ are independently unsubstituted or substituted with one or two or three or four or five of independently selected $R^{20}$, $OR^{20}$, $SR^{20}$, $C(O)R^{20}$, $C(O)OR^{20}$, $NH_2$, $NHC(O)R^{20}$, $C(O)NHR^{20}$, $C(O)N(R^{20})_2$, $C(O)H$, $C(O)OH$, $OH$, $CN$, $NO_2$, $CF_3$, $F$, $Cl$, $Br$ or $I$;

$R^{20}$ is $R^{21}$, $R^{22}$, $R^{23}$ or $R^{24}$;

$R^{21}$ is phenyl;

$R^{22}$ is heteroaryl;

$R^{23}$ is cycloalkyl, cycloalkenyl or heterocycloalkyl;

$R^{24}$ is alkyl, alkenyl or alkynyl, each of which is unsubstituted or substituted with one or two or three of independently selected $R^{25}$, $OR^{25}$, $NH_2$, $NHR^{25}$, $N(R^{25})_2$, $C(O)OR^{25}$, $NHC(O)R^{25}$, $NR^{25}C(O)R^{25}$, $NR^{25}SO_2R^{25}$, $NHC(O)OR^{25}$, $OH$, $C(O)OH$;

$R^{25}$ is $R^{26}$, $R^{27}$, $R^{28}$ or $R^{29}$;

$R^{26}$ is phenyl that is unfused or fused with benzene;

$R^{27}$ is heteroaryl that is unfused or fused with or benzene, cycloalkane;

$R^{28}$ is cycloalkyl, heterocycloalkyl or heterocycloalkenyl, each of which is unfused or fused with benzene;

$R^{29}$ is alkyl that is unsubstituted or substituted with one or two of independently selected spiroalkyl, $R^{31}$, $OR^{31}$, $C(O)NH_2$, $NHC(O)R^{31}$;

$R^{31}$ is $R^{32}$, $R^{33}$, $R^{34}$ or $R^{35}$;

$R^{32}$ is phenyl;

$R^{33}$ is heteroaryl;

$R^{34}$ is heterocycloalkyl;

$R^{35}$ is alkyl that is unsubstituted or substituted with $R^{37}$;

$R^{37}$ is phenyl;

wherein $R^{21}$, $R^{22}$, $R^{23}$, $R^{26}$, $R^{27}$, $R^{28}$, $R^{32}$, $R^{33}$, $R^{34}$ and $R^{37}$ are independently unsubstituted or substituted with one or two or three or four or five of independently selected $R^{41}$, $OR^{41}$, $C(O)R^{41}$, $C(O)OR^{41}$, $C(O)NH_2$, $(O)$, $CN$, $CF_3$, $OCF_3$, $F$, $Cl$, $Br$ or $I$;

$R^{41}$ is $R^{42}$, $R^{43}$, $R^{44}$ or $R^{45}$;

$R^{42}$ is phenyl;

$R^{43}$ is heteroaryl;

$R^{44}$ is heterocycloalkyl;

$R^{45}$ is alkyl or alkynyl, each of which is unsubstituted or substituted with one or two of independently selected $R^{46}$, $R^{47}$, $OR^{48}$, $SR^{48}$, $CF_3$ or $NO_2$;

$R^{46}$ is phenyl or heteroaryl;

$R^{47}$ is cycloalkyl or cycloalkenyl;

$R^{48}$ is alkyl substituted with one or two of independently selected phenyl or $OH$;

wherein $R^{42}$, $R^{43}$, $R^{44}$, $R^{46}$ and $R^{47}$ are independently unsubstituted or substituted with one or two or three or four or five of independently selected $R^{49}$, $C(O)R^{49}$, F, Cl, Br or I; and $R^{49}$ is alkyl.

Still another embodiment pertains to compounds having formula (I) that are 6-(5-bromo-2-hydroxyphenyl)-4-(4-methylphenyl)-2-oxo-1,2-dihydro-3-pyridinecarbonitrile,
6-(5-bromo-2-hydroxyphenyl)-4-cyclohexyl-2-oxo-1,2-dihydro-3-pyridinecarbonitrile,
6-(5-bromo-2-hydroxyphenyl)-4-neopentyl-2-oxo-1,2-dihydro-3-pyridinecarbonitrile,
4-((1R,4R)-bicyclo[2.2.1]hept-5-en-2-yl)-6-(5-bromo-2-hydroxyphenyl)-2-oxo-1,2-dihydro-3-pyridinecarbonitrile,
6-(5-bromo-2-hydroxyphenyl)-2-oxo-4-((E)-2-phenylethenyl)-1,2-dihydro-3-pyridinecarbonitrile,
6-(5-bromo-2-hydroxyphenyl)-2-oxo-4-(2-phenylethyl)-1,2-dihydro-3-pyridinecarbonitrile,
6-(5-bromo-2-hydroxyphenyl)-2-oxo-4-(1-phenylcyclopropyl)-1,2-dihydro-3-pyridinecarbonitrile,
4-(5-(benzyloxy)-2-bromophenyl)-6-(5-bromo-2-hydroxyphenyl)-2-oxo-1,2-dihydro-3-pyridinecarbonitrile,
4-(2-bromo-5-(cyclopentyloxy)phenyl)-6-(5-bromo-2-hydroxyphenyl)-2-oxo-1,2-dihydro-3-pyridinecarbonitrile,
4-(2-bromo-5-(4-cyanophenoxy)phenyl)-6-(5-bromo-2-hydroxyphenyl)-2-oxo-1,2-dihydro-3-pyridinecarbonitrile,
6-(5-bromo-2-hydroxyphenyl)-4-(3-(4-tert-butylphenoxy)phenyl)-2-oxo-1,2-dihydro-3-pyridinecarbonitrile,
6-(5-bromo-2-hydroxyphenyl)-5-methyl-4-(4-methylphenyl)-2-oxo-1,2-dihydro-3-pyridinecarbonitrile,
6-(5-chloro-2-hydroxyphenyl)-5-methyl-4-(4-methylphenyl)-2-oxo-1,2-dihydro-3-pyridinecarbonitrile,
6-(2-amino-5-chlorophenyl)-4-(4-methylphenyl)-2-oxo-1,2-dihydro-3-pyridinecarbonitrile,
N-(4-chloro-2-(5-cyano-4-(4-methylphenyl)-6-oxo-1,6-dihydropyridin-2-yl)phenyl)acetamide,
6-(5-bromo-2-hydroxyphenyl)-2-oxo-4-(3-(trifluoromethyl)phenyl)-1,2-dihydro-3-pyridinecarbonitrile,
6-(5-bromo-2-hydroxyphenyl)-4-(3-chlorophenyl)-2-oxo-1,2-dihydro-3-pyridinecarbonitrile,
6-(5-bromo-2-hydroxyphenyl)-4-(3-chloro-4-methoxyphenyl)-2-oxo-1,2-dihydro-3-pyridinecarbonitrile,
6-(5-bromo-2-hydroxyphenyl)-4-(3-cyanophenyl)-2-oxo-1,2-dihydro-3-pyridinecarbonitrile,
6-(5-bromo-2-hydroxyphenyl)-4-(2-(methylsulfanyl)phenyl)-2-oxo-1,2-dihydro-3-pyridinecarbonitrile,
6-(5-bromo-2-hydroxyphenyl)-4-(4-nitrophenyl)-2-oxo-1,2-dihydro-3-pyridinecarbonitrile,
6-(5-bromo-2-hydroxyphenyl)-4-(3-fluoro-5-(trifluoromethyl)phenyl)-2-oxo-1,2-dihydro-3-pyridinecarbonitrile,
6-(5-bromo-2-hydroxyphenyl)-4-(2,5-dichlorophenyl)-2-oxo-1,2-dihydro-3-pyridinecarbonitrile,
6-(5-bromo-2-hydroxyphenyl)-4-(2,4-dimethylphenyl)-2-oxo-1,2-dihydro-3-pyridinecarbonitrile,
6-(5-bromo-2-hydroxyphenyl)-4-(2,5-dimethylphenyl)-2-oxo-1,2-dihydro-3-pyridinecarbonitrile,
6-(3-amino-2-hydroxy-5-methylphenyl)-4-(2,5-dichlorophenyl)-2-oxo-1,2-dihydro-3-pyridinecarbonitrile,
6-(5-chloro-2-hydroxy-4-methylphenyl)-4-(4-methylphenyl)-2-oxo-1,2-dihydro-3-pyridinecarbonitrile,
6-(3,5-dibromo-2-hydroxyphenyl)-4-(4-methylphenyl)-2-oxo-1,2-dihydro-3-pyridinecarbonitrile,
6-(2-hydroxy-4-methoxyphenyl)-4-(4-methylphenyl)-2-oxo-1,2-dihydro-3-pyridinecarbonitrile,
6-(5-cyano-2-hydroxyphenyl)-4-(2,4-dimethylphenyl)-2-oxo-1,2-dihydro-3-pyridinecarbonitrile,
6-(5-chloro-4-ethyl-2-hydroxyphenyl)-4-(4-methylphenyl)-2-oxo-1,2-dihydro-3-pyridinecarbonitrile,
4-(2,5-dichlorophenyl)-6-(2-hydroxy-3,5-diisopropylphenyl)-2-oxo-1,2-dihydro-3-pyridinecarbonitrile,
4-(2,5-dichlorophenyl)-6-(3-hydroxy-5,5,8,8-tetramethyl-5,6,7,8-tetrahydronaphthalen-2-yl)-2-oxo-1,2-dihydro-3-pyridinecarbonitrile,
6-(4'-chloro-4-hydroxy(1,1'-biphenyl)-3-yl)-4-(2-chloro-5-(trifluoromethyl)phenyl)-2-oxo-1,2-dihydro-3-pyridinecarbonitrile,
4-(2,5-dichlorophenyl)-6-(5-((1E)-3,3-dimethyl-1-butenyl)-2-hydroxyphenyl)-2-oxo-1,2-dihydro-3-pyridinecarbonitrile,
6-(5-benzyl-2-hydroxyphenyl)-4-(2,5-dichlorophenyl)-2-oxo-1,2-dihydro-3-pyridinecarbonitrile,
6-(5-(1-cyclohexen-1-yl)-2-hydroxyphenyl)-4-(2,5-dichlorophenyl)-2-oxo-1,2-dihydro-3-pyridinecarbonitrile,
4-(2,5-dichlorophenyl)-6-(2-hydroxy-5-(4-methyl-3-thienyl)phenyl)-2-oxo-1,2-dihydro-3-pyridinecarbonitrile,
6-(5-butyl-2-hydroxyphenyl)-4-(2,5-dichlorophenyl)-2-oxo-1,2-dihydro-3-pyridinecarbonitrile,
4-(2,5-dichlorophenyl)-6-(2-hydroxy-5-(pyridin-4-yl)phenyl)-2-oxo-1,2-dihydro-3-pyridinecarbonitrile,
4-(2,5-dichlorophenyl)-6-(4-hydroxy-4'-(trifluoromethyl)(1,1'-biphenyl)-3-yl)-2-oxo-1,2-dihydro-3-pyridinecarbonitrile,
6-(3'-cyano-4-hydroxy(1,1'-biphenyl)-3-yl)-4-(2,5-dichlorophenyl)-2-oxo-1,2-dihydro-3-pyridinecarbonitrile,
6-(5-cyclopentyl-2-hydroxyphenyl)-4-(2,5-dichlorophenyl)-2-oxo-1,2-dihydro-3-pyridinecarbonitrile,
6-(5-(cyclopropylethynyl)-2-hydroxyphenyl)-4-(2,5-dichlorophenyl)-2-oxo-1,2-dihydro-3-pyridinecarbonitrile,
6-(4-(benzyloxy)-2-hydroxyphenyl)-4-(2,5-dichlorophenyl)-2-oxo-1,2-dihydro-3-pyridinecarbonitrile,
6-(5-bromo-2-hydroxyphenyl)-4-(1-naphthyl)-2-oxo-1,2-dihydro-3-pyridinecarbonitrile,
6-(5-bromo-2-hydroxyphenyl)-4-(2-naphthyl)-2-oxo-1,2-dihydro-3-pyridinecarbonitrile,
4-(5-bromo-2-furyl)-6-(5-bromo-2-hydroxyphenyl)-2-oxo-1,2-dihydro-3-pyridinecarbonitrile,
6-(5-bromo-2-hydroxyphenyl)-4-(4-bromo-2-thienyl)-2-oxo-1,2-dihydro-3-pyridinecarbonitrile,
6-(5-bromo-2-hydroxyphenyl)-4-(5-methyl-2-thienyl)-2-oxo-1,2-dihydro-3-pyridinecarbonitrile,
6-(5-bromo-2-hydroxyphenyl)-4-(5-bromo-2-thienyl)-2-oxo-1,2-dihydro-3-pyridinecarbonitrile,
4-(1-benzofuran-2-yl)-6-(5-bromo-2-hydroxyphenyl)-2-oxo-1,2-dihydro-3-pyridinecarbonitrile,
4-(1-benzothien-3-yl)-6-(5-bromo-2-hydroxyphenyl)-2-oxo-1,2-dihydro-3-pyridinecarbonitrile,
6-(5-bromo-2-hydroxyphenyl)-4-(2,5-dichlorothien-3-yl)-2-oxo-1,2-dihydro-3-pyridinecarbonitrile,
6-(5-bromo-2-hydroxyphenyl)-4-(2-chloro-5-iodophenyl)-2-oxo-1,2-dihydro-3-pyridinecarbonitrile,
6-(5-bromo-2-hydroxyphenyl)-4-(2-chloroquinolin-3-yl)-2-oxo-1,2-dihydro-3-pyridinecarbonitrile,
6-(5-bromo-2-hydroxyphenyl)-4-(4-chloro(1,1'-biphenyl)-3-yl)-2-oxo-1,2-dihydro-3-pyridinecarbonitrile,
6-(5-chloro-3-cyano-2-hydroxyphenyl)-4-(4-methylphenyl)-2-oxo-1,2-dihydro-3-pyridinecarbonitrile,
4-(2,5-dichlorophenyl)-6-(4-hydroxy(1,1'-biphenyl)-3-yl)-2-oxo-1,2-dihydro-3-pyridinecarbonitrile,
6-(3-bromo-5-chloro-2-hydroxyphenyl)-4-(2-chloro-5-(trifluoromethyl)phenyl)-2-oxo-1,2-dihydro-3-pyridinecarbonitrile, (5-chloro-3-(4-(2-chloro-5-(trifluoromethyl)phenyl)-5-cyano-6-oxo-1,6-dihydropyridin-2-yl)-2-hydroxyphenyl)acetic acid,
6-(5-chloro-2-hydroxyphenyl)-4-(2-chloro-5-(trifluoromethyl)phenyl)-2(1H)-pyridinone,
6-(5-chloro-2-hydroxyphenyl)-4-(2-chloro-5-(trifluoromethyl)phenyl)-3-methyl-2(1H)-pyridinone,
(2E)-1-(3,5-dichloro-2-hydroxyphenyl)-3-(4-methylphenyl)-2-propen-1-one,
3-bromo-6-(3,5-dichloro-2-hydroxyphenyl)-4-(4-methylphenyl)-2(1H)-pyridinone,
3-chloro-6-(3,5-dichloro-2-hydroxyphenyl)-4-(4-methylphenyl)-2(1H)-pyridinone,
6-(5-chloro-2-hydroxyphenyl)-4-(2-chloro-5-(trifluoromethyl)phenyl)-2-oxo-1,2-dihydro-3-pyridinecarbonitrile,
6-(5-chloro-2-hydroxy-3-iodophenyl)-4-(2-chloro-5-(trifluoromethyl)phenyl)-2-oxo-1,2-dihydro-3-pyridinecarbonitrile,
(2E)-3-(5-chloro-3-(4-(2-chloro-5-(trifluoromethyl)phenyl)-5-cyano-6-oxo-1,6-dihydropyridin-2-yl)-2-hydroxyphenyl)-2-propenoic acid,
tert-butyl (2E)-3-(5-chloro-3-(4-(2-chloro-5-(trifluoromethyl)phenyl)-5-cyano-6-oxo-1,6-dihydropyridin-2-yl)-2-hydroxyphenyl)-2-propenylcarbamate,
tert-butyl 3-(5-chloro-3-(4-(2-chloro-5-(trifluoromethyl)phenyl)-5-cyano-6-oxo-1,6-dihydropyridin-2-yl)-2-hydroxyphenyl)-2-propynylcarbamate,
6-(3-(3-amino-1-propynyl)-5-chloro-2-hydroxyphenyl)-4-(2-chloro-5-(trifluoromethyl)phenyl)-2-oxo-1,2-dihydro-3-pyridinecarbonitrile,
6-(5-chloro-3-formyl-2-hydroxyphenyl)-4-(2-chloro-5-(trifluoromethyl)phenyl)-2-oxo-1,2-dihydro-3-pyridinecarbonitrile,
6-(5-chloro-2-hydroxy-3-(hydroxymethyl)phenyl)-4-(2-chloro-5-(trifluoromethyl)phenyl)-2-oxo-1,2-dihydro-3-pyridinecarbonitrile,
butyl 5-chloro-3-(4-(2-chloro-5-(trifluoromethyl)phenyl)-5-cyano-6-oxo-1,6-dihydropyridin-2-yl)-2-hydroxybenzoate,
5-chloro-3-(4-(2-chloro-5-(trifluoromethyl)phenyl)-5-cyano-6-oxo-1,6-dihydropyridin-2-yl)-2-hydroxybenzoic acid,
6-(3-((4-benzyl-1-piperidinyl)carbonyl)-5-chloro-2-hydroxyphenyl)-4-(2-chloro-5-(trifluoromethyl)phenyl)-2-oxo-1,2-dihydro-3-pyridinecarbonitrile,
tert-butyl 2-((5-chloro-3-(4-(2-chloro-5-(trifluoromethyl)phenyl)-5-cyano-6-oxo-1,6-dihydropyridin-2-yl)-2-hydroxybenzoyl)amino)ethylcarbamate,
1-(5-chloro-3-(4-(2-chloro-5-(trifluoromethyl)phenyl)-5-cyano-6-oxo-1,6-dihydropyridin-2-yl)-2-hydroxybenzoyl)-4-piperidinecarboxamide,
5-chloro-3-(4-(2-chloro-5-(trifluoromethyl)phenyl)-5-cyano-6-oxo-1,6-dihydropyridin-2-yl)-2-hydroxy-N-(4-methoxybenzyl)benzamide,
5-chloro-3-(4-(2-chloro-5-(trifluoromethyl)phenyl)-5-cyano-6-oxo-1,6-dihydropyridin-2-yl)-N-(3-(dimethylamino)propyl)-2-hydroxy-N-methylbenzamide,
5-chloro-3-(4-(2-chloro-5-(trifluoromethyl)phenyl)-5-cyano-6-oxo-1,6-dihydropyridin-2-yl)-N-(2-(3,4-dimethoxyphenyl)ethyl)-2-hydroxy-N-methylbenzamide,
5-chloro-3-(4-(2-chloro-5-(trifluoromethyl)phenyl)-5-cyano-6-oxo-1,6-dihydropyridin-2-yl)-2-hydroxy-N-methyl-N-(2-(pyridin-2-yl)ethyl)benzamide,
6-(5-chloro-3-((4-ethylpiperazin-1-yl)carbonyl)-2-hydroxyphenyl)-4-(2-chloro-5-(trifluoromethyl)phenyl)-2-oxo-1,2-dihydro-3-pyridinecarbonitrile,
6-(5-chloro-2-hydroxy-3-((4-(pyridin-2-yl)piperazin-1-yl)carbonyl)phenyl)-4-(2-chloro-5-(trifluoromethyl)phenyl)-2-oxo-1,2-dihydro-3-pyridinecarbonitrile,
6-(5-chloro-2-hydroxy-3-((4-(2-(2-hydroxyethoxy)ethyl)piperazin-1-yl)carbonyl)phenyl)-4-(2-chloro-5-(trifluoromethyl)phenyl)-2-oxo-1,2-dihydro-3-pyridinecarbonitrile,
6-(5-chloro-3-((4-(4-fluorophenyl)piperazin-1-yl)carbonyl)-2-hydroxyphenyl)-4-(2-chloro-5-(trifluoromethyl)phenyl)-2-oxo-1,2-dihydro-3-pyridinecarbonitrile,
6-(5-chloro-2-hydroxy-3-((4-methyl-1,4-diazepan-1-yl)carbonyl)phenyl)-4-(2-chloro-5-(trifluoromethyl)phenyl)-2-oxo-1,2-dihydro-3-pyridinecarbonitrile,
6-(5-chloro-2-hydroxy-3-((methylamino)methyl)phenyl)-4-(2-chloro-5-(trifluoromethyl)phenyl)-2-oxo-1,2-dihydro-3-pyridinecarbonitrile,
6-(3-((4-benzylpiperidin-1-yl)methyl)-5-chloro-2-hydroxyphenyl)-4-(2-chloro-5-(trifluoromethyl)phenyl)-2-oxo-1,2-dihydro-3-pyridinecarbonitrile,
6-(3-((4-benzylpiperazin-1-yl)methyl)-5-chloro-2-hydroxyphenyl)-4-(2-chloro-5-(trifluoromethyl)phenyl)-2-oxo-1,2-dihydro-3-pyridinecarbonitrile,
tert-butyl 4-(((5-chloro-3-(4-(2-chloro-5-(trifluoromethyl)phenyl)-5-cyano-6-oxo-1,6-dihydropyridin-2-yl)-2-hydroxybenzyl)(methyl)amino)carbonyl)-1-piperidinecarboxylate,
N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide,
1-acetyl-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide,
N-(5-chloro-3-(4-(2-chloro-5-(trifluoromethyl)phenyl)-5-cyano-6-oxo-1,6-dihydropyridin-2-yl)-2-hydroxybenzyl)-N-methyl-2-(3-pyridinyl)acetamide,
N-(5-chloro-3-(4-(2-chloro-5-(trifluoromethyl)phenyl)-5-cyano-6-oxo-1,6-dihydropyridin-2-yl)-2-hydroxybenzyl)-N,5-dimethyl-1-phenyl-1H-pyrazole-4-carboxamide,
N-(5-chloro-3-(4-(2-chloro-5-(trifluoromethyl)phenyl)-5-cyano-6-oxo-1,6-dihydropyridin-2-yl)-2-hydroxybenzyl)-N-methyl-1,3-thiazole-4-carboxamide,
N-(5-chloro-3-(4-(2-chloro-5-(trifluoromethyl)phenyl)-5-cyano-6-oxo-1,6-dihydropyridin-2-yl)-2-hydroxybenzyl)-N-methyl-3-furamide,
N-(5-chloro-3-(4-(2-chloro-5-(trifluoromethyl)phenyl)-5-cyano-6-oxo-1,6-dihydropyridin-2-yl)-2-hydroxybenzyl)-N-methyl-1H-indole-3-carboxamide,
N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-oxo-4,5,6,7-tetrahydro-1-benzofuran-3-carboxamide,
6-chloro-N-(5-chloro-3-(4-(2-chloro-5-(trifluoromethyl)phenyl)-5-cyano-6-oxo-1,6-dihydropyridin-2-yl)-2-hydroxybenzyl)-N-methyl-2H-chromene-3-carboxamide,
N-(5-chloro-3-(4-(2-chloro-5-(trifluoromethyl)phenyl)-5-cyano-6-oxo-1,6-dihydropyridin-2-yl)-2-hydroxybenzyl)-4-methoxy-N-methylbenzamide,
2-chloro-N-(5-chloro-3-(4-(2-chloro-5-(trifluoromethyl)phenyl)-5-cyano-6-oxo-1,6-dihydropyridin-2-yl)-2-hydroxybenzyl)-N-methylbenzamide,
N-(5-chloro-3-(4-(2-chloro-5-(trifluoromethyl)phenyl)-5-cyano-6-oxo-1,6-dihydropyridin-2-yl)-2-hydroxybenzyl)-N-methyl-2-(4-methylpiperazin-1-yl)acetamide,
N-(5-chloro-3-(4-(2-chloro-5-(trifluoromethyl)phenyl)-5-cyano-6-oxo-1,6-dihydropyridin-2-yl)-2-hydroxybenzyl)-3-ethoxy-N-methylpropanamide, N$^1$-(5-chloro-3-(4-(2-chloro-5-(trifluoromethyl)phenyl)-5-cyano-6-oxo-1,6-dihydropyridin-2-yl)-2-hydroxybenzyl)-N$^1$-methyl-1,1-cyclopropanedicarboxamide, 2-(benzyloxy)-N-(5-chloro-3-(4-(2-chloro-5-(trifluoromethyl)phenyl)-5-cyano-6-oxo-1,6-dihydropyridin-2-yl)-2-hydroxybenzyl)-N-methylacetamide, N-(5-chloro-3-(4-(2-chloro-5-(trifluoromethyl)phenyl)-5-cyano-6-oxo-1,6-dihydropyridin-2-yl)-2-hydroxybenzyl)-4-methoxy-N-methylcyclohexanecarboxamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-phenylbutanamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-2-(4-methylphenoxy)acetamide, N-(2-((5-chloro-3-(4-(2-chloro-5-(trifluoromethyl)phenyl)-5-cyano-6-oxo-1,6-dihydropyridin-2-yl)-2-hydroxybenzyl)(methyl)amino)-2-oxoethyl)-2-furamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-(2-thienyl)butanamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-3-(pyrrolidin-1-yl)propanamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-3-(4-morpholinyl)propanamide, N-benzyl-N-(5-chloro-3-(4-(2-chloro-5-(trifluoromethyl)phenyl)-5-cyano-6-oxo-1,6-dihydropyridin-2-yl)-2-hydroxybenzyl)-3-(4-morpholinyl)propanamide, 6-(5-chloro-2-hydroxy-3-((propylamino)methyl)phenyl)-4-(2-chloro-5-(trifluoromethyl)phenyl)-2-oxo-1,2-dihydro-3-pyridinecarbonitrile, N-(5-chloro-3-(4-(2-chloro-5-(trifluoromethyl)phenyl)-5-cyano-6-oxo-1,6-dihydropyridin-2-yl)-2-hydroxybenzyl)-3-(4-morpholinyl)-N-propylpropanamide, N-(5-chloro-3-(4-(2-chloro-5-(trifluoromethyl)phenyl)-5-cyano-6-oxo-1,6-dihydropyridin-2-yl)-2-hydroxybenzyl)-3-(4-morpholinyl)-N-propylpropanamide, N-(5-chloro-3-(4-(2-chloro-5-(trifluoromethyl)phenyl)-5-cyano-6-oxo-1,6-dihydropyridin-2-yl)-2-hydroxybenzyl)-N,4-dimethyl-4-piperidinecarboxamide, tert-butyl 4-(((5-chloro-3-(4-(2-chloro-5-(trifluoromethyl)phenyl)-5-cyano-6-oxo-1,6-dihydropyridin-2-yl)-2-hydroxybenzyl)(methyl)amino)carbonyl)-4-phenyl-1-piperidinecarboxylate, N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-phenyl-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(4-pyridinyl)-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-1-(4-cyanophenyl)-N-methyl-4-piperidinecarboxamide, 1-(4-acetylphenyl)-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)cyclohexanecarboxamide, N-(5-chloro-3-(4-(2-chloro-5-(trifluoromethyl)phenyl)-5-cyano-6-oxo-1,6-dihydropyridin-2-yl)-2-hydroxybenzyl)benzamide, benzyl 5-chloro-3-(4-(2-chloro-5-(trifluoromethyl)phenyl)-5-cyano-6-oxo-1,6-dihydropyridin-2-yl)-2-hydroxybenzylcarbamate, 1-acetyl-N-(5-chloro-3-(4-(2-chloro-5-(trifluoromethyl)phenyl)-5-cyano-6-oxo-1,6-dihydropyridin-2-yl)-2-hydroxybenzyl)-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-N-methylacetamide, N-(5-chloro-3-(4-(2-chloro-5-(trifluoromethyl)phenyl)-5-cyano-6-oxo-1,6-dihydropyridin-2-yl)-2-hydroxybenzyl)-N-methylcyclohexanecarboxamide, N-(5-chloro-3-(4-(2-chloro-5-(trifluoromethyl)phenyl)-5-cyano-6-oxo-1,6-dihydropyridin-2-yl)-2-hydroxybenzyl)-N-methylbenzamide, N-(5-chloro-3-(4-(2-chloro-5-(trifluoromethyl)phenyl)-5-cyano-6-oxo-1,6-dihydropyridin-2-yl)-2-hydroxybenzyl)-1-(methoxyacetyl)-N-methyl-4-piperidinecarboxamide, 1-butyryl-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(2-methylbutanoyl)-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(4,4,4-trifluorobutanoyl)-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(4,4,4-trifluorobutanoyl)-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(tetrahydro-2-furanylcarbonyl)-4-piperidinecarboxamide, 1-(3-butynoyl)-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(3-nitropropanoyl)-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-1-(cyclopropylcarbonyl)-N-methyl-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-1-(cyclopropylacetyl)-N-methyl-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-1-(cyclohexylcarbonyl)-N-methyl-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-propyl-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(2-phenylethyl)-4-piperidinecarboxamide, N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(2-(2,6,6-trimethyl-1-cyclohexen-1-yl)
ethyl)-4-piperidinecarboxamide,
1-(2-(benzyloxy)ethyl)-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide,
N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(3-(5-methyl-2-furyl)butyl)-4-piperidinecarboxamide,
1-acetyl-N-((4'-chloro-5-(4-(2-chloro-5-(trifluoromethyl)phenyl)-5-cyano-6-oxo-1,6-dihydropyridin-2-yl)-4-hydroxy(1,1'-biphenyl)-3-yl)methyl)-N-methyl-4-piperidinecarboxamide,
N-((4'-chloro-5-(4-(2-chloro-5-(trifluoromethyl)phenyl)-5-cyano-6-oxo-1,6-dihydropyridin-2-yl)-4-hydroxy(1,1'-biphenyl)-3-yl)methyl)-N-methyl-3-(pyrrolidin-1-yl)propanamide,
N-((4'-chloro-5-(4-(2-chloro-5-(trifluoromethyl)phenyl)-5-cyano-6-oxo-1,6-dihydropyridin-2-yl)-4-hydroxy(1,1'-biphenyl)-3-yl)methyl)-N-methyl-3-(4-morpholinyl)propanamide,
4-(2-chloro-5-(trifluoromethyl)phenyl)-6-(5-cyclopentyl-2-hydroxy-3-((methylamino)methyl)phenyl)-2-oxo-1,2-dihydro-3-pyridinecarbonitrile,
1-acetyl-N-(3-(4-(2-chloro-5-(trifluoromethyl)phenyl)-5-cyano-6-oxo-1,6-dihydropyridin-2-yl)-5-cyclopentyl-2-hydroxybenzyl)-N-methyl-4-piperidinecarboxamide,
N-(3-(4-(2-chloro-5-(trifluoromethyl)phenyl)-5-cyano-6-oxo-1,6-dihydropyridin-2-yl)-5-cyclopentyl-2-hydroxybenzyl)-N-methyl-3-(pyrrolidin-1-yl)propanamide,
N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-propanesulfonamide,
N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-propanesulfonamide,
N-(5-chloro-3-(4-(2-chloro-5-(trifluoromethyl)phenyl)-5-cyano-6-oxo-1,6-dihydropyridin-2-yl)-2-hydroxybenzyl)(4-chlorophenyl)-N-methylmethanesulfonamide,
N-(5-chloro-3-(4-(2-chloro-5-(trifluoromethyl)phenyl)-5-cyano-6-oxo-1,6-dihydropyridin-2-yl)-2-hydroxybenzyl)-3-fluoro-N-methylbenzenesulfonamide,
N-(5-chloro-3-(4-(2-chloro-5-(trifluoromethyl)phenyl)-5-cyano-6-oxo-1,6-dihydropyridin-2-yl)-2-hydroxybenzyl)-3-methoxy-N-methylbenzenesulfonamide,
2-chloro-N-(5-chloro-3-(4-(2-chloro-5-(trifluoromethyl)phenyl)-5-cyano-6-oxo-1,6-dihydropyridin-2-yl)-2-hydroxybenzyl)-N-methylbenzenesulfonamide,
N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-propylbenzenesulfonamide,
N-(5-chloro-3-(4-(2-chloro-5-(trifluoromethyl)phenyl)-5-cyano-6-oxo-1,6-dihydropyridin-2-yl)-2-hydroxybenzyl)-N-methyl-2-naphthalenesulfonamide,
N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-(trifluoromethoxy)benzenesulfonamide
and
N-(5-chloro-3-(4-(2-chloro-5-(trifluoromethyl)phenyl)-5-cyano-6-oxo-1,6-dihydropyridin-2-yl)-2-hydroxybenzyl)-N,5-dimethyl-1-phenyl-1H-pyrazole-4-sulfonamide,
and therapeutically acceptable salts, prodrugs and salts of prodrugs thereof.

Still another embodiment pertains to compositions for treating diseases characterized by overexpression of survivin, said compositions comprising an excipient and a therapeutically effective amount of a compound having formula (I).

Still another embodiment pertains to methods of treating diseases in a patient characterized by overexpression of survivin, said methods comprising administering thereto a therapeutically effective amount of a compound having formula (I).

Still another embodiment pertains to compositions for treating acute myelogenous leukemia, B-cell lymphoma, bladder cancer, breast cancer, chronic myelogenous leukemia, colorectal cancer, gastric carcinoma, glioma, head and neck cancer, liver cancer, lung cancer, medulloblastoma, neuroblastoma, non-Hodgkin's lymphoma, osteosarcoma, ovarian cancer, prostate cancer or uterine cancer, said compositions comprising an excipient and a therapeutically effective amount of a compound having formula (I).

Still another embodiment pertains to methods of treating acute myelogenous leukemia, B-cell lymphoma, bladder cancer, breast cancer, chronic myelogenous leukemia, colorectal cancer, gastric carcinoma, glioma, head and neck cancer, liver cancer, lung cancer, medulloblastoma, neuroblastoma, non-Hodgkin's lymphoma, osteosarcoma, ovarian cancer, prostate cancer or uterine cancer in a patient, said methods comprising administering thereto a therapeutically effective amount of a compound having formula (I).

Still another embodiment pertains to compositions for treating diseases characterized by overexpression of survivin in a patient, said compositions comprising an excipient and a therapeutically effective amount of a compound having formula (I) and a therapeutically effective amount of one additional therapeutic agent or more than one additional therapeutic agent.

Still another embodiment pertains to methods of treating diseases characterized by overexpression of survivin in a patient, said methods comprising administering thereto a therapeutically effective amount of a compound having formula (I) and a therapeutically effective amount of one additional therapeutic agent or more than one additional therapeutic agent.

Still another embodiment pertains to compositions for treating acute myelogenous leukemia, B-cell lymphoma, bladder cancer, breast cancer, chronic myelogenous leukemia, colorectal cancer, gastric carcinoma, glioma, head and neck cancer, liver cancer, lung cancer, medulloblastoma, neuroblastoma, non-Hodgkin's lymphoma, osteosarcoma, ovarian cancer, prostate cancer or uterine cancer, said compositions comprising an excipient and a therapeutically effective amount of a compound having formula (I) and a therapeutically effective amount of one additional therapeutic agent or more than one additional therapeutic agent.

Still another embodiment pertains to methods of treating acute myelogenous leukemia, B-cell lymphoma, bladder cancer, breast cancer, chronic myelogenous leukemia, colorectal cancer, gastric carcinoma, glioma, head and neck cancer, liver cancer, lung cancer, medulloblastoma, neuroblastoma, non-Hodgkin's lymphoma, osteosarcoma, ovarian cancer, prostate cancer or uterine cancer in a patient, said methods comprising administering to the patient a therapeutically effective amount of a compound having formula (I) and a therapeutically effective amount of one additional therapeutic agent or more than one additional therapeutic agent.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all moieties and combinations thereof, that monovalent moieties having more than one atom are attached through their left ends.

It is also meant to be understood that a specific embodiment of a variable moiety may be the same or different as another specific embodiment having the same identifier.

The term "cycloalkane," as used herein, means $C_3$-cycloalkane, $C_4$-cycloalkane, $C_5$-cycloalkane, $C_6$-cycloalkane, $C_7$-cycloalkane and $C_8$-cycloalkane, $C_9$-cycloalkane and $C_{10}$-cycloalkane.

The term "cycloalkyl," as used herein, means $C_3$-cycloalkyl, $C_4$-cycloalkyl, $C_5$-cycloalkyl $C_6$-cycloalkyl, $C_7$-cycloalkyl, $C_8$-cycloalkyl, $C_9$-cycloalkyl and $C_{10}$-cycloalkyl.

The term "cycloalkene," as used herein, means $C_4$-cycloalkene, $C_5$-cycloalkene, $C_6$-cycloalkene, $C_7$-cycloalkene, $C_8$-cycloalkene, $C_9$-cycloalkene and $C_{10}$-cycloalkene.

The term "cycloalkenyl," as used herein, means $C_4$-cycloalkenyl, $C_5$-cycloalkenyl, $C_6$-cycloalkenyl, $C_7$-cycloalkenyl, $C_8$-cycloalkenyl, $C_9$-cycloalkenyl and $C_{10}$-cycloalkenyl.

The term "heteroarene," as used herein, means furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), $SO_2$ or NH and one or two CH moieties replaced with N.

The term "heterocycloalkene," as used herein, means cycloalkene having one or two or three $CH_2$ moieties replaced with independently selected O, S, S(O), $SO_2$ or NH and one or two CH moieties unreplaced or replaced with N and also means cycloalkene having one or two or three $CH_2$ moieties unreplaced or replaced with independently selected O, S, S(O), $SO_2$ or NH and one or two CH moieties replaced with N.

The term "heterocycloalkenyl," as used herein, means cycloalkenyl having one or two or three $CH_2$ moieties replaced with independently selected O, S, S(O), $SO_2$ or NH and one or two CH moieties unreplaced or replaced with N and also means cycloalkenyl having one or two or three $CH_2$ moieties unreplaced or replaced with independently selected O, S, S(O), $SO_2$ or NH and one or two CH moieties replaced with N.

The term "spiroalkyl," as used herein, means $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl and $C_9$-spiroalkyl.

The term "spiroalkenyl," as used herein, means $C_2$-spiroalkenyl, $C_3$-spiroalkenyl, $C_4$-spiroalkenyl, $C_5$-spiroalkenyl, $C_6$-spiroalkenyl, $C_7$-spiroalkenyl, $C_8$-spiroalkenyl and $C_9$-spiroalkenyl.

The term "spiroheteroalkyl," as used herein, means spiroalkyl having one or two $CH_2$ moieties replaced with independently selected O, S, S(O), $SO_2$ or NH and one or two CH moieties unreplaced or replaced with N and also means spiroalkyl having one or two $CH_2$ moieties unreplaced or replaced with independently selected O, S, S(O), $SO_2$ or NH and one or two CH moieties replaced with N.

The term "spiroheteroalkenyl," as used herein, means spiroalkenyl having one or two $CH_2$ moieties replaced with independently selected O, S, S(O), $SO_2$ or NH and one or two CH moieties unreplaced or replaced with N and also means spiroalkenyl having one or two $CH_2$ moieties unreplaced or replaced with independently selected O, S, S(O), $SO_2$ or NH and one or two CH moieties replaced with N.

The term "alkenyl," as used herein, means $C_2$-alkenyl, $C_3$-alkenyl, $C_4$-alkenyl, $C_5$-alkenyl and $C_6$-alkenyl.

The term "alkyl," as used herein, means $C_1$-alkyl, $C_2$-alkyl, $C_3$-alkyl, $C_4$-alkyl, $C_5$-alkyl and $C_6$-alkyl.

The term "alkynyl," as used herein, means $C_2$-alkynyl, $C_3$-alkynyl, $C_4$-alkynyl, $C_5$-alkynyl and $C_6$-alkynyl.

The term "$C_2$-alkenyl," as used herein, means ethenyl (vinyl).

The term "$C_3$-alkenyl," as used herein, means 1-propen-1-yl, 1-propen-2-yl (isopropenyl) and 1-propen-3-yl (allyl).

The term "$C_4$-alkenyl," as used herein, means 1-buten-1-yl, 1-buten-2-yl, 1,3-butadien-1-yl, 1,3-butadien-2-yl, 2-buten-1-yl, 2-buten-2-yl, 3-buten-1-yl, 3-buten-2-yl, 2-methyl-1-propen-1-yl and 2-methyl-2-propen-1-yl.

The term "$C_5$-alkenyl," as used herein, means 2-methylene-3-buten-1-yl, 2-methylenebut-1-yl, 2-methyl-1-buten-1-yl, 2-methyl-1,3-butadien-1-yl, 2-methyl-2-buten-1-yl, 2-methyl-3-buten-1-yl, 2-methyl-3-buten-2-yl, 3-methyl-1-buten-1-yl, 3-methyl-1-buten-2-yl, 3-methyl-1,3-butadien-1-yl, 3-methyl-1,3-butadien-2-yl, 3-methyl-2-buten-1-yl, 3-methyl-2-buten-2-yl, 3-methyl-3-buten-1-yl, 3-methyl-3-buten-2-yl, 1-penten-1-yl, 1-penten-2-yl, 1-penten-3-yl, 1,3-pentadien-1-yl, 1,3-penta-dien-2-yl, 1,3-pentadien-3-yl, 1,4-pentadien-1-yl, 1,4-pentadien-2-yl, 1,4-pentadien-3-yl, 2-penten-1-yl, 2-penten-2-yl, 2-penten-3-yl, 2,4-pentadien-1-yl, 2,4-pentadien-2-yl, 3-penten-1-yl, 3-penten-2-yl, 4-penten-1-yl and 4-penten-2-yl.

The term "$C_6$-alkenyl," as used herein, means 2,2-dimethyl-3-buten-1-yl, 2,3-dimethyl-1-buten-1-yl, 2,3-dimethyl-1,3-butadien-1-yl, 2,3-dimethyl-2-buten-1-yl, 2,3-dimethyl-3-buten-1-yl, 2,3-dimethyl-3-buten-2-yl, 3,3-dimethyl-1-buten-1-yl, 3,3-dimethyl -1-buten-2-yl, 2-ethenyl-1,3-butadien-1-yl, 2-ethenyl-2-buten-1-yl, 2-ethyl-1-buten-1-yl, 2-ethyl-1,3-butadien-1-yl, 2-ethyl-2-buten-1-yl, 2-ethyl-3-buten-1-yl, 1-hexen-1-yl, 1-hexen-2-yl, 1-hexen-3-yl, 1,3-hexadien-1-yl, 1,3-hexadien-2-yl, 1,3-hexadien-3-yl, 1,3,5-hexatrien-1-yl, 1,3,5-hexatrien-2-yl, 1,3,5-hexatrien-3-yl, 1,4-hexadien-1-yl, 1,4-hexadien-2-yl, 1,4-hexadien-3-yl, 1,5-hexadien-1-yl, 1,5-hexadien-2-yl, 1,5-hexadien-3-yl, 2-hexen-1-yl, 2-hexen-2-yl, 2-hexen-3-yl, 2,4-hexadien-1-yl, 2,4-hexadien-2-yl, 2,4-hexadien-3-yl, 2,5-hexadien-1-yl, 2,5-hexadien-2-yl, 2,5-hexadien-3-yl, 3-hexen-1-yl, 3-hexen-2-yl, 3-hexen-3-yl, 3,5-hexadien-1-yl, 3,5-hexadien-2-yl, 3,5-hexadien-3-yl, 4-hexen-1-yl, 4-hexen-2-yl, 4-hexen-3-yl, 5-hexen-1-yl, 5-hexen-2-yl, 5-hexen-3-yl, 2-methylene-3-methyl-3-buten-1-yl, 2-methylene-3-methylbut-1-yl, 2-methylene-3-penten-1-yl, 2-methylene-4-penten-1-yl, 2-methylenepent-1-yl, 2-methylenepent-3-yl, 3-methylene-1-penten-1-yl, 3-methylene-1- penten-2-yl, 3-methylenepent-1-yl, 3-methylene-1,4-pentadien-1-yl, 3-methylene-1,4-pentadien-2-yl, 3-methylene-pent-2-yl, 2-methyl-1-penten-1-yl, 2-methyl-1-penten-3-yl, 2-methyl-1,3-pentadien-1-yl, 2-methyl-1,3-pentadien-3-yl, 2-methyl-1,4-pentadien-1-yl, 2-methyl-1,4-pentadien-3-yl, 2-methyl-2-penten-1-yl, 2-methyl-2-penten-3-yl, 2-methyl-2,4-pentadien-1-yl, 2-methyl-2,4-pentadien-3-yl, 2-methyl-3-penten-1-yl, 2-methyl-3-penten-2-yl, 2-methyl-3-penten-3-yl, 2-methyl-4-penten-1-yl, 2-methyl-4-penten-2-yl, 2-methyl-4-penten-3-yl, 3-methyl-1-penten-1-yl, 3-methyl-1-penten-2-yl, 3-methyl-1,3-pentadien-1-yl, 3-methyl-1,3-pentadien-2-yl, 3-methyl-1,4-pentadien-1-yl, 3-methyl-1,4-pentadien-2-yl, 3-methyl-2-penten-1-yl, 3-methyl-2-penten-2-yl, 3-methyl-2,4-pentadien-1-yl, 3-methyl-3-penten-1-yl, 3-methyl-3-penten-2-yl, 3-methyl-4-penten-1-yl, 3-methyl-4-penten-2-yl, 3-methyl-4-penten-3-yl, 4-methyl-1-penten-1-yl, 4-methyl-1-penten-2-yl, 4-methyl-1-penten-3-yl, 4-methyl-1,3-pentadien-1-yl, 4-methyl-1,3-pentadien-2-yl, 4-methyl-1,3-pentadien-3-yl, 4-methyl-1,4-pentadien-1-yl, 4-methyl-1,4-pentadien-2-yl, 4-methyl-1,4-pentadien-3-yl, 4-methylene-2-penten-3-yl, 4-methyl-2-penten-1-yl, 4-methyl-2-penten-2-yl, 4-methyl-2-penten-3-yl, 4-methyl-2,4-pentadien-1-yl, 4-methyl-2,4-pentadien-2-yl, 4-methyl-3-penten-1-yl, 4-methyl-3-penten-2-yl, 4-methyl-3-penten-3-yl, 4-methyl-4-penten-1-yl and 4-methyl-4-penten-2-yl.

The term "$C_1$-alkyl," as used herein, means methyl.

The term "$C_2$-alkyl," as used herein, means ethyl.

The term "$C_3$-alkyl," as used herein, means prop-1-yl and prop-2-yl (isopropyl).

The term "$C_4$-alkyl," as used herein, means but-1-yl, but-2-yl, 2-methylprop-1-yl and 2-methylprop-2-yl (tert-butyl).

The term "$C_5$-alkyl," as used herein, means 2,2-dimethylprop-1-yl (neo-pentyl), 2-methylbut-1-yl, 2-methylbut-2-yl, 3-methylbut-1-yl, 3-methylbut-2-yl, pent-1-yl, pent-2-yl and pent-3-yl.

The term "$C_6$-alkyl," as used herein, means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl and 4-methylpent-2-yl.

The term "$C_2$-alkynyl," as used herein, means ethynyl (acetylenyl).

The term "$C_3$-alkynyl," as used herein, means 1-propyn-1-yl and 2-propyn-1-yl (propargyl).

The term "$C_4$-alkynyl," as used herein, means 1-butyn-1-yl, 1,3-butadiyn-1-yl, 2-butyn-1-yl, 3-butyn-1-yl and 3-butyn-2-yl.

The term "$C_5$-alkynyl," as used herein, means 2-methyl-3-butyn-1-yl, 2-methyl-3-butyn-2-yl, 3-methyl-1-butyn-1-yl, 1,3-pentadiyn-1-yl, 1,4-pentadiyn-1-yl, 1,4-pentadiyn-3-yl, 2,4-pentadiyn-1-yl, 1-pentyn-1-yl, 1-pentyn-3-yl, 2-pentyn-1-yl, 3-pentyn-1-yl, 3-pentyn-2-yl, 4-pentyn-1-yl and 4-pentyn-2-yl.

The term "$C_6$-alkynyl," as used herein, means 2,2-dimethyl-3-butyn-1-yl, 3,3-dimethyl-1-butyn-1-yl, 2-ethyl-3-butyn-1-yl, 2-ethynyl-3-butyn-1-yl, 1-hexyn-1-yl, 1-hexyn-3-yl, 1,3-hexadiyn-1-yl, 1,3,5-hexatriyn-1-yl, 1,4-hexadiyn-1-yl, 1,4-hexadiyn-3-yl, 1,5-hexadiyn-1-yl, 1,5-hexadiyn-3-yl, 2-hexyn-1-yl, 2,5-hexadiyn-1-yl, 3-hexyn-1-yl, 3-hexyn-2-yl, 3,5-hexadiyn-2-yl, 4-hexyn-1-yl, 4-hexyn-2-yl, 4-hexyn-3-yl, 5-hexyn-1-yl, 5-hexyn-2-yl, 5-hexyn-3-yl, 2-methyl-3-pentyn-1-yl, 2-methyl-3-pentyn-2-yl, 2-methyl-4-pentyn-1-yl, 2-methyl-4-pentyn-2-yl, 2-methyl-4-pentyn-3-yl, 3-methyl-1-pentyn-1-yl, 3-methyl-4-pentyn-1-yl, 3-methyl-4-pentyn-2-yl, 3-methyl-1,4-pentadiyn-1-yl, 3-methyl-1,4-pentadiyn-3-yl, 3-methyl-4-pentyn-1-yl, 3-methyl-4-pentyn-3-yl, 4-methyl-1-pentyn-1-yl and 4-methyl-2-pentyn-1-yl.

The term "$C_4$-cycloalkane," as used herein, means cyclobutane.

The term "$C_5$-cycloalkane," as used herein, means cyclopentane.

The term "$C_6$-cycloalkane," as used herein, means cyclohexane.

The term "$C_7$-cycloalkane," as used herein, means cycloheptane.

The term "$C_8$-cycloalkane," as used herein, means cyclooctane.

The term "$C_9$-cycloalkane," as used herein, means cyclononane.

The term "$C_{10}$-cycloalkane," as used herein, means cyclodecane.

The term "$C_4$-cycloalkene," as used herein, means cyclobutene and 1,3-cyclobutadiene.

The term "$C_5$-cycloalkene," as used herein, means cyclopentene and 1,3-cyclopentadiene.

The term "$C_6$-cycloalkene," as used herein, means cyclohexene, 1,3-cyclohexadiene and 1,4-cyclohexadiene.

The term "$C_7$-cycloalkene," as used herein, means cycloheptene and 1,3-cycloheptadiene.

The term "$C_8$-cycloalkene," as used herein, means cyclooctene, 1,3-cyclooctadiene, 1,4-cyclooctadiene, 1,5-cyclooctadiene, 1,3,5-cyclooctatriene and 1,3,6-cyclooctatriene.

The term "$C_9$-cycloalkene," as used herein, means cyclononene, 1,3-cyclononadiene, 1,4-cyclononadiene, 1,5-cyclononadiene, 1,3,5-cyclononatriene, 1,3,6-cyclononatriene, 1,3,7-cyclononatriene and 1,3,5,7-cyclononatetraene.

The term "$C_{10}$-cycloalkene," as used herein, means cyclodecene, 1,3-cyclodecadiene, 1,4-cyclodecadiene, 1,5-cyclodecadiene, 1,6-cyclodecadiene, 1,3,5-cyclodecatriene, 1,3,6-cyclodecatriene, 1,3,5,7-cyclodecatetraene, 1,3,5,8-cyclodecatetraene and 1,3,6,8-cyclodecatetraene.

The term "$C_3$-cycloalkenyl," as used herein, means cycloprop-1-en-1-yl and cycloprop-2-en-1-yl.

The term "$C_4$-cycloalkenyl," as used herein, means cyclobut-1-en-1-yl and cyclobut-2-en-1-yl.

The term "$C_5$-cycloalkenyl," as used herein, means cyclopent-1-en-1-yl, cyclopent-2-en-1-yl, cyclopent-3-en-1-yl and cyclopenta-1,3-dien-1-yl.

The term "$C_6$-cycloalkenyl," as used herein, means cyclohex-1-en-1-yl, cyclohex-2-en-1-yl, cyclohex-3-en-1-yl, cyclohexa-1,3-dien-1-yl, cyclohexa-1,4-dien-1-yl, cyclohexa-1,5-dien-1-yl, cyclohexa-2,4-dien-1-yl and cyclohexa-2,5-dien-1-yl.

The term "$C_7$-cycloalkenyl," as used herein, means bicyclo[2.2.1]hept-2-en-1-yl, bicyclo[2.2.1]hept-2-en-2-yl, bicyclo[2.2.1]hept-2-en-5-yl, bicyclo[2.2.1]hept-2-en-7-yl, bicyclo[2.2.1]hepta-2,5-dien-1-yl, bicyclo[2.2.1]hepta-2,5-dien-2-yl, bicyclo[2.2.1]hepta-2,5-dien-7-yl, cyclohept-1-en-1-yl, cyclohept-2-en-1-yl, cyclohept-3-en-1-yl, cyclohept-4-en-1-yl, cyclohepta-1,3-dien-1-yl, cyclohepta-1,4-dien-1-yl, cyclohepta-1,5-dien-1-yl, cyclohepta-1,6-dien-1-yl, cyclohepta-2,4-dien-1-yl, cyclohepta-2,5-dien-1-yl, cyclohepta-2,6-dien-1-yl, cyclohepta-3,5-dien-1-yl, cyclohepta-1,3,5-trien-1-yl, cyclohepta-1,3,6-trien-1-yl, cyclohepta-1,4,6-trien-1-yl and cyclohepta-2,4,6-trien-1-yl.

The term "$C_8$-cycloalkenyl," as used herein, means bicyclo[2.2.2]oct-2-en-1-yl, bicyclo[2.2.2]oct-2-en-2-yl, bicyclo[2.2.2]oct-2-en-5-yl, bicyclo[2.2.2]oct-2-en-7-yl, bicyclo[2.2.2]octa-2,5-dien-1-yl, bicyclo[2.2.2]octa-2,5-dien-2-yl, bicyclo[2.2.2]octa-2,5-dien-7-yl, bicyclo[2.2.2]octa-2,5,7-trien-1-yl, bicyclo[2.2.2]octa-2,5,7-trien-2-yl cyclooct-1-en-1-yl, cyclooct-2-en-1-yl, cyclooct-3-en-1-yl, cyclooct-4-en-1-yl, cycloocta-1,3-dien-1-yl, cycloocta-1,4-dien-1-yl, cycloocta-1,5-dien-1-yl, cycloocta-1,6-dien-1-yl, cycloocta1,7-dien-1-yl, cycloocta-2,4-dien-1-yl, cycloocta-2,5-dien-1-yl, cycloocta-2,6-dien-1-yl, cycloocta-2,7-dien-1-yl, cycloocta-3,5-dien-1-yl, cycloocta-3,6-dien-1-yl, cycloocta-1,3,5-trien-1-yl, cycloocta-1,3,6-trien-1-yl, cycloocta-1,3,7-trien-1-yl, cycloocta-1,4,6-trien-1-yl, cycloocta-1,4,7-trien-1-yl, cycloocta-1,5,7-trien-1-yl, cycloocta-2,4,6-trien-1-yl, cycloocta-2,4,7-trien-1-yl, cycloocta-2,5,7-trien-1-yl and cycloocta-1,3,5,7-tetraen-1-yl.

The term "$C_9$-cycloalkenyl," as used herein, means cyclonon-1-en-1-yl, cyclonon-2-en-1-yl, cyclonon-3-en-1-yl, cyclonon-4-en-1-yl, cyclonon-5-en-1-yl, cyclonona-1,3-dien-1-yl, cyclonona-1,4-dien-1-yl, cyclonona-1,5-dien-1-yl, cyclonona-1,6-dien-1-yl, cyclonona-1,7-dien-1-yl, cyclonona-1,8-dien-1-yl, cyclonona-2,4-dien-1-yl, cyclonona-2,5-dien-1-yl, cyclonona-2,6-dien-1-yl, cyclonona-2,7-dien-1-yl, cyclonona-2,8-dien-1-yl, cyclonona-3,5-dien-1-yl, cyclonona-3,6-dien-1-yl, cyclonona-3,7-dien-1-yl, cyclonona-4,6-dien-1-yl, cyclonona-1,3,5-trien-1-yl, cyclonona-1,3,6-trien-1-yl, cyclonona-1,3,7-trien-1-yl, cyclonona-1,3,8-trien-1-yl, cyclonona-1,4,6-trien-1-yl, cyclonona-1,4,7-trien-1-yl, cyclonona-1,4,8-trien-1-yl, cyclonona-1,5,7-trien-1-yl, cyclonona-1,5,8-trien-1-yl, cyclonona-1,6,8-trien-1-yl, cyclonona-2,4,8-trien-1-yl, cyclonona-2,4,6-trien-1-yl, cyclonona-2,4,7-trien-1-yl, cyclonona-2,4,8-trien-1-yl, cyclonona-2,5,7-trien-1-yl, cyclonona-2,5,8-trien-1-yl, cyclonona-1,3,5,7-tetraen-1-yl, cyclonona-1,3,5,8-tetraen-1-yl, cyclonona-1,3,6,8-tetraen-1-yl, cyclonona-1,4,6,8-tetraen-1-yl and cyclonona-2,4,6,8-tetraen-1-yl.

The term "$C_{10}$-cycloalkenyl," as used herein, means cyclodec-1-en-1-yl, cyclodec-2-en-1-yl, cyclodec-3-en-1-yl, cyclodec-4-en-1-yl, cyclodec-5-en-1-yl, cyclodeca-1,3-dien-1-yl, cyclodeca-1,4-dien-1-yl, cyclodeca-1,5-dien-1-yl, cyclodeca-1,6-dien-1-yl, cyclodeca-1,7-dien-1-yl, cyclodeca-1,8-dien-1-yl, cyclodeca-1,9-dien-1-yl, cyclodeca-2,4-dien-1-yl, cyclodeca-2,5-dien-1-yl, cyclodeca-2,6-dien-1-yl, cyclodeca-2,7-dien-1-yl, cyclodeca-2,8-dien-1-yl, cyclodeca-2,9-dien-1-yl, cyclodeca-3,5-dien-1-yl, cyclodeca-3,6-dien-1-yl, cyclodeca-3,7-dien-1-yl, cyclodeca-3,8-dien-1-yl, cyclodeca-4,6-dien-1-yl, cyclodeca-4,7-dien-1-yl, cyclodeca-1,3,5-trien-1-yl, cyclodeca-1,3,6-trien-1-yl, cyclodeca-1,3,7-trien-1-yl, cyclodeca-1,3,8-trien-1-yl, cyclodeca-1,3,9-trien-1-yl, cyclodeca-1,4,6-trien-1-yl, cyclodeca-1,4,7-trien-1-yl, cyclodeca-1,4,8-trien-1-yl, cyclodeca-1,4,9-trien-1-yl, cyclodeca-1,5,7-trien-1-yl, cyclodeca-1,5,8-trien-1-yl, cyclodeca-1,5,9-trien-1-yl, cyclodeca-1,6,8-trien-1-yl, cyclodeca-1,6,9-trien-1-yl, cyclodeca-1,7,9-trien-1-yl, cyclodeca-2,4,6-trien-1-yl, cyclodeca-2,4,7-trien-1-yl, cyclodeca-2,4,8-trien-1-yl, cyclodeca-2,4,9-trien-1-yl, cyclodeca-2,5,7-trien-1-yl, cyclodeca-2,5,8-trien-1-yl, cyclodeca-2,5,9-trien-1-yl, cyclodeca-2,6,8-trien-1-yl, cyclodeca-3,5,7-trien-1-yl, cyclodeca-3,5,8-trien-1-yl, cyclodeca-1,3,5,7-tetraen-1-yl, cyclodeca-1,3,5,8-tetraen-1-yl, cyclodeca-1,3,5,9-tetraen-1-yl, cyclodeca-1,3,6,8-tetraen-1-yl, cyclodeca-1,3,6,9-tetraen-1-yl, cyclodeca-1,3,7,9-tetraen-1-yl, cyclodeca-1,4,6,8-tetraen-1-yl, cyclodeca-1,4,6,9-tetraen-1-yl, cyclodeca-1,4,7,9-tetraen-1-yl, cyclodeca-1,5,7,9-tetraen-1-yl, cyclodeca-2,4,6,8-tetraen-1-yl, cyclodeca-2,4,6,9-tetraen-1-yl, cyclodeca-2,4,7,9-tetraen-1-yl and cyclodeca-1,3,5,7,9-pentaen-1-yl.

The term "$C_3$-cycloalkyl," as used herein, means cycloprop-1-yl.

The term "$C_4$-cycloalkyl," as used herein, means cyclobut-1-yl.

The term "$C_5$-cycloalkyl," as used herein, means cyclopent-1-yl.

The term "$C_6$-cycloalkyl," as used herein, means cyclohex-1-yl.

The term "$C_7$-cycloalkyl," as used herein, means bicyclo[2.2.1]hept-1-yl, bicyclo[2.2.1]hept-2-yl, bicyclo[2.2.1]hept-7-yl and cyclohept-1-yl.

The term "$C_8$-cycloalkyl," as used herein, means bicyclo[2.2.2]oct-1-yl, bicyclo[2.2.2]oct-2-yl, bicyclo[2.2.2]oct-7-yl bicyclo[3.2.1]oct-1-yl, bicyclo[3.2.1]oct-2-yl, bicyclo[3.2.1]oct-3-yl, bicyclo[3.2.1]oct-6-yl, bicyclo[3.2.1]oct-8-yl and cyclooct-1-yl.

The term "$C_9$-cycloalkyl," as used herein, means cyclonon-1-yl.

The term "$C_{10}$-cycloalkyl," as used herein, means adamant-1-yl, adamant-2-yl and cyclodec-1-yl.

The term "perhaloalkyl," as used herein, means $C_1$-perhaloalkyl, $C_2$-perhaloalkyl, $C_3$-perhaloalkyl, $C_4$-perhaloalkyl, $C_5$-perhaloalkyl and $C_6$-perhaloalkyl.

The term "$C_1$-perhaloalkyl," as used herein, means $C_1$-alkyl, each of the hydrogen atoms thereof having been replaced by independently selected F, Cl or Br atoms.

The term "$C_2$-perhaloalkyl," as used herein, means $C_2$-alkyl, each of the hydrogen atoms thereof having been replaced by independently selected F, Cl or Br atoms.

The term "$C_3$-perhaloalkyl," as used herein, means $C_3$-alkyl, each of the hydrogen atoms thereof having been replaced by independently selected F, Cl or Br atoms.

The term "$C_4$-perhaloalkyl," as used herein, means $C_4$-alkyl, each of the hydrogen atoms thereof having been replaced by independently selected F, Cl or Br atoms.

The term "$C_5$-perhaloalkyl," as used herein, means $C_5$-alkyl, each of the hydrogen atoms thereof having been replaced by independently selected F, Cl or Br atoms.

The term "$C_6$-perhaloalkyl," as used herein, means $C_6$-alkyl, each of the hydrogen atoms thereof having been replaced by independently selected F, Cl or Br atoms.

The term "$C_2$-spiroalkenyl," as used herein, means ethen-1,2-ylene, both ends of which are attached to the same carbon of a $CH_2$ moiety by replacement of the hydrogen atoms thereof.

The term "$C_3$-spiroalkenyl," as used herein, means prop-1-en-1,3-ylene, both ends of which are attached to the same carbon of a $CH_2$ moiety by replacement of the hydrogen atoms thereof.

The term "$C_4$-spiroalkenyl," as used herein, means but-1-en-1,4-ylene, but-2-en-1,4-ylene and buta-1,3-dien-1,4-ylene, both ends of each of which are attached to the same carbon of a $CH_2$ moiety by replacement of the hydrogen atoms thereof.

The term "$C_5$-spiroalkenyl," as used herein, means pent-1-en-1,5-yl-ene, pent-2-en-1,5-ylene, penta-1,3-dien-1,5-ylene and penta-1,4-dien-1,5-ylene, both ends of each of which are attached to the same carbon of a $CH_2$ moiety by replacement of the hydrogen atoms thereof.

The term "$C_6$-spiroalkenyl," as used herein, means hex-1-en-1,6-ylene, hex-2-en-1,6-ylene, hexa-1,3-dien-1,6-ylene, hexa-1,4-di-en-1,6-ylene and hexa-1,3,5-trien-1,6-ylene, both ends of each of which are attached to the same carbon of a $CH_2$ moiety by replacement of the hydrogen atoms thereof.

The term "$C_7$-spiroalkenyl," as used herein, means hept-1-en-1,7-yl-ene, hept-2-en-1,7-ylene, hept-3-en-1,7-ylene, hepta-1,3-dien-1,7-ylene, hepta-1,4-dien-1,7-ylene, hepta-1, 5-dien-1,7-ylene, hepta-2,4-dien-1,7-ylene, hepta-2,5-dien-1,7-ylene, hepta-1,3,5-trien-1,7-ylene and hepta-1,3,6-trien-1,7-ylene, both ends of each of which are attached to the same carbon of a $CH_2$ moiety by replacement of the hydrogen atoms thereof.

The term "$C_2$-spiroalkyl," as used herein, means eth-1,2-ylene, both ends of which are attached to the same carbon of a $CH_2$ moiety by replacement of the hydrogen atoms thereof.

The term "$C_3$-spiroalkyl," as used herein, means prop-1,3-ylene, both ends of which are attached to the same carbon of a $CH_2$ moiety by replacement of the hydrogen atoms thereof.

The term "$C_4$-spiroalkyl," as used herein, means but-1,4-ylene, both ends of which are attached to the same carbon of a $CH_2$ moiety by replacement of the hydrogen atoms thereof.

The term "$C_5$-spiroalkyl," as used herein, means pent-1,5-ylene, both ends of which are attached to the same carbon of a $CH_2$ moiety by replacement of the hydrogen atoms thereof.

The term "$C_6$-spiroalkyl," as used herein, means hex-1,6-ylene, both ends of which are attached to the same carbon of a $CH_2$ moiety by replacement of the hydrogen atoms thereof.

The term "$C_7$-spiroalkyl," as used herein, means hept-1,7-ylene, both ends of which are attached to the same carbon of a $CH_2$ moiety by replacement of the hydrogen atoms thereof.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like. For example, compounds having formula (I) may exist as tautomers having formula

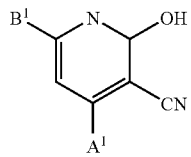

or as stabalized tautomers having formula

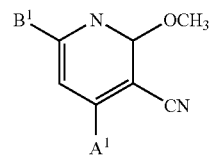

Compounds having formula (I) containing NH, C(O)OH, OH or SH moieties may have attached thereto prodrug-forming moieties. The prodrug-forming moieties are removed by metabolic processes and release compounds having the freed NH, C(O)OH, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having formula (I), produced by in vitro or in vivo metabolic processes, may also have utility for treating diseases characterized by overexpression of survivin.

Certain precursor compounds that may be metabolized in vitro or in vivo to form compounds having formula (I) may also have utility for treating diseases characterized by overexpression of survivin.

Compounds having formula (I) may exist as acid addition salts, basic addition salts or zwitterions. Salts of compounds having formula (I) are prepared during their isolation or following their purification. Acid addition salts are those derived from the reaction of a compound having formula (I) with acid. Accordingly, salts including the acetate, adipate, alginate, bicarbonate, citrate, aspartate, benzoate, benzenesulfonate, bisulfate, butyrate, camphorate, camphorsufonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having formula (I) are meant to be embraced by this invention. Basic addition salts of compounds are those derived from the reaction of the compounds having formula (I) with the bicarbonate, carbonate, hydroxide or phosphate of cations such as lithium, sodium, potassium, calcium and magnesium.

Compounds having formula (I) may be administered, for example, bucally, ophthalmically, orally, osmotically, parenterally (intramuscularly, intraperitoneally intrasternally, intravenously, subcutaneously), rectally, topically, transdermally and vaginally.

Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

To determine the binding affinity of the compounds to survivin, a 1:3 series dilution of bacterially expressed recombinant survivin protein activity cells J Biol Chem. 2003 Jan. 3; 278(1):486-90) was incubated with 1 or 0.2 μM of compound (depending on the intrinsic fluorescent intensity) in half FPIA buffer+3% DMSO+0.5% F68 +1 mM DTT for 30 minutes. The fluorescent intensity is measured at LJL Biosystems with excitation wavelength at 450/55 nm and emission wavelength at 530/25 nm. The binding affinities of representative compounds to survivin were

| | | | | | |
|---|---|---|---|---|---|
| 0.037 μM, | 0.044 μM, | 0.048 μM, | 0.06 μM, | 0.06 μM, | 0.061 μM, |
| 0.063 μM, | 0.064 μM, | 0.076 μM, | 0.08 μM, | 0.086 μM, | 0.101 μM, |
| 0.128 μM, | 0.14 μM, | 0.16 μM, | 0.2 μM, | 0.2 μM, | 0.218 μM, |
| 0.13 μM, | 0.22 μM, | 0.23 μM, | 0.26 μM, | 0.28 μM, | 0.29 μM, |
| 0.32 μM, | 0.34 μM, | 0.36 μM, | 0.4 μM, | 0.41 μM, | 0.42 μM, |
| 0.44 μM, | 0.5 μM, | 0.5 μM, | 0.51 μM, | 0.52 μM, | 0.53 μM, |
| 0.56 μM, | 0.62 μM, | 0.63 μM, | 0.7 μM, | 0.7 μM, | 0.7 μM, |
| 0.72 μM, | 0.72 μM, | 0.75 μM, | 0.81 μM, | 0.83 μM, | 0.85 μM, |
| 0.86 μM, | 0.87 μM, | 0.88 μM, | 0.9 μM, | 0.91 μM, | 0.93 μM, |
| 0.97 μM, | 0.99 μM, | 1.08 μM, | 1.1 μM, | 1.17 μM, | >1.22 μM, |
| 1.24 μM, | 1.4 μM, | 1.45 μM, | 1.47 μM, | 1.5 μM, | 1.55 μM, |
| 1.6 μM, | 1.6 μM, | 1.63 μM, | 1.7 μM, | 1.73 μM, | 1.76 μM, |
| 1.8 μM, | 1.8 μM, | 1.9 μM, | 1.91 μM, | 2 μM, | 2.03 μM, |
| 2.05 μM, | >2.1 μM, | 2.11 μM, | 2.2 μM, | 2.2 μM, | 2.2 μM, |
| 2.2 μM, | 2.2 μM, | 2.21 μM, | 2.27 μM, | 2.3 μM, | 2.5 μM, |
| 2.6 μM, | 3 μM, | >3 μM, | 3 μM, | 3.05 μM, | 3.34 μM, |
| >3.5 μM, | 3.6 μM, | 3.62 μM, | >3.65 μM, | 3.7 μM, | 3.77 μM, |
| 3.8 μM, | 3.9 μM, | 4.1 μM, | >4.2 μM, | >4.3 μM, | 4.4 μM, |
| 4.4 μM, | 4.6 μM, | >4.6 μM, | 4.78 μM, | 5.06 μM, | 5.1 μM, |
| >5.5 μM, | 5.74 μM, | 5.79 μM, | 5.94 μM, | >6 μM, | 6.12 μM, |
| >6.2 μM, | 6.51 μM, | >6.9 μM, | >7 μM, | 7.13 μM, | >9 μM, |
| 9.3 μM, | >9.6 μM, | 9.8 μM, | 9.99 μM, | >10 μM, | 10.2 μM, |
| 10.4 μM, | 11 μM, | >11 μM, | >11 μM, | 11.4 μM, | 11.9 μM, |
| 16 μM, | >16 μM, | 17.6 μM, | >19 μM, | 20.7 μM, | 15.8 μM, |
| 24.7 μM, | 29 μM and | 29.8 μM. | | | |

Because the compounds having formula (I) bind to survivin, they are expected to inhibit its activity and therefore have utility in treatment of diseases during which survivin is overexpressed, such diseases including, but not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, cervical cancer, chondrosarcoma, chordoma, choriocarcinoma, chronic leukemia, chronic lymphocytic leukemia, chronic myelocytic (granulocytic) leukemia, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, gastric carcinoma, germ cell testicular cancer, glioma, head and neck cancer, heavy chain disease, hemangioblastoma, hepatoma, hepatocellular cancer, hormone insensitive prostate cancer, leiomyosarcoma, liposarcoma, lung cancer (including small cell lung cancer), lymphagioendotheliosarcoma, lymphangiosarcoma, lymphoblastic leukemia, lymphoma (including Diffuse Large B-cell, follicular, Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer (including hormone-insensitive (refractory) prostate cancer), renal cell carcinoma, retinoblastoma, rhabdomyosarcoma, sarcoma, sebaceous gland carcinoma, seminoma, small cell lung carcinoma, solid tumors (carcinomas and sarcomas), small cell lung cancer squamous cell carcinoma, synovioma, sweat gland carcinoma, testicular cancer (including germ cell testicular cancer), Waldenström's macroglobulinemia, testicular tumors, uterine cancer and Wilms' tumor.

For example, the level of expression of survivin has been found to correlate with resistance to chemotherapy, clinical outcome, disease progression or overall prognosis in various tumor types including, but not limited to, acute myelogenous leukemia, B-cell lymphoma, bladder cancer, breast cancer, chronic myelogenous leukemia, colorectal cancer, gastric carcinoma, glioma, head and neck cancer, liver cancer, lung cancer, medulloblastoma, neuroblastoma, non-Hodgkin's lymphoma, osteosarcoma, ovarian cancer, prostate cancer and uterine cancer.

The role of survivin in acute myelogenous leukemia is described in British Journal of Haematology (2000), 111(1), 196-203 and Zhonghua Neike Zazhi (Beijing, China) (2004), 43(10), 769-772.

The role of survivin in B-cell lymphoma is described in Journal of Pathology (2005), 206(2), 123-134.

The role of survivin in bladder cancer is described in International Journal of Cancer (2005), 116(1), 100-104 and Journal of the American Medical Association (2001), 285(3), 324-328.

The role of survivin in breast cancer is described in Applied Immunohistochemistry and Molecular Morphology (2004), 12(4), 296-304, Pathology (2005), 37(2), 131-136, British Journal of Cancer (2005), 92(1), 120-124, International Journal of Cancer (2005), 114(2), 174-181 and Clinical Chemistry (Washington, D.C., United States) (2004), 50(11), 1986-1993, Oncogene (2005), 24(15), 2474-2482.

The role of survivin in chronic myelogenous leukemia is described in Cancer Letters (Amsterdam, Netherlands) (2005), 225(1), 105-110 and Leukemia and Lymphoma (2005), 46(5), 717-722.

The role of survivin in colorectal cancer is described in Cancer Research (2005), 65(11), 4881-4887, International Journal of Radiation Oncology, Biology, Physics (2004), 60(1), 149-155 and Zhongguo Linchuang Kangfu (2004), 8(29), 6389-6391, The role of survivin in gastric carcinoma is described in World Journal of Gastroenterology (2004), 10(22), 3245-3250.

The role of survivin in glioma is described in Zhongguo Shenjing Jingshen Jibing Zazhi (2004), 30(1), 63-65.

The role of survivin in head and neck cancer is described in British Journal of Cancer (2002),87(8), 883-887, British Journal of Cancer (2003), 89(12), 2244-2248, Cancer Letters (Amsterdam, Netherlands) (2005), 224(2), 253-261 and Cancer Letters (Amsterdam, Netherlands) (2005), 225(1), 27-33.

The role of survivin in liver cancer is described in Liver International (2005), 25(1), 77-84.

The role of survivin in lung cancer is described in Cancer (New York, N.Y., United States) (2005), 103(8), 1685-1692 and Clinical Cancer Research (2005), 11(11), 3974-3986.

The role of survivin in medulloblastoma is described in British Journal of Cancer (2005), 92(2), 359-365.

The role of survivin in neuroblastoma is described in Biological and Pharmaceutical Bulletin (2005), 28(4), 565-568.

The role of survivin in non-Hodgkin's lymphoma is described in Aizheng (2004), 23(1), 40-43.

The role of survivin in osteosarcoma is described in Zhongliu Fangzhi Zazhi (2004), 11(12), 1285-1288.

The role of survivin in ovarian cancer is described in International Journal of Molecular Medicine (2002), 10(2), 211-216.

The role of survivin in prostate cancer is described in Modern Pathology (2004), 17(11), 1378-1385.

The role of survivin in uterine cancer is described in Cancer Letters (Shannon, Ireland) (2002), 184(1), 105-116 and Shaanxi Yixue Zazhi (2004), 33(2), 102-104.

This invention also comprises combination therapeutic methods of treating disease conditions involving abnormal cell growth, such as cancer, in a patient comprising administering thereto a therapeutically effective amount of a pharmaceutical composition comprising a compound having formula (I) and a therapeutically effective amount of one or more than one additional therapeutic agents and/or ionizing radiation.

The combination therapeutic methods include administering compositions of a compound having formula (I) and one or more than one additional therapeutic agents or ionizing radiation to a patient using any desired dosing and/or scheduling regimen.

Compounds having formula (I) may be administered with one or more than one additional therapeutic agents, wherein the additional therapeutic agents include ionizing radiation or chemotherapeutic agents, wherein chemotherapeutic agents include, but are not limited to, carboplatin, cisplatin, cyclophosphamide, dacarbazine, dexamethasone, docetaxel, doxorubicin, etoposide, fludarabine, irinotecan, CHOP (C: Cytoxan® (cyclophosphamide); H: Adriamycin® (hydroxydoxorubicin); O: Vincristine (Oncoving®); P: prednisone), paclitaxel, rapamycin, Rituxin® (rituximab), vincristine and the like.

Compounds having formula (I) are also expected to be useful as chemotherapeutic agents in combination with therapeutic agents that include, but are not limited to, angiogenesis inhibitors, antiproliferative agents, kinase inhibitors, receptor tyrosine kinase inhibitors, aurora kinase inhibitors, polo-like kinase inhibitors, bcr-abl kinase inhibitors, growth factor inhibitors, COX-2 inhibitors, non-steroidal anti-inflammatory drugs (NSAIDS), antimitotic agents, alkylating agents, antimetabolites, intercalating antibiotics, platinum containing agents, growth factor inhibitors, ionizing radiation, cell cycle inhibitors, enzymes, topoisomerase inhibitors, biologic response modifiers, immunologicals, antibodies, hormonal therapies, retinoids/deltoids plant alkaloids, proteasome inhibitors, HSP-90 inhibitors, histone deacetylase inhibitors (HDAC) inhibitors, purine analogs, pyrimidine analogs, MEK inhibitors, CDK inhibitors, ErbB2 receptor inhibitors, mTOR inhibitors as well as other antitumor agents.

Angiogenesis inhibitors include, but are not limited to, EGFR inhibitors, PDGFR inhibitors, VEGFR inhibitors, TIE2 inhibitors, IGF1R inhibitors, matrix metalloproteinase 2 (MMP-2) inhibitors, matrix metalloproteinase 9 (MMP-9) inhibitors and thrombospondin analogs.

Examples of EGFR inhibitors include, but are not limited to, Iressa (gefitinib), Tarceva (erlotinib or OSI-774), Erbitux (cetuximab), EMD-7200, ABX-EGF, HR3, IgA antibodies, TP-38 (IVAX), EGFR fusion protein, EGF-vaccine, anti-EGFr immunoliposomes and Tykerb (lapatinib).

Examples of PDGFR inhibitors include, but are not limited to, CP-673,451 and CP-868596.

Examples of VEGFR inhibitors include, but are not limited to, Avastin (bevacizumab), Sutent (sunitinib, SU11248), Nexavar (sorafenib, BAY43-9006), CP-547,632, axitinib (AG13736), Zactima (vandetanib, ZD-6474), AEE788, AZD-2171, VEGF trap, Vatalanib (PTK-787, ZK-222584), Macugen, IM862, Pazopanib (GW786034), ABT-869 and angiozyme.

Examples of thrombospondin analogs include, but are not limited to, TSP-1, ABT-510, ABT-567 and ABT-898.

Examples of aurora kinase inhibitors include, but are not limited to, VX-680, AZD-1152 and MLN-8054.

An example of a polo-like kinase inhibitor includes, but is not limited to BI-2536.

Examples of bcr-abl kinase inhibitors include, but are not limited to, Gleevec (imatinib) and Dasatinib (BMS354825).

Examples of platinum containing agents includes, but are not limited to, cisplatin, Paraplatin (carboplatin), eptaplatin, lobaplatin, nedaplatin, Eloxatin (oxaliplatin) and satraplatin.

Examples of mTOR inhibitors includes, but are not limited to, CCI-779, rapamycin, temsirolimus, everolimus, RAD001, and AP-23573.

Examples of HSP-90 inhibitors includes, but are not limited to, geldanamycin, radicicol, 17-AAG, KOS-953, 17-DMAG, CNF-101, CNF-1010, 17-AAG-nab, NCS-683664, Mycograb, CNF-2024, PU3, PU24FC1, VER49009, IPI-504, SNX-2112 and STA-9090.

Examples of histone deacetylase inhibitors (HDAC) includes, but are not limited to, Suberoylanilide hydroxamic acid (SAHA), MS-275, Valproic acid, TSA, LAQ-824, Trapoxin, and Depsipeptide.

Examples of MEK inhibitors include, but are not limited to, PD325901, ARRY-142886, ARRY-438162 and PD98059.

Examples of CDK inhibitors include, but are not limited to, flavopyridol, MCS-5A, CVT-2584, seliciclib (CYC-202, R-roscovitine), ZK-304709, PHA-690509, BMI-1040, GPC-286199, BMS-387,032, PD0332991 and AZD-5438.

Examples of useful COX-2 inhibitors include, but are not limited to, CELEBREX™ (celecoxib), parecoxib, deracoxib, ABT-963, MK-663 (etoricoxib), COX-189 Lumiracoxib), BMS347070, RS 57067, NS-398, Bextra (valdecoxib), paracoxib, Vioxx (rofecoxib), SD-8381, 4-Methyl-2-(3,4-dimethylphenyl)-1-(4-sulfamoyl-phenyl-1H-pyrrole, T-614, JTE-522, S-2474, SVT-2016, CT-3, SC-58125 and Arcoxia (etoricoxib).

Examples of non-steroidal anti-inflammatory drugs (NSAIDs) include, but are not limited to, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol) and Oxaprozin (Daypro).

Exambles of ErbB2 receptor inhibitors include, but are not limited to, CP-724-714, CI-1033 (canertinib), Herceptin (trastuzumab), Omitarg (2C4, petuzumab), TAK-165, GW-572016 (Ionafarnib), GW-282974, EKB-569, PI-166, dHER2 (HER2 Vaccine), APC8024 (HER2 Vaccine), anti-HER/2neu bispecific antibody, B7.her2IgG3, AS HER2 trifunctional bispecfic antibodies, mAB AR-209 and mAB 2B-1.

Examples of alkylating agents include, but are not limited to, nitrogen mustard N-oxide, cyclophosphamide, ifosfamide, trofosfamide, chlorambucil, melphalan, busulfan, mitobronitol, carboquone, thiotepa, ranimustine, nimustine, Cloretazine (VNP 40101M), temozolomide, AMD-473, altretamine, AP-5280, apaziquone, brostallicin, bendamustine, carmustine, estramustine, fotemustine, glufosfamide, KW-2170, mafosfamide, and mitolactol, carmustine (BCNU), lomustine (CCNU), Busulfan, Treosulfan, Decarbazine and Temozolomide.

Examples of antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, Alimta (premetrexed disodium, LY231514, MTA), Gemzar (gemcitabine, Eli Lilly), fludarabine, 5-azacitidine, capecitabine, cladribine, clofarabine, decitabine, eflomithine, ethnylcytidine, cytosine arabinoside, hydroxyurea, TS-1, melphalan, nelarabine, nolatrexed, ocfosate, disodium premetrexed, pentostatin, pelitrexol, raltitrexed, triapine, trimetrexate, vidarabine, mycophenolic acid, tiazofurin, Ribavirin, EICAR, hydroxyurea and deferoxamine.

Examples of antibiotics include intercalating antibiotics but are not limited to, aclarubicin, actinomycin D, amrubicin, annamycin, adriamycin, bleomycin, daunorubicin, doxorubicin, elsamitrucin, epirbucin, glarbuicin, idarubicin, mitomycin C, nemorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, one or more agents selected from the group consisting of aclarubicin, amonafide, belotecan, camptothecin, 10-hydroxycamptothecin, 9-aminocamptothecin, Amsacrine, Cardioxane (Dexrazoxine), diflomotecan, irinotecan HCL (Camptosar), edotecarin, epirubicin (Ellence), etoposide, exatecan, Becatecarin, gimatecan, lurtotecan, orathecin (Supergen), BN-80915, mitoxantrone, pirarbucin, pixantrone, rubitecan, sobuzoxane, SN-38, tafluposide and topotecan.

Examples of antibodies include, but are not limited to, Rituximab, Cetuximab, Bevacizumab, Trastuzimab, specific CD40 antibodies and specific IGF1R antibodies, chTNT-1/B, Denosumab, Panorex (Edrecolomab), Rencarex (WX G250), Zanolimumab, Lintuzumab, Ticilimumab.

Examples of hormonal therapies include, but are not limited to, exemestane (Aromasin), leuprolide acetate, Buserelin, Cetrorelix, Deslorelin, Vantas, anastrozole (Arimidex), fosrelin (Zoladex), goserelin, Degarelix, doxercalciferol, fadrozole, formestane, tamoxifen citrate (tamoxifen), Arzoxifene, Casodex, Abarelix, Trelstar, finasteride, fulvestrant, toremifene, raloxifene, Trilostane (Modrastane, Desopan), lasofoxifene, letrozole, flutamide, bicalutamide, megesterol, mifepristone, nilutamide, dexamethasone, predisone and other glucocorticoids.

Examples of retinoids/deltoids include, but are not limited to, seocalcitol (EB 1089, CB 1093), lexacalcitrol (KH 1060), fenretinide, Panretin (aliretinoin), Atragen, Bexarotene and LGD-1550.

Examples of plant alkaloids include, but are not limited to, vincristine, vinblastine, vindesine and vinorelbine.

Examples of proteasome inhibitors include, but are not limited to, bortezomib (Velcade), MG132, NPI-0052 and PR-171.

Examples of immunologicals include, but are not limited to, interferons and numerous other immune enhancing agents. Interferons include interferon alpha, interferon alpha-2a, interferon alpha-2b, interferon beta, interferon gamma-1a, interferon gamma-1b (Actimmune), or interferon gamma-n1 and combinations thereof. Other agents include Alfaferone (Leukocyte alpha interferon, Cliferon), filgrastim, lentinan, sizofilan, TheraCys, ubenimex, WF-10, aldesleukin, alemtuzumab, BAM-002, decarbazine, daclizumab, denileukin, gemtuzumab ozogamicin, ibritumomab, imiquimod, lenograstim, lentinan, melanoma vaccine (Corixa), molgramostim, OncoVAC-CL, sargaramostim, tasonermin, tecleukin, thymalasin, tositumomab, Virulizin, Z-100, epratuzumab, mitumomab, oregovomab, pemtumomab (Y-muHMFG1), Provenge (Dendreon), CTLA4 (cytotoxic lymphocyte antigen 4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include krestin, lentinan, sizofiran, picibanil PF-3512676 (CpG-8954) and ubenimex.

Examples of pyrimidine analogs include, but are not limited to, 5-Fluorouracil, Floxuridine, Doxifluridine, Ratitrexed, cytarabine (ara C), Cytosine arabinoside, Fludarabine, triacetyluridine Troxacitabine (Troxatyl) and Gemcitabine.

Examples of purine analogs include but are not limited to, Mercaptopurine and thioguanine.

Examples of antimitotic agents include, but are not limited to, N-(2-((4-hydroxyphenyl)amino)pyridin-3-yl)-4-methoxybenzenesulfonamide, paclitaxel, docetaxel, epothilone D (KOS-862), PNU100940 (109881), Batabulin, Ixabepilone (BMS 247550), Patupilone, XRP-9881, Vinflunine and ZK-EPO.

Compounds of the present invention are also intended to be used as a radiosensitizer that enhances the efficacy of radiotherapy. Examples of radiotherapy include but are not limited to, external beam radiotherapy (XBRT), or teletherapy, brachtherapy or sealed source radiotherapy, unsealed source radiotherapy.

Additionally, compounds having formula (I) may be combined with other antitumor agents selected from the following agents, Genasense, Panitumumab, Zevalin, Bexxar (Corixa), Arglabin, Abarelix, Alimta, EPO906, discodermolide, Neovastat, enzastaurin, Combrestatin A4P, ZD-6126, AVE-8062, DMXAA, Thymitaq, Temodar, Revlimid, Cypat, Histerelin, Plenaizis, Atrasentan, Celeuk (celmoleukin), Satraplatin, thalomide (Thalidomide), theratope, Temilifene, ABI-007, Evista, Atamestane, Xyotax, Targretin, Triazone, Aposyn, Nevastat, Ceplene, Lanreotide, Aredia (pamidronic acid), Orathecin, Virulizin, Gastrimmune, DX-8951f, Mepact (Liposome muramyl tripeptide phophatidylethanolamine, Junovan), Dimericine (Liposome T4 endonuclease V), Onconase, BEC2, Xcytrin, CeaVac, NewTrexin, OvaRex, Osidem, Advexin, RSR13 (efaproxiral, Cotara, NBI-3001 (IL-4), Canvaxin, GMK vaccine, PEG Interferon A, Taxoprexin, gene therapy agents such as TNFerade (GeneVac) or GVAX, Interferon-alpha, Interferon-gamma, Gardasil, Eniluracil (GW 776C85), Lonafarnib, ABT-100, Tumor necrosis factor, Lovastatin, staurosporine, dactinomycin, zorubicin, Bosentan, OncoVAX, Cervarix, Cintredekin besudotox (IL-13-PE38, IL-13-PE38QQR, Interleukin 13-pseudomonas exotoxin), Oncophage (HSPPC 96), Phenoxodiol (NV 06), IGN 101, PANVAC (CEA, MUC-1 vaccinia), ampligen, ibandronic acid, miltefosine, L-asparaginase, procarbazine, Trabectedin (ET-743, Ecteinascidin 743, Yondelis), 5,10-methylenetetrahydrofolate, hydroxycarbamide, pegaspargase, pentostatin, tazarotne, TransMID 107R (KSB 311), Trisenox, Telcyta, tretinoin, acitretin, Zometa (zolendronic acid), Pandimex (Aglycon protopanaxadiol, PBD-2131), Talabostat (PT100), Tesmilifene, Tetrandrine, halofuginone, rebimastat, removab, squalamine, ukrain, paditaxel, Zinecard and Vitaxin.

Compounds having formula (I) may be made by synthetic chemical processes, examples of which are shown hereinbelow. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$ and $K_2SO_4$); AIBN means 2,2'-azobis(2-methylpropionitrile); 9-BBN means 9-borabicyclo[3.3.1]nonane; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino)ethane; DMSO means dimethylsulfoxide; dppb means 1,4-bis(diphenylphosphino)butane; dppe means 1,2-bis(diphenylphosphino)ethane; dppf means 1,1'-bis(diphenylphosphino)ferrocene; dppm means 1,1-bis(diphenylphosphino)methane; EDAC means 1-(3-dimethylaminopropyl)-3-ethylcarbodiimide; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; LDA means lithium diisopropylamide; LHMDS means lithium bis(hexamethyldisilylamide); MP-$BH_3$ means macroporus triethylammonium methylpolystyrene cyanoborohydride; LAH means lithium aluminum hydride; NCS means N-chlorosuccinimide; PyBOP means benzotriazol-1-yloxytripyrrolidinophosphonium hexafluorophosphate; TDA-1 means tris(2-(2-methoxyethoxy)ethyl)amine; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

SCHEME 1

Compounds having formula (1) may be converted to compounds having formula (2) by reacting the former, ethyl cyanoacetate acid and a base such as piperidine or pyrrolidine. The reaction is typically conducted in a solvent such as methanol, ethanol or iso-propyl alcohol at reflux temperature.

Compounds having formula (2) may be converted to compounds having formula (I) by reacting the former, compounds having formula (3) and ammonia, or the hydrochloride or acetate salt thereof. The reaction is also typically conducted in a solvent such as methanol, ethanol or iso-propyl alcohol at reflux temperature.

Alternatively, compounds having formula (I) may be prepared by reacting compounds having formulas (1), (2), (3) and ammonia, or the hydrochloride or acetate salt thereof in an asolvent such as methanol, ethanol or iso-propyl alcohol at reflux temperature.

The following examples are presented to provide what is believed to be the most useful and readily understood description of procedures and conceptual aspects of this invention.

EXAMPLE 1

A solution of 5-bromo-2-hydroxyacetophenone (645 mg), 4-methylbenzaldehyde (0.355 mL), ethyl cyanoacetate (0.319 mL) and ammonium acetate (1.85 g) in ethanol (15 mL) was refluxed for 6 hours, cooled and filtered. The filtrant was recrystallized from ethyl acetate. $^1$H NMR (300 MHz, DMSO-$d_6$) δ 7.92 (d, 1H), 7.54 (d, 2H), 7.31 (d, 2H), 7.20 (dd, 1H), 7.05 (brs, 2H), 6.73 (s, 1H), 6.57 (d, 1H), 2.38 (s, 3H).

EXAMPLE 2

This compound was made by substituting cyclohexanecarboxaldehyde for 4-methylbenzaldehyde in EXAMPLE 1. $^1$H NMR (300 MHz, DMSO-$d_6$) δ 7.92 (d, 1H), 7.15 (d, 1H), 6.90 (brs, 2H), 6.68 (s, 1H), 6.49 (d, 1H), 2.64 (m, 1H), 1.81 (m, 2H), 1.70 (m, 5H), 1.33 (m, 3H).

EXAMPLE 3A

A solution of 3,3-dimethylbutanal (0.80 mL), piperidine (0.025 mL) and ethyl cyanoacetate (0.708 mL) in toluene (7 mL) at 80° C. was stirred for 24 hours, cooled and flash chromatographed on silica gel with 15% ethyl acetete/hexanes.

EXAMPLE 3B

A solution of EXAMPLE 3A (293 mg), 5-bromo-2-hydroxyacetophenone (323 mg) and ammonium acetate (173 mg) in ethanol (6 mL) was refluxed for 2 hours, cooled and concentrated. The concentrate was flash chromatographed on silica gel with ethyl acetate. $^1$H NMR (300 MHz, DMSO-$d_6$) δ 7.75 (d, 1H), 7.24 (d, 1H), 6.62 (d, 1H), 6.60 (s, 1H), 3.17 (d, 1H), 0.99 (s, 9H).

EXAMPLE 4

This compound was made by substituting 5-norbornene-2-carboxaldehyde for 4-methylbenzaldehyde in EXAMPLE 1. $^1$H NMR (300 MHz, DMSO-$d_6$) δ 7.58 (d, 1H), 7.44 (dd, 1H), 6.88 (d, 1H), 6.32 (dd, 1H), 6.26 (dd, 1H), 5.84 (dd, 1H), 3.56 (m, 1H), 3.17 (d, 1H), 2.99 (d, 1H), 2.19 (m, 1H), 1.50 (m, 1H), 1.42 (m, 1H), 1.33 (m, 1H).

EXAMPLE 5

This compound was made by substituting trans-cinnamaldehyde for 4-methylbenzaldehyde in EXAMPLE 1. $^1$H NMR (300 MHz, DMSO-$d_6$) δ 8.01 (d, 1H), 7.85 (d, 1H), 7.67 (d, 2H), 7.45 (dd, 2H), 7.40 (d, 1H), 7.25 (dd, 1H), 7.18 (d, 1H), 7.15 (s, 1H), 7.08 (brs, 2H), 6.61 (d, 1H).

EXAMPLE 6

This compound was made by substituting 3-phenylpropanal for 4-methylbenzaldehyde in EXAMPLE 1. $^1$H NMR (300 MHz, DMSO-$d_6$) δ 7.58 (d, 1H), 7.48 (dd, 1H), 7.27 (m, 5H), 6.92 (d, 1H), 6.64 (d, 1H), 2.96 (s, 4H).

EXAMPLE 7A

A solution of 1-phenyl-1-cyclopropanecarboxylic acid (3 g) in methanol (30 mL) and ethyl acetate (20 mL) was treated with 2M trimethylsilyldiazomethane (10 mL) over 30 minutes and concentrated. The concentrate was flash chromatographed on silica gel with 10% ethyl acetete/hexanes.

EXAMPLE 7B

A solution of EXAMPLE 7A (2.97 g) in THF (55 mL) at 0° C. was treated with 1M DIBAL in THF (39 mL) over 2 hours, quenched with water, mixed with ethyl acetate (300 mL) and water (50 mL) and filtered through silica gel. The filtrate was washed with brine and concentrated. The concentrate was flash chromatographed on silica gel with 20% ethyl acetete/hexanes.

EXAMPLE 7C

A solution of EXAMPLE 7B (1.14 g) and Dess-Martin reagent (3.4 g) in dichloromethane (25 mL) was stirred for 24 hours, filtered and concentrated. The concentrate was flash chromatographed on silica gel with 10% ethyl acetete/hexanes.

EXAMPLE 7D

This compound was made by substituting EXAMPLE 7C for 4-methylbenzaldehyde in EXAMPLE 1. $^1$H NMR (300

MHz, DMSO-d$_6$) δ 7.77 (d, 1H), 7.49 (dd, 1H), 7.30 (m, 5H), 6.92 (d, 1H), 6.85 (d, 1H), 1.39 (m, 4H).

EXAMPLE 8A

A solution of 2-bromo-5-hydroxybenzaldehyde (400 mg), 60% oily NaH (88 mg), and 15-crown-5 (0.435 mL) in DMF (6 mL) was treated with benzyl bromide (0.260 mL), stirred at 90° C. for 3 hours, cooled, poured into diethyl ether, washed with 1M HCl, 1M NaOH, water and brine, and concentrated.

EXAMPLE 8B

This compound was made by substituting EXAMPLE 8A for 4-methylbenzaldehyde in EXAMPLE 1. $^1$H NMR (300 MHz, DMSO-d$_6$) δ 7.87 (d, 1H), 7.63 (d, 1H), 7.47 (d, 2H), 7.40 (dd, 2H), 7.37 (d, 1H), 7.23 (dd, 1H), 7.14 (brs, 2H), 7.07 (d, 1H), 7.03 (dd, 1H), 6.64 (s, 1H), 6.61 (d, 1H), 5.14 (s, 2H).

EXAMPLE 9A

This compound was made by substituting cyclopentyl bromide for benzyl bromide in EXAMPLE 8A.

EXAMPLE 9B

This compound was made by substituting EXAMPLE 9A for 4-methylbenzaldehyde in EXAMPLE 1. $^1$H NMR (300 MHz, DMSO-d$_6$) δ 7.82 (m, 2H), 7.63 (d, 1H), 7.50 (dd, 1H), 7.06 (d, 1H), 6.98 (dd, 1H), 6.94 (d, 1H), 4.87 (m, 1H), 1.92 (m, 2H), 1.71 (m, 4H), 1.58 (m, 2H).

EXAMPLE 10A

A solution of 2-bromo-5-hydroxybenzaldehyde (400 mg), 60% oily NaH (88 mg) and 4-fluorobenzonitrile (241 mg) in DMSO (5 mL) at 120° C. was stirred for 2 hours, cooled, poured into 1M NaOH (30 mL) and extracted with diethyl ether. The extract was concentrated, and the concentrate was flash chromatographed on silica gel with 10% ethyl acetete/hexanes.

EXAMPLE 10B

This compound was made by substituting EXAMPLE 10A for 4-methylbenzaldehyde in EXAMPLE 1. $^1$H NMR (300 MHz, DMSO-d$_6$) δ 7.87 (m, 3H), 7.81 (d, 1H), 7.25 (d, 2H), 7.21 (dd, 1H), 7.18 (d, 1H), 6.73 (s, 1H), 6.62 (d, 1H).

EXAMPLE 11

This compound was made by substituting 3-(4-tert-butylphenoxy)benzaldehyde for 4-methylbenzaldehyde in EXAMPLE 1. $^1$H NMR (300 MHz, DMSO-d$_6$) δ 7.95 (d, 1H), 7.49 (dd, 1H), 7.42 (d, 2H), 7.36 (d, 1H), 7.25 (dd, 1H), 7.23 (dd, 1H), 7.06 (brs, 2H), 7.04 (dd, 1H), 7.03 (d, 2H), 6.77 (s, 1H), 6.60 (d, 1H), 1.30 (s, 9H).

EXAMPLE 12A

A solution of 2-bromo-5-hydroxybenzaldehyde (1005 mg), tert-butyldimethylsilyl chloride (791 mg) and imidazole (715 mg) in dichloromethane (15 mL) was stirred for 1 hour, poured into 1M HCl and extracted with diethyl ether; and the extract was concentrated.

EXAMPLE 12B

A solution of EXAMPLE 12A (1.50 g) in THF (15 mL) at 0° C. was treated with 3M ethylmagnesium bromide in diethyl ether (1.74 mL), stirred for 20 minutes, quenched with methanol and concentrated. The concentrate was flash chromatographed on silica gel with 10% ethyl acetete/hexanes.

EXAMPLE 12C

This compound was made by substituting EXAMPLE 12B for EXAMPLE 7B in EXAMPLE 7C.

EXAMPLE 12D

A solution of EXAMPLE 12C (920 mg) and 1M tetrabutylammonium fluoride in THF (8 mL) in THF (2 mL) was stirred for 3 hours and treated with 1M HCl (2 mL). The layers were separated and the extract was concentrated.

EXAMPLE 12E

This compound was made by substituting EXAMPLE 12D for 5-bromo-2-hydroxyacetophenone in EXAMPLE 1. $^1$H NMR (300 MHz, DMSO-d$_6$) δ 7.47 (m, 2H), 7.35 (d, 2H), 7.27 (d, 2H), 6.91 (d, 1H), 2.39 (s, 3H), 1.57 (s, 3H).

EXAMPLE 13

This compound was made by substituting 5-chloro-2-hydroxypropiophenone for 5-bromo-2-hydroxyacetophenone in EXAMPLE 1. $^1$H NMR (300 MHz, DMSO-d$_6$) δ 7.36 (m, 4H), 7.27 (d, 2H), 6.97 (d, 1H), 2.39 (s, 3H), 1.58 (s, 3H).

EXAMPLE 14A

A solution of HNO$_3$ (1.25 mL) and H$_2$SO$_4$ (1.57 mL) at 0° C. was treated with 3-chloroacetophenone (2.08 mL), stirred for 10 minutes, poured onto ice, and extracted with diethyl ether. The extract was washed with brine and concentrated. The concentrate was flash chromatographed on silica gel with 20% ethyl acetate/hexane.

EXAMPLE 14B

This compound was made by substituting 4-methylbenzaldehyde for 3,3-dimethylbutanal in EXAMPLE 3A.

EXAMPLE 14C

This compound was made by substituting EXAMPLE 14A for 5-bromo-2-hydroxyacetophenone and EXAMPLE 14B for EXAMPLE 3A in EXAMPLE 3B.

EXAMPLE 14D

A solution of EXAMPLE 14C (138 mg) and SnCl$_2$ dihydrate (213 mg) in 12M HCl (3.75 mL), isopropanol (5 mL) and NMP (2.5 mL) at 40° C. was stirred for 24 hours, cooled and filtered. The filtrant was washed with water, ethanol and diethyl ether. $^1$H NMR (300 MHz, DMSO-d$_6$) δ 7.61 (d, 2H), 7.37 (d, 2H), 7.26 (m, 1H), 7.17 (dd, 1H), 6.77 (d, 1H), 6.50 (m, 1H), 2.39 (s, 3H).

EXAMPLE 15

A solution of EXAMPLE 14D (32 mg) and acetyl chloride (0.007 mL) in DMF (1 mL) was stirred for 30 minutes and concentrated. The concentrate was recrystallized from ethyl acetate. $^1$H NMR (300 MHz, DMSO-d$_6$) δ 12.75 (brs, 1H), 9.71 (brs, 1H), 7.74 (m, 1H), 7.56 (m, 4H), 7.38 (d, 2H), 6.42 (m, 1H), 2.39 (s, 3H), 1.98 (s, 3H).

EXAMPLE 16

This compound was made by substituting 3-trifluoromethylbenzaldehyde for 4-methylbenzaldehyde in EXAMPLE 1. $^1$H NMR (300 MHz, DMSO-$d_6$) δ 8.01 (d, 1H), 7.94 (s, 1H), 7.93 (d, 1H), 7.85 (d, 1H), 7.75 (dd, 1H), 7.24 (dd, 1H), 7.05 (brs, 2H), 6.87 (s, 1H), 6.82 (d, 1H).

EXAMPLE 17

This compound was made by substituting 3-chlorobenzaldehyde for 4-methylbenzaldehyde in EXAMPLE 1. $^1$H NMR (300 MHz, DMSO-$d_6$) δ 8.00 (d, 1H), 7.88 (s, 1H), 7.59 (m, 1H), 7.55 (s, 1H), 7.54 (dd, 1H), 7.23 (dd, 1H), 7.07 (brs, 2H), 6.82 (s, 1H), 6.61 (d, 1H).

EXAMPLE 18

This compound was made by substituting 3-chloro-4-methoxybenzaldehyde for 4-methylbenzaldehyde in EXAMPLE 1. $^1$H NMR (300 MHz, DMSO-$d_6$) δ 7.99 (d, 1H), 7.72 (d, 1H), 7.62 (dd, 1H), 7.27 (d, 1H), 7.21 (dd, 1H), 7.03 (brs, 2H), 6.78 (s, 1H), 6.58 (d, 1H), 3.93 (s, 3H).

EXAMPLE 19

This compound was made by substituting 3-cyanobenzaldehyde for 4-methylbenzaldehyde in EXAMPLE 1. $^1$H NMR (300 MHz, DMSO-$d_6$) δ 8.10 (d, 1H), 8.03 (d, 1H), 7.98 (d, 1H), 7.95 (d, 1H), 7.72 (dd, 1H), 7.26 (dd, 1H), 7.12 (brs, 2H), 6.90 (s, 1H), 6.64 (d, 1H).

EXAMPLE 20

This compound was made by substituting 2-methylthiobenzaldehyde for 4-methylbenzaldehyde in EXAMPLE 1. $^1$H NMR (300 MHz, DMSO-$d_6$) δ 7.79 (d, 1H), 7.44 (dd, 1H), 7.41 (m, 1H), 7.26 (dd, 1H), 7.23 (dd, 1H), 7.20 (dd, 1H), 6.96 (brs, 2H), 6.60 (s, 1H), 6.58 (d, 1H), 2.42 (s, 3H).

EXAMPLE 21

This compound was made by substituting 4-nitrobenzaldehyde for 4-methylbenzaldehyde in EXAMPLE 1. $^1$H NMR (300 MHz, DMSO-$d_6$) δ 8.34 (d, 2H), 8.01 (d, 1H), 7.91 (d, 2H), 7.26 (dd, 1H), 6.91 (brs, 2H), 6.88 (s, 1H), 6.64 (d, 1H).

EXAMPLE 22

This compound was made by substituting 3-fluoro-5-trifluoromethylbenzaldehyde for 4-methylbenzaldehyde in EXAMPLE 1. $^1$H NMR (300 MHz, DMSO-$d_6$) δ 8.03 (d, 1H), 7.83 (m, 3H), 7.25 (dd, 1H), 7.04 (brs, 2H), 6.91 (s, 1H), 6.63 (d, 1H).

EXAMPLE 23

This compound was made by substituting 2,5-dichlorobenzaldehyde for 4-methylbenzaldehyde in EXAMPLE 1. $^1$H NMR (300 MHz, DMSO-$d_6$) δ 7.92 (d, 1H), 7.62 (s, 1H), 7.55 (m, 2H), 7.23 (dd, 1H), 6.85 (brs, 2H), 6.75 (s, 1H), 6.62 (d, 1H).

EXAMPLE 24

This compound was made by substituting 2,4-dimethylbenzaldehyde for 4-methylbenzaldehyde in EXAMPLE 1. $^1$H NMR (300 MHz, DMSO-$d_6$) δ 9.35 (brs, 2H), 8.18 (d, 1H), 7.95 (dd, 1H), 7.82 (d, 1H), 7.53 (d, 1H), 7.20 (dd, 1H), 7.09 (s, 1H), 6.58 (d, 1H), 2.33 (s, 3H), 2.19 (s, 3H).

EXAMPLE 25

This compound was made by substituting 2,5-dimethylbenzaldehyde for 4-methylbenzaldehyde in EXAMPLE 1. $^1$H NMR (300 MHz, DMSO-$d_6$) δ 7.95 (d, 1H), 7.59 (d, 1H), 7.52 (dd, 1H), 7.27 (d, 1H), 7.13 (s, 1H), 7.03 (d, 1H), 6.85 (d, 1H), 2.37 (s, 3H), 2.30 (s, 3H).

EXAMPLE 26

A solution of 3-N-Boc-amino-2-hydroxy-5-methylacetophenone (796 mg), 2,5-dichlorobenzaldehyde (524 mg), ethyl cyanoacetate (0.320 mL) and ammonium acetate (1.85 g) in ethanol (15 mL) at 55° C. was stirred for 24 hours, cooled and concentrated. The concentrate was flash chromatographed on silica gel with 1% acetic acid/ethyl acetate. The product was taken up in 4M HCl (10 mL) and dioxane (10 mL), stirred at 60° C. for 1 hour, cooled, poured into pH 7 buffer (50 mL) and extracted with ethyl acetate. The extract was washed with brine and dried ($Na_2SO_4$), filtered, concentrated to 50 mL and refiltered. $^1$H NMR (300 MHz, DMSO-$d_6$) δ 7.85 (brs, 2H), 7.76 (s, 1H), 7.73 (m, 2H), 7.67 (dd, 1H), 7.60 (br m, 2H), 7.36 (m, 2H), 2.28 (s, 3H).

EXAMPLE 27

This compound was made by substituting 5-chloro-2-hydroxy-4-methylacetophenone for 5-bromo-2-hydroxyacetophenone in EXAMPLE 1. $^1$H NMR (300 MHz, DMSO-$d_6$) δ 7.78 (s, 1H), 7.52 (d, 2H), 7.30 (d, 2H), 7.03 (brs, 2H), 6.68 (s, 1H), 6.62 (s, 1H), 2.38 (s, 3H), 2.21 (s, 3H).

EXAMPLE 28

This compound was made by substituting 3,5-dibromo-2-hydroxyacetophenone for 5-bromo-2-hydroxyacetophenone in EXAMPLE 1. $^1$H NMR (300 MHz, DMSO-$d_6$) δ 7.94 (d, 1H), 7.56 (d, 2H), 7.53 (d, 1H), 7.32 (d, 2H), 7.07 (brs, 2H), 6.83 (s, 1H), 2.39 (s, 3H).

EXAMPLE 29

This compound was made by substituting 4-methoxy-2-hydroxyacetophenone for 5-bromo-2-hydroxyacetophenone in EXAMPLE 1. $^1$H NMR (300 MHz, DMSO-$d_6$) δ 7.63 (m, 2H), 7.57 (d, 2H), 7.36 (d, 2H), 6.72 (brs, 2H), 6.47 (m, 2H), 3.77 (s, 3H), 2.39 (s, 3H).

EXAMPLE 30

This compound was made by substituting 5-cyano-2-hydroxyacetophenone for 5-bromo-2-hydroxyacetophenone and 2,4-dimethylbenzaldehyde for 4-methylbenzaldehyde in EXAMPLE 1. $^1$H NMR (300 MHz, DMSO-$d_6$) δ 8.09 (brs, 1H), 7.77 (dd, 1H), 7.19 (m, 2H), 7.14 (dd, 1H), 7.09 (d, 1H), 6.71 (brs, 1H), 3.77 (s, 3H), 2.34 (s, 3H), 2.24 (s, 3H).

EXAMPLE 31A

A solution of 4-chloro-3-ethylphenol (2 g) and acetyl chloride (1.04 mL) in chlorobenzene (25 mL) was treated with a 1M $AlCl_3$ in nitrobenzene (15.3 mL), stirred at 100° C. for 24 hours, cooled, poured into ice-water and extracted with

37 diethyl ether. The extract was washed with brine and concentrated. The concentrate was flash chromatographed on silica gel with 10% ethyl acetete/hexanes.

EXAMPLE 31B

This compound was made by substituting EXAMPLE 31A for 5-bromo-2-hydroxyacetophenone in EXAMPLE 1. $^1$H NMR (300 MHz, DMSO-$d_6$) δ 7.79 (s, 1H), 7.53 (d, 2H), 7.31 (d, 2H), 7.10 (brs, 2H), 6.70 (s, 1H), 6.61 (s, 1H), 2.57 (q, 2H), 2.38 (s, 3H), 1.16 (t, 3H).

EXAMPLE 32A

This compound was made by substituting 2,4-diisopropylphenol for 4-chloro-3-ethylphenol in EXAMPLE 31A.

EXAMPLE 32B

This compound was made by substituting EXAMPLE 32A for 5-bromo-2-hydroxyacetophenone and 2,5-dichlorobenzaldehyde for 4-methylbenzaldehyde in EXAMPLE 1. $^1$H NMR (300 MHz, DMSO-$d_6$) δ 7.72 (d, 1H), 7.70 (s, 1H), 7.65 (d, 1H), 7.55 (br m, 2H), 7.19 (d, 1H), 2.85 (m, 2H), 1.21 (d, 6H), 1.19 (d, 6H).

EXAMPLE 33

This compound was made by substituting 6-acetyl-7-hydroxy-1,1,4,4-tetramethyltetralin for 5-bromo-2-hydroxyacetophenone and 2,5-dichlorobenzaldehyde for 4-methylbenzaldehyde in EXAMPLE 1. $^1$H NMR (300 MHz, DMSO-$d_6$) δ 7.71 (d, 1H), 7.70 (d, 1H), 7.63 (dd, 1H), 7.50 (brs, 1H), 6.91 (s, 1H), 6.75 (brs, 1H), 1.62 (brs, 4H), 1.24 (m, 12H).

EXAMPLE 34A

A solution of 5-bromo-2-hydroxyacetophenone (10 g), imidazole (6.65 g) and tert-butyldimethylsilyl chloride (7.36 g) in DMF (110 mL) at 65° C. was stirred for 4 hours, cooled and poured into diethyl ether (1 L). The extract was washed with 1M HCl, 1M NaOH and brine and dried ($Na_2SO_4$), filtered and concentrated. The concentrate was flash chromatographed on silica gel with 5% ethyl acetete/hexanes.

EXAMPLE 34B

A solution of EXAMPLE 34A (600 mg), 4-chlorobenzeneboronic acid (313 mg), and $PdCl_2$(dppf) (150 mg) in dioxane (5.5 mL) and 2M $Na_2CO_3$ (3.5 mL) at 70° C. was stirred for 24 hours, cooled, poured into 1M HCl (25 mL) and extracted with ethyl acetate. The extract was washed with brine and dried ($Na_2SO_4$), filtered and concentrated. The concentrate was flash chromatographed on silica gel with 5% ethyl acetete/hexanes.

EXAMPLE 34C

This compound was made by substituting EXAMPLE 34B for 5-chloro-2-hydroxyacetophenone in EXAMPLE 67. $^1$H NMR (300 MHz, DMSO-$d_6$) δ 8.05 (d, 1H), 7.87 (s, 2H), 7.84 (d, 1H), 7.69 (d, 2H), 7.52 (dd, 1H), 7.37 (d, 2H), 7.06 (brs, 2H), 6.99 (s, 1H), 6.77 (s, 1H).

38

EXAMPLE 35A

This compound was made by substituting trans-3,3-dimethyl-1-butene-1-boronic acid for 4-chlorobenzeneboronic acid in EXAMPLE 34B.

EXAMPLE 35B

This compound was made by substituting EXAMPLE 35A for 5-bromo-2-hydroxyacetophenone and 2,5-dichlorobenzaldehyde for 4-methylbenzaldehyde in EXAMPLE 1. $^1$H NMR (300 MHz, DMSO-$d_6$) δ 7.72 (m, 2H), 7.64 (dd, 1H), 7.60 (brs, 1H), 7.44 (dd, 1H), 6.94 (d, 1H), 6.70 (brs, 1H), 6.25 (s, 2H), 1.08 (s, 9H).

EXAMPLE 36A

This compound was made by substituting benzylboronic acid for 4-chlorobenzeneboronic acid in EXAMPLE 34B.

EXAMPLE 36B

This compound was made by substituting EXAMPLE 36A for 5-bromo-2-hydroxyacetophenone and 2,5-dichlorobenzaldehyde for 4-methylbenzaldehyde in EXAMPLE 1. $^1$H NMR (300 MHz, DMSO-$d_6$) δ 7.71 (d, 1H), 7.70 (d, 1H), 7.63 (dd, 1H), 7.55 (brs, 1H), 7.25 (m, 4H), 7.21 (dd, 1H), 7.17 (m, 1H), 6.90 (d, 1H), 6.78 (brs, 1H), 3.86 (s, 2H).

EXAMPLE 37A

This compound was made by substituting 1-cyclohexeneboronic acid for 4-chlorobenzeneboronic acid in EXAMPLE 34B.

EXAMPLE 37B

This compound was made by substituting EXAMPLE 37A for 5-bromo-2-hydroxyacetophenone and 2,5-dichlorobenzaldehyde for 4-methylbenzaldehyde in EXAMPLE 1. $^1$H NMR (300 MHz, DMSO-$d_6$) δ 7.69 (d, 1H), 7.61 (d, 1H), 7.53 (m, 2H), 7.26 (dd, 1H), 7.06 (brs, 2H), 6.71 (s, 1H), 6.66 (d, 1H), 6.00 (t, 1H), 2.33 (m, 2H), 2.11 (m, 2H), 1.66 (m, 2H), 1.57 (m, 2H).

EXAMPLE 38A

This compound was made by substituting 4-methylthiophene-3-boronic acid for 4-chlorobenzeneboronic acid in EXAMPLE 34B.

EXAMPLE 38B

This compound was made by substituting EXAMPLE 38A for 5-bromo-2-hydroxyacetophenone and 2,5-dichlorobenzaldehyde for 4-methylbenzaldehyde in EXAMPLE 1. $^1$H NMR (300 MHz, DMSO-$d_6$) δ 7.75 (d, 1H), 7.63 (d, 1H), 7.53 (m, 2H), 7.36 (d, 1H), 7.24 (dd, 1H), 7.18 (dd, 1H), 7.07 (brs, 2H), 6.76 (m, 2H), 2.20 (s, 3H).

EXAMPLE 39A

This compound was made by substituting 1-butaneboronic acid for 4-chlorobenzeneboronic acid in EXAMPLE 34B.

EXAMPLE 39B

This compound was made by substituting EXAMPLE 39A for 5-bromo-2-hydroxyacetophenone and 2,5-dichlorobenzaldehyde for 4-methylbenzaldehyde in EXAMPLE 1. $^1$H NMR (300 MHz, DMSO-d$_6$) δ 7.73 (m, 2H), 7.64 (dd, 1H), 7.42 (brs, 1H), 7.18 (dd, 1H), 6.91 (d, 1H), 6.67 (brs, 1H), 2.50 (t, 2H), 1.52 (m, 2H), 1.30 (m, 2H), 0.88 (t, 3H).

EXAMPLE 40A

This compound was made by substituting 4-pyridylboronic acid for 4-chlorobenzeneboronic acid in EXAMPLE 34B.

EXAMPLE 40B

This compound was made by substituting EXAMPLE 40A for 5-bromo-2-hydroxyacetophenone and 2,5-dichlorobenzaldehyde for 4-methylbenzaldehyde in EXAMPLE 1. $^1$H NMR (300 MHz, DMSO-d$_6$) δ 8.46 (d, 2H), 8.22 (d, 1H), 7.72 (d, 2H), 7.64 (m, 2H), 7.59 (s, 1H), 7.57 (dd, 1H), 7.09 (brs, 2H), 7.03 (s, 1H), 6.75 (d, 1H).

EXAMPLE 41A

This compound was made by substituting 4-trifluoro-methylbenzeneboronic acid for 4-chlorobenzeneboronic acid in EXAMPLE 34B.

EXAMPLE 41B

This compound was made by substituting EXAMPLE 41A for 5-bromo-2-hydroxyacetophenone and 2,5-dichlorobenzaldehyde for 4-methylbenzaldehyde in EXAMPLE 1. $^1$H NMR (300 MHz, DMSO-d$_6$) δ 8.13 (d, 1H), 7.90 (m, 2H), 7.64 (m, 2H), 7.61 (d, 2H), 7.58 (s, 1H), 7.56 (m, 2H), 7.07 (brs, 2H), 6.97 (s, 1H), 6.77 (d, 1H).

EXAMPLE 42A

This compound was made by substituting 3-cyanobenzeneboronic acid for 4-chlorobenzeneboronic acid in EXAMPLE 34B.

EXAMPLE 42B

This compound was made by substituting EXAMPLE 42A for 5-bromo-2-hydroxyacetophenone and 2,5-dichlorobenzaldehyde for 4-methylbenzaldehyde in EXAMPLE 1. $^1$H NMR (300 MHz, DMSO-d$_6$) δ 8.16 (dd, 1H), 8.13 (d, 1H), 8.00 (dd, 1H), 7.67 (m, 1H), 7.64 (dd, 1H), 7.61 (m, 1H), 7.58 (s, 1H), 7.55 (m, 2H), 7.27 (brs, 1H), 7.02 (s, 1H), 6.77 (d, 1H).

EXAMPLE 43A

A solution of 4-cyclopentylphenol (1.62 g), acetyl chloride (906 µL), and pyridine (0.97 mL) in dichloromethane (35 mL) was stirred for 24 hours, treated with hexanes (50 mL) and filtered through silica gel.

EXAMPLE 43B

A solution of EXAMPLE 43A (1.23 g) and ZrCl$_4$ (5.6 g) in dichloromethane (40 mL) was stirred for 72 hours, quenched with water and extracted with ethyl acetate. The extract was washed with brine and dried (Na$_2$SO$_4$), filtered and concentrated. The concentrate was flash chromatographed on silica gel with 25% ethyl acetete/hexanes.

EXAMPLE 43C

This compound was made by substituting EXAMPLE 43B for 5-bromo-2-hydroxyacetophenone and 2,5-dichlorobenzaldehyde for 4-methylbenzaldehyde in EXAMPLE 1. $^1$H NMR (300 MHz, DMSO-d$_6$) δ 7.61 (m, 2H), 7.54 (m, 2H), 7.07 (dd, 1H), 7.05 (brs, 2H), 6.68 (m, 2H), 2.74 (m, 1H), 1.93 (m, 2H), 1.71 (m, 2H), 1.57 (m, 4H).

EXAMPLE 44A

A solution of EXAMPLE 34A (600 mg), cyclopropylacetylene (144 mg), Pd(PhCN)$_2$Cl$_2$ (42 mg), tert-tributylphosphine.HBF$_4$ (69 mg), CuI (14 mg) and diisopropylethylamine (0.30 mL) in dioxane (2 mL) was stirred for 24 hours, poured into 1M HCl (10 mL) and extracted with ethyl acetate. The extract was washed with brine and concentrated. The concentrate was flash chromatographed on silica gel with 25% ethyl acetete/hexanes.

EXAMPLE 44B

This compound was made by substituting EXAMPLE 44A for 5-bromo-2-hydroxyacetophenone and 2,5-dichlorobenzaldehyde for 4-methylbenzaldehyde in EXAMPLE 1. $^1$H NMR (300 MHz, DMSO-d$_6$) δ 7.71 (m, 3H), 7.64 (m, 2H), 7.34 (dd, 1H), 6.75 (brs, 2H), 1.49 (m, 1H), 0.86 (m, 2H), 0.68 (m, 2H).

EXAMPLE 45A

This compound was made by substituting 3-(benzyloxy)phenol for 4-chloro-3-ethylphenol in EXAMPLE 31A.

EXAMPLE 45B

This compound was made by substituting EXAMPLE 45A for 5-bromo-2-hydroxyacetophenone and 2,5-dichlorobenzaldehyde for 4-methylbenzaldehyde in EXAMPLE 1. $^1$H NMR (300 MHz, DMSO-d$_6$) δ 7.62 (m, 2H), 7.55 (m, 2H), 7.43 (m, 3H), 7.34 (m, 2H), 7.09 (brs, 3H), 6.53 (s, 1H), 6.28 (dd, 1H), 6.23 (dd, 1H), 5.07 (s, 2H).

EXAMPLE 46

This compound was made by substituting 1-naphthaldehyde for 4-methylbenzaldehyde in EXAMPLE 1. $^1$H NMR (300 MHz, DMSO-d$_6$) δ 8.07 (d, 1H), 8.05 (d, 1H), 7.82 (d, 1H), 7.75 (d, 1H), 7.64 (dd, 1H), 7.57 (m, 3H), 7.37 (dd, 1H), 6.84 (brs, 1H), 6.81 (d, 1H).

EXAMPLE 47

This compound was made by substituting 2-naphthaldehyde for 4-methylbenzaldehyde in EXAMPLE 1. $^1$H NMR (300 MHz, DMSO-d$_6$) δ 8.31 (d, 1H), 8.10 (d, 1H), 8.07 (d, 1H), 8.03 (d, 1H), 7.83 (brs, 1H), 7.81 (dd, 1H), 7.64 (m, 2H), 7.49 (dd, 1H), 6.96 (s, 1H), 6.93 (s, 1H).

EXAMPLE 48

This compound was made by substituting 5-bromo-2-furaldehyde for 4-methylbenzaldehyde in EXAMPLE 1. $^1$H NMR (300 MHz, DMSO-d$_6$) δ 7.96 (d, 1H), 7.49 (d, 1H), 7.25 (dd, 1H), 7.04 (brs, 2H), 6.95 (s, 1H), 6.86 (d, 1H), 6.61 (d, 1H).

EXAMPLE 49

This compound was made by substituting 4-bromothiophene-2-carboxaldehyde for 4-methylbenzaldehyde in EXAMPLE 1. $^1$H NMR (300 MHz, DMSO-$d_6$) δ 8.05 (d, 1H), 7.92 (d, 1H), 7.82 (d, 1H), 7.26 (dd, 1H), 7.05 (brs, 2H), 6.91 (s, 1H), 6.63 (d, 1H).

EXAMPLE 50

This compound was made by substituting 5-methylthiophene-2-carboxaldehyde for 4-methylbenzaldehyde in EXAMPLE 1. $^1$H NMR (300 MHz, DMSO-$d_6$) δ 7.92 (d, 1H), 7.69 (d, 1H), 7.23 (dd, 1H), 7.07 (brs, 2H), 6.95 (d, 1H), 6.80 (s, 1H), 6.60 (d, 1H), 2.53 (s, 3H).

EXAMPLE 51

This compound was made by substituting 5-bromothiophene-2-carboxaldehyde for 4-methylbenzaldehyde in EXAMPLE 1. $^1$H NMR (300 MHz, DMSO-$d_6$) δ 8.01 (d, 1H), 7.69 (d, 1H), 7.38 (d, 1H), 7.28 (dd, 1H), 7.09 (brs, 2H), 6.88 (s, 1H), 6.65 (d, 1H).

EXAMPLE 52

This compound was made by substituting benzofuran-2-carboxaldehyde for 4-methylbenzaldehyde in EXAMPLE 1. $^1$H NMR (300 MHz, DMSO-$d_6$) δ 8.01 (d, 1H), 7.91 (d, 1H), 7.81 (d, 1H), 7.73 (d, 1H), 7.45 (ddd, 1H), 7.34 (ddd, 1H), 7.29 (dd, 1H), 7.21 (s, 1H), 7.08 (brs, 1H), 6.65 (d, 1H).

EXAMPLE 53

This compound was made by substituting benzothiophene-3-carboxaldehyde for 4-methylbenzaldehyde in EXAMPLE 1. $^1$H NMR (300 MHz, DMSO-$d_6$) δ 8.09 (ddd, 1H), 8.01 (s, 1H), 7.88 (d, 1H), 7.73 (ddd, 1H), 7.45 (m, 2H), 7.23 (dd, 1H), 7.08 (brs, 1H), 6.83 (s, 1H), 6.63 (d, 1H).

EXAMPLE 54

This compound was made by substituting 2,5-dichlorothiophene-3-carboxaldehyde for 4-methylbenzaldehyde in EXAMPLE 1. $^1$H NMR (300 MHz, DMSO-$d_6$) δ 7.85 (d, 1H), 7.38 (s, 1H), 7.37 (dd, 1H), 7.09 (br m, 2H), 6.82 (brs, 2H), 6.79 (d, 1H).

EXAMPLE 55A

A solution of 2-chloro-5-iodobenzoic acid (600 mg) in THF (7 mL) at 0° C. was treated with a 1M LiAlH$_4$ in THF (1.17 mL), stirred for 30 minutes, quenched with water (5 mL), diluted with ethyl acetate, washed with 1M HCl, 1M NaOH and brine and concentrated. The concentrate was flash chromatographed on silica gel with 20% ethyl acetete/hexanes.

EXAMPLE 55B

This compound was made by substituting EXAMPLE 55A for EXAMPLE 7B in EXAMPLE 7C.

EXAMPLE 55C

This compound was made by substituting EXAMPLE 55B for 4-methylbenzaldehyde in EXAMPLE 1. $^1$H NMR (300 MHz, DMSO-$d_6$) δ 7.92 (d, 1H), 7.82 (dd, 1H), 7.76 (d, 1H), 7.39 (d, 1H), 7.24 (dd, 1H), 7.07 (brs, 2H), 6.75 (s, 1H), 6.62 (d, 1H).

EXAMPLE 56

This compound was made by substituting 2-chloro-3-quinolinecarboxaldehyde for 4-methylbenzaldehyde in EXAMPLE 1. $^1$H NMR (300 MHz, DMSO-$d_6$) δ 8.58 (s, 1H), 8.13 (d, 1H), 8.05 (d, 1H), 7.93 (d, 1H), 7.90 (dd, 1H), 7.74 (dd, 1H), 7.25 (dd, 1H), 7.06 (brs, 2H), 6.95 (s, 1H), 6.64 (d, 1H).

EXAMPLE 57A

A solution of 2-chloro-5-iodobenzoic acid (600 mg), phenylboronic acid (285 mg) and PdCl$_2$(dppf) (173 mg) in 3M Na$_2$CO$_3$ (2.83 mL) and dioxane (4.5 mL) at 60° C. was stirred for 4 hours, cooled, acidified with 1M HCl, and extracted with ethyl acetate. The extract was washed with brine and concentrated. The concentrate was flash chromatographed on silica gel with ethyl acetate.

EXAMPLE 57B

This compound was made by substituting EXAMPLE 57A for 2-chloro-5-iodobenzoic acid in EXAMPLE 55A.

EXAMPLE 57C

This compound was made by substituting EXAMPLE 57B for EXAMPLE 7B in EXAMPLE 7C.

EXAMPLE 57D

This compound was made by substituting EXAMPLE 57C for 4-methylbenzaldehyde in EXAMPLE 1. $^1$H NMR (300 MHz, DMSO-$d_6$) δ 7.92 (d, 1H), 7.78 (dd, 1H), 7.76 (d, 2H), 7.72 (d, 1H), 7.68 (d, 1H), 7.49 (dd, 2H), 7.40 (t, 1H), 7.24 (dd, 1H), 7.08 (brs, 2H), 6.82 (s, 1H), 6.63 (d, 1H).

EXAMPLE 58

This compound was made by substituting 5-chloro-3-cyano-2-hydroxyacetophenone for 5-bromo-2-hydroxyacetophenone in EXAMPLE 1. $^1$H NMR (300 MHz, DMSO-$d_6$) δ 8.21 (d, 1H), 7.71 (d, 1H), 7.68 (d, 2H), 7.44 (d, 2H), 7.03 (s, 1H), 2.49 (s, 3H).

EXAMPLE 59

This compound was made by substituting 5-phenyl-2-hydroxyacetophenone for 5-bromo-2-hydroxyacetophenone and 2,5-dichlorobenzaldehyde for 4-methylbenzaldehyde in EXAMPLE 1. $^1$H NMR (300 MHz, DMSO-$d_6$) δ 8.03 (d, 1H), 7.64 (m, 3H), 7.56 (m, 3H), 7.36 (dd, 2H), 7.22 (dd, 1H), 7.07 (brs, 2H), 6.92 (s, 1H), 6.79 (d, 1H).

EXAMPLE 60A

A solution of 5-chloro-2-hydroxyacetophenone (10 g) and N-bromosuccinimide (11.5 g) in acetonitrile (200 mL) was refluxed for 24 hours, cooled and concentrated. The concentrate was mixed with ethyl acetate (200 mL) and filtered. The filtrate was concentrated, and the concentrate was flash chromatographed on silica gel with 5% ethyl acetete/hexanes.

EXAMPLE 60B

This compound was made by substituting 3-bromo-5-chloro-2-hydroxyacetophenone for 5-chloro-2-hydroxyacetophenone in EXAMPLE 67. $^1$H NMR (300 MHz, DMSO-d$_6$) δ 8.20 (s, 1H), 8.19 (s, 2H), 8.13 (d, 1H), 7.80 (d, 1H), 7.45 (brs, 2H), 7.23 (s, 1H).

EXAMPLE 61A

A solution of EXAMPLE 60B (2 g) in methanol (25 mL) and ethyl acetate (25 mL) was treated with 2M trimethylsilyldiazomethane solution (10 mL), stirred for 30 minutes and concentrated. The concentrate was flash chromatographed on silica gel with 20% ethyl acetete/hexanes.

EXAMPLE 61B

A solution of EXAMPLE 61A (250 mg), 1-(tert-butyldimethylsiloxy)-1-methoxyethene (0.410 mL), CuF$_2$ (95 mg), PdCl$_2$ (4 mg) and P(o-tolyl)$_3$ (14 mg) in THF (5 mL) was refluxed for 48 hours, cooled and concentrated. The concentrate was flash chromatographed on silica gel with 5% ethyl acetate/hexanes.

EXAMPLE 61C

A solution of EXAMPLE 61B (220 mg) in dichloromethane (20 mL), was treated with 1M BBr$_3$ in dichloromethane (5 mL), stirred for 2 hours, poured into water (30 mL) and extracted with ethyl acetate. The extract was washed with brine and concentrated. The concentrate was flash chromatographed on silica gel with 89% ethyl acetate/10% methanol/1% acetic acid. $^1$H NMR (300 MHz, DMSO-d$_6$) δ 7.89 (m, 4H), 7.70 (s, 2H), 7.18 (d, 1H), 6.96 (s, 1H), 3.49 (s, 2H).

EXAMPLE 62A

A solution of 5-chloro-2-hydroxyacetophenone (4.6 g), 2-chloro-5-trifluoromethylbenzaldehyde (3.92 mL) and NaOH (1.3 g) in diethyl ether (50 mL) and water (25 mL) was stirred for 72 hours, poured into 1M HCl (100 mL) and extracted with diethyl ether. The extract was washed with brine, concentrated and recrystallized from diethyl ether/hexane.

EXAMPLE 62B

A solution of EXAMPLE 62A (120 mg), 2-(1-benzotriazolyl)acetamide (58 mg), and NaOH (46 mg) in ethanol (3 mL) was refluxed for 5 hours, cooled, poured into 1M HCl (10 mL) and extracted with ethyl acetate. The extract was washed with water and brine and concentrated. The concentrate was flash chromatographed on silica gel with 50% ethyl acetate/hexanes. $^1$H NMR (300 MHz, DMSO-d$_6$) δ 7.87 (m, 5H), 7.31 (dd, 1H), 6.95 (d, 1H), 6.66 (brs, 1H).

EXAMPLE 63

This compound was made by substituting 2-(1-benzotriazolyl)propionamide for 2-(1-benzotriazolyl)acetamide in EXAMPLE 62B. $^1$H NMR (300 MHz, DMSO-d$_6$) δ 7.86 (s, 3H), 7.79 (s, 1H), 7.55 (brs, 1H), 7.27 (dd, 1H), 6.94 (d, 1H), 1.83 (brs, 3H).

EXAMPLE 64A

This compound was made by substituting 3,5-dichloro-2-hydroxyacetophenone for 5-chloro-2-hydroxyacetophenone and 4-methylbenzaldehyde for 2-chloro-5-trifluoromethylbenzaldehyde in EXAMPLE 62A.

EXAMPLE 64B

A solution of EXAMPLE 64A (921 mg), cyanoacetamide (277 mg), and potassiun tert-butoxide (1.01 mg) in DMSO (7 mL) at 90° C. was stirred for 4 hours, cooled, poured into 4M HCl (10 mL) and filtered. $^1$H NMR (300 MHz, DMSO-d$_6$) δ 8.29 (d, 1H), 7.95 (s, 1H), 7.85 (d, 2H), 7.58 (s, 1H), 7.35 (d, 2H), 6.99 (s, 1H), 2.39 (s, 3H).

EXAMPLE 65

A solution of EXAMPLE 64B (80 mg) and NBS (45 mg) in DMF (2 mL) and acetic acid (2 mL) was stirred for 24 hours and concentrated. The concentrate was flash chromatographed on silica gel with 50% ethyl acetete/hexanes followed by 0-5% methanol/ethyl acetate. $^1$H NMR (300 MHz, DMSO-d$_6$) δ 7.59 (d, 1H), 7.44 (d, 1H), 7.31 (m, 3H), 7.09 (d, 2H), 2.37 (s, 3H).

EXAMPLE 66

This compound was made by substituting NCS for NBS in EXAMPLE 65. $^1$H NMR (300 MHz, DMSO-d$_6$) δ 7.69 (d, 1H), 7.53 (d, 1H), 7.45 (d, 2H), 7.35 (m, 3H), 2.38 (s, 3H).

EXAMPLE 67

A solution of 5-chloro-2-hydroxyacetophenone (25 g), 2-chloro-5-trifluoromethylbenzaldehyde (30.5 g), ethyl cyanoacetate (15.5 mL) and ammonium acetate (56 g) in ethanol (500 mL) was refluxed for 3 hours, cooled, poured into water and ethyl acetate and stirred for 24 hours. The extract was washed with brine, concentrated to 250 mL and filtered. $^1$H NMR (300 MHz, DMSO-d$_6$) δ 8.00 (brs, 1H), 7.94 (s, 1H), 7.93 (s, 1H), 7.68 (m, 2H), 7.40 (dd, 1H), 6.99 (d, 1H).

EXAMPLE 68

A solution of EXAMPLE 67 (1.9 g) and N-iodosuccinimide (1.06 g) in acetonitrile (30 mL) was refluxed for 24 hours, cooled and concentrated. The concentrate was flash chromatographed on silica gel with ethyl acetate. $^1$H NMR (300 MHz, DMSO-d$_6$) δ 8.02 (brs, 1H), 7.96 (s, 1H), 7.93 (s, 2H), 7.82 (d, 1H), 7.42 (brs, 1H).

EXAMPLE 69

A solution of EXAMPLE 68 (95 mg), acrylic acid (0.014 mL), tert-tributylphosphine-HBF$_4$ (5 mg), PdCl$_2$ (2 mg) and triethylamine (0.096 mL) in DMF (3 mL) was stirred at 55° C. for 24 hours, cooled and concantrated. The concentrate was flash chromatographed on silica gel with 1% acetic acid/ethyl acetate. $^1$H NMR (300 MHz, DMSO-d$_6$) δ 12.1 (s, 1H), 7.93 (m, 5H), 7.81 (d, 1H), 7.62 (brs, 2H), 7.14 (brs, 1H), 6.76 (d, 1H).

EXAMPLE 70

This compound was made by substituting N-Boc-allylamine for acrylic acid in EXAMPLE 69. $^1$H NMR (300 MHz, DMSO-d$_6$) δ 7.95 (s, 1H), 7.89 (s, 3H), 7.76 (d, 1H), 7.37 (m, 1H), 7.23 (d, 1H), 7.18 (dd, 1H), 7.05 (brs, 1H), 6.74 (d, 1H), 6.31 (dt, 1H), 3.72 (t, 2H), 1.41 (s, 9H).

EXAMPLE 71

A solution of EXAMPLE 68 (620 mg), N-Boc-propargylamine (262 mg), Pd(PPh$_3$)$_4$ (127 mg), and CuI (21 mg) in piperidine (8 mL) at 80° C. was stirred for 3 hours, cooled, poured into 1M HCl (100 mL) and extracted with ethyl acetate. The extract was washed with 1M HCl and brine and concentrated. The concentrate was flash chromatographed on silica gel with 50% ethyl acetete/hexanes. $^1$H NMR (300 MHz, DMSO-d$_6$) δ 8.08 (s, 1H), 7.96 (s, 3H), 7.89 (d, 1H), 7.84 (brs, 1H), 7.47 (m, 2H), 6.80 (s, 1H), 4.31 (d, 2H).

EXAMPLE 72

A solution of EXAMPLE 71 (80 mg) in TFA (8 mL) and triethylsilane (1 mL) was stirred for 1 hour and concentrated. The concentrate was purified by reverse-phase HPLC with 0.01M HCl/CH$_3$CN. $^1$H NMR (300 MHz, DMSO-d$_6$) δ 8.53 (brs, 2H), 8.08 (s, 1H), 8.02 (d, 1H), 7.97 (s, 3H), 7.33 (brs, 1H), 7.14 (s, 1H), 6.99 (brs, 1H), 4.31 (d, 2H).

EXAMPLE 73

A solution of EXAMPLE 68 (12 g), palladium acetate (125 mg), diphenylphosphinoferrocene (600 mg), triethylamine (7.6 mL) and triethylsilane (11 mL) in DMF (225 mL) at 75° C. was stirred under CO (balloon) for 24 hours, cooled, poured into water and extracted with ethyl acetate. The extract was washed with water and brine and dried (Na$_2$SO$_4$), filtered and concentrated. The concentrate was taken up in a minimal amount of warm ethyl acetate, triturated with diethyl ether and filtered. $^1$H NMR (300 MHz, DMSO-d$_6$) δ 10.33 (s, 1H), 8.12 (brs, 1H), 7.93 (s, 1H), 7.90 (s, 2H), 7.43 (d, 1H), 7.03 (brs, 1H).

EXAMPLE 74

A solution of EXAMPLE 73 (100 mg) in methanol (25 mL) was treated with NaBH$_4$ (50 mg), stirred for 1 hour and concentrated. The concentrate and taken up in water and extracted with ethyl acetate. The extract was washed with brine and dried (Na$_2$SO$_4$), filtered and concentrated. $^1$H NMR (300 MHz, DMSO-d$_6$) δ 8.07 (s, 1H), 8.02 (s, 2H), 7.99 (m, 2H), 7.58 (m, 1H), 7.53 (brs, 1H), 4.65 (s, 2H).

EXAMPLE 75

A solution of EXAMPLE 68 (551 mg), palladium acetate (22 mg), 1,3-bis(diphenylphosphino)propane (41 mg), triethylamine (0.538 mL), and n-butanol (0.274 mL) in DMSO (4 mL) at 75° C. was stirred under CO (balloon) for 24 hours, treated with water (25 mL) and extracted with ethyl acetate. The extract was washed with water and brine and dried (Na$_2$SO$_4$), filtered and concentrated. The concentrate was flash chromatographed on silica gel with 10% methanol in ethyl acetate. $^1$H NMR (300 MHz, DMSO-d$_6$) δ 8.02 (s, 1H), 7.89 (m, 4H), 7.51 (s, 1H), 6.96 (s, 1H), 4.65 (s, 2H), 4.18 (t, 2H), 1.66 (m, 2H), 1.43 (m, 2H), 0.93 (t, 3H).

EXAMPLE 76

A solution of EXAMPLE 73 (3 g), Ag$_2$O (1.35 g), and NaOH (1.6 g) in water (60 mL) and tert-butanol (40 mL) at 70° C. was stirred for 24 hours, cooled and poured into water (100 mL) and ethyl acetate (250 mL). The extract was washed with brine and concentrated. The concentrate was flash chromatographed on silica gel with 89% ethyl acetate/10% methanol/1% acetic acid. $^1$H NMR (300 MHz, DMSO-d$_6$) δ 7.99 (brs, 1H), 7.81-7.90 (m, 4H), 7.64 (m, 2H), 7.09 (brs, 1H).

EXAMPLE 77

A solution of EXAMPLE 76 (80 mg), 4-benzylpiperidine (0.030 mL), EDCI (130 mg) and DMAP (10 mg) in dichloromethane (4 mL) was stirred for 24 hours and concentrated. The concentrate was flash chromatographed on silica gel with 5% methanol/1% acetic acid/94% ethyl acetate. $^1$H NMR (300 MHz, DMSO-d$_6$) δ 7.87 (s, 3H), 7.83 (d, 1H), 7.27 (d, 2H), 7.19 (m, 3H), 7.00 (brs, 1H), 6.87 (s, 1H), 4.45 (d, 2H), 3.44 (d, 2H), 3.00 (m, 2H), 2.57 (m, 3H), 1.80 (m, 2H), 1.60 (m, 1H), 1.48 (m, 1H).

EXAMPLE 78

This compound was made by substituting N-Boc-1,2-diaminoethane for 4-benzylpiperidine in EXAMPLE 77. $^1$H NMR (300 MHz, DMSO-d$_6$) δ 7.98 (d, 1H), 7.90 (m, 3H), 7.71 (m, 2H), 7.53 (m, 3H), 7.02 (s, 1H), 3.37 (dt, 2H), 3.10 (dt, 2H), 0.93 (s, 9H).

EXAMPLE 79

This compound was made by substituting 4-carboxamidopiperidine for 4-benzylpiperidine in EXAMPLE 77. $^1$H NMR (300 MHz, DMSO-d$_6$) δ 8.95 (brs, 1H), 7.88 (m, 5H), 7.26 (s, 1H), 7.03 (s, 1H), 6.88 (s, 1H), 6.77 (s, 1H), 4.45 (d, 1H), 3.50 (m, 1H), 2.73 (m, 2H), 2.31 (m, 1H), 1.76 (m, 1H), 1.62 (m, 1H), 1.45 (m, 2H).

EXAMPLE 80

This compound was made by substituting 4-methoxybenzylamine for 4-benzylpiperidine in EXAMPLE 77. $^1$H NMR (300 MHz, DMSO-d$_6$) δ 11.13 (brs, 1H), 8.85 (brs, 1H), 8.00 (s, 1H), 7.90 (m, 4H), 7.29 (d, 2H), 7.03 (s, 1H), 6.92 (d, 2H), 4.46 (d, 2H), 3.74 (s, 3H).

EXAMPLE 81

A solution of EXAMPLE 76 (94 mg), N,N,N'-trimethyl-1,3-propanediamine (70 mg), HOBt.H$_2$O (31 mg), 1.2 mol/g polymer-supported DCC (0.50 g) and diisopropylethylamine (0.104 mL) in DMA (3 mL) at 55° C. was stirred for 24 hours, cooled and filtered. The filtrate was shaken with MP-carbonate resin for 2 hours, filtered and concentrated. The concentrate was purified by reverse-phase HPLC with 0.01M HCl/CH$_3$CN. $^1$H NMR (500 MHz, D$_2$O/pyridine-d$_5$) δ 8.04 (d, 1H), 7.94 (s, 1H), 7.89 (m, 2H), 7.40 (d, 1H), 6.96 (s, 1H), 3.68 (t, 2H), 3.17 (s, 6H), 3.10 (t, 2H), 3.07 (s, 3H), 2.32 (m, 2H).

EXAMPLE 82

This compound was made by substituting 2-(3,4-dimethoxyphenyl)-N-methylethylamine for N,N,N'-trimethyl-1,3-propanediamine in EXAMPLE 81. $^1$H NMR (500 MHz, D$_2$O/pyridine-d$_5$) δ 8.03 (d, 1H), 7.92 (d, 1H), 7.84 (s, 2H), 7.51 (d, 1H), 7.03 (m, 1H), 6.97 (m, 1H), 6.86 (d, 6H), 6.76 (dd, 2H), 4.05 (t, 1H), 3.99 (s, 1H), 3.82 (s, 3H), 3.81 (s, 3H), 3.40 (s, 1.5H), 3.20 (t, 1H), 3.11 (s, 1.5H), 2.93 (t, 1H).

EXAMPLE 83

This compound was made by substituting 2-(2-pyridyl)-N-methylethylamine for N,N,N'-trimethyl-1,3-propanediamine in EXAMPLE 81. $^1$H NMR (500 MHz, D$_2$O/pyridine-d$_5$) δ 7.94 (m, 2H), 7.86 (m, 3H), 7.50 (m, 1H), 7.18 (m, 2H), 7.00 (m, 2H), 4.18 (t, 1H), 3.99 (s, 1H), 3.41 (t, 1H), 3.34 (s, 1.5H), 3.18 (t, 1H), 3.09 (s, 1.5H).

EXAMPLE 84

This compound was made by substituting N-ethylpiperazine for N,N,N'-trimethyl-1,3-propanediamine in EXAMPLE 81. $^1$H NMR (500 MHz, D$_2$O/pyridine-d$_5$) δ 8.06 (d, 1H), 7.92 (d, 1H), 7.88 (m, 2H), 7.54 (d, 1H), 6.97 (s, 1H), 4.36 (brs, 2H), 3.93 (brs, 2H), 3.55 (brs, 2H), 3.46 (brs, 2H), 3.21 (q, 2H), 1.34 (t, 3H).

EXAMPLE 85

This compound was made by substituting N-(2-pyridyl)piperazine for N,N,N'-trimethyl-1,3-propanediamine in EXAMPLE 81. $^1$H NMR (500 MHz, D$_2$O/pyridine-d$_5$) δ 8.38 (d, 1H), 8.10 (d, 1H), 7.96 (d, 1H), 7.88 (m, 2H), 7.63 (m, 2H), 7.09 (s, 1H), 6.83 (d, 1H), 6.74 (dd, 1H), 4.11 (brs, 2H), 3.54 (brs, 2H), 3.71 (brs, 4H).

EXAMPLE 86

This compound was made by substituting 1-(2-(2-hydroxyethoxy)ethyl)piperazine for N,N,N'-trimethyl-1,3-propanediamine in EXAMPLE 81. $^1$H NMR (500 MHz, D$_2$O/pyridine-d$_5$) δ 8.06 (d, 1H), 7.94 (d, 1H), 7.88 (m, 2H), 7.53 (d, 1H), 6.99 (s, 1H), 4.26 (brs, 2H), 3.98 (t, 2H), 3.88 (t, 2H), 3.84 (brs, 2H), 3.75 (t, 2H), 3.31 (brs, 2H), 3.26 (brs, 2H), 3.21 (t, 2H).

EXAMPLE 87

This compound was made by substituting N-(4-fluorophenyl)piperazine for N,N,N'-trimethyl-1,3-propanediamine in EXAMPLE 81. $^1$H NMR (500 MHz, D$_2$O/pyridine-d$_5$) δ 8.10 (d, 1H), 7.95 (d, 1H), 7.87 (m, 2H), 7.64 (d, 1H), 7.17 (dd, 2H), 7.04 (m, 2H), 4.19 (brs, 2H), 3.77 (brs, 2H), 3.23 (brs, 4H).

EXAMPLE 88

This compound was made by substituting N-methylhomopiperazine for N,N,N'-trimethyl-1,3-propanediamine in EXAMPLE 81. $^1$H NMR (500 MHz, D$_2$O/pyridine-d$_5$) δ 8.05 (d, 1H), 7.93 (m, 3H), 7.54 (d, 1H), 6.97 (s, 1H), 3.89 (m, 2H), 3.59 (m, 2H), 3.37 (d, 1H), 3.22 (d, 1H), 3.14 (d, 1H), 2.35 (m, 6H).

EXAMPLE 89

A solution of EXAMPLE 73 (4.22 g), methylamine hydrochloride (1.26 g), sodium triacetoxyborohydride (4.93 g) and triethylamine (2.6 mL) in 1,2-dichloroethane (80 mL) was stirred for 24 hours, poured into water (100 mL) and ethyl acetate (200 mL), stirred at 50° C., cooled, and filtered with ethanol and diethyl ether. $^1$H NMR (300 MHz, DMSO-d$_6$) δ 8.63 (brs, 1H), 7.90 (s, 3H), 7.52 (s, 1H), 7.28 (d, 1H), 6.99 (s, 1H), 4.02 (m, 2H), 2.54 (d, 3H).

EXAMPLE 90

This compound was made by substituting 4-benzylpiperidine for methylamine.HCl in EXAMPLE 89. $^1$H NMR (300 MHz, DMSO-d$_6$) δ 7.87 (s, 3H), 7.84 (s, 1H), 7.77 (brs, 1H), 7.28 (m, 1H), 7.18 (m, 5H), 6.84 (brs, 1H), 3.60 (m, 2H), 2.95 (m, 2H), 1.59 (m, 4H), 1.28 (m, 5H).

EXAMPLE 91

This compound was made by substituting 4-benzylpiperazine for methylamine.HCl in EXAMPLE 89. $^1$H NMR (300 MHz, DMSO-d$_6$) δ 7.86 (m, 3H), 7.82 (s, 1H), 7.71 (d, 1H), 7.30 (m, 5H), 7.25 (m, 1H), 7.17 (d, 1H), 6.79 (s, 1H), 3.47 (m, 4H), 3.32 (m, 2H), 2.69 (m, 4H), 2.40 (brs, 2H).

EXAMPLE 92

A solution of EXAMPLE 89 (425 mg), Boc-isonipecotic acid (260 mg), HOBt.H$_2$O (138 mg), 1.2 mol/g polymer-supported DCC (2.26 g) and diisopropylethylamine (0.474 mL) in DMA (8 mL) was stirred for 18 hours and filtered. The filtrant was flash chromatographed on silica gel with 89% ethyl acetate/10% methanol/1% acetic acid. $^1$H NMR (300 MHz, DMSO-d$_6$) δ 7.87 (m, 3H), 7.74 (dd, 1H), 7.23 (d, 1H), 7.17 (dd, 1H), 6.85 (d, 1H), 6.82 (dd, 1H), 4.52 (s, 0.5H), 4.42 (s, 1.5H), 3.94 (m, 2H), 3.07 (s, 2.25H), 2.82 (m, 3H), 2.81 (s, 0.75H), 1.44-1.66 (m, 4H), 1.40 (s, 9H).

EXAMPLE 93

A solution of EXAMPLE 92 (580 mg) in dioxane (40 mL) and 4M HCl (40 mL) was stirred for 1 hour and concentrated. The concentrated was crystallized from toluene/methanol as the HCl salt. $^1$H NMR (300 MHz, DMSO-d$_6$) δ 7.97 (m, 3H), 7.71 (d, 1H), 7.54 (dd, 1H), 7.41 (dd, 1H), 7.24 (d, 1H), 7.16 (m, 2H), 4.55 (s, 0.5H), 4.51 (s, 1.5H), 3.27 (m, 2H), 3.12 (s, 2.25H), 3.07 (m, 2H), 2.94 (m, 2H), 2.86 (s, 0.75H), 2.55 (t, 1H), 1.84 (m, 2H).

EXAMPLE 94

This compound was made by substituting 1-acetylpiperidine-4-carboxylic acid for Boc-isonipecotic acid in EXAMPLE 92. $^1$H NMR (300 MHz, DMSO-d$_6$) δ 8.00 (s, 1H), 7.95 (m, 4H), 7.75 (d, 1H), 7.34 (s, 1H), 7.14 (d, 1H), 4.54 (s, 0.5H), 4.50 (s, 1.5H), 4.36 (m, 1H), 3.83 (m, 1H), 3.14 (s, 2.25H), 3.11 (m, 1H), 3.01 (m, 1H), 2.87 (s, 0.75H), 2.64 (t, 1H), 2.01 (s, 3H), 1.73 (m, 2H), 1.55 (m, 1H), 1.35 (m, 1H).

EXAMPLE 95

A solution of EXAMPLE 89 (94 mg), nicotinic acid (31 mg), HOBt.H$_2$O (31 mg), 1.2 mol/g polymer-supported DCC (0.50 g) and diisopropylethylamine (0.104 mL) in DMA (3 mL) at 55° C. was stirred for 24 hours and filtered. The filtrate was shaken with MP-carbonate resin for 2 hours and filtered. The filtrate was concentrated, and the concentrate was purified by reverse-phase HPLC with 0.01M HCl/CH$_3$CN. $^1$H NMR (500 MHz, D$_2$O/DMSO-d$_6$) δ 8.73 (m, 2H), 8.33 (d, 1H), 7.95 (m, 4H), 7.82 (d, 1H), 7.37 (d, 1H), 7.30 (brs, 1H), 4.73 (s, 0.5H), 4.56 (s, 1.5H), 4.12 (s, 2H), 3.19 (s, 2.25H), 2.86 (s, 0.75H).

EXAMPLE 96

This compound was made by substituting (5-methyl-1-phenylpyrazole-4-carboxylic acid for nicotinic acid in EXAMPLE 95. $^1$H NMR (500 MHz, $D_2O$/DMSO-$d_6$) δ 8.00 (s, 1H), 7.95 (m, 3H), 7.78 (m, 2H), 7.58 (d, 2H), 7.52 (m, 3H), 7.13 (brs, 1H), 4.68 (brs, 2H), 3.20 (brs, 3H), 2.38 (s, 3H).

EXAMPLE 97

This compound was made by substituting thiazole-4-carboxylic acid for nicotinic acid in EXAMPLE 95. $^1$H NMR (500 MHz, $D_2O$/DMSO-$d_6$) δ 9.16 (d, 1H), 8.27 (d, 1H), 7.95 (m, 3H), 7.86 (d, 1H), 7.44 (brs, 1H), 7.27 (brs, 1H), 4.85 (s, 0.67H), 4.71 (s, 1.33H), 3.22 (s, 2H), 2.96 (s, 1H).

EXAMPLE 98

This compound was made by substituting 3-furoic acid for nicotinic acid in EXAMPLE 95. $^1$H NMR (500 MHz, $D_2O$/DMSO-$d_6$) δ 8.23 (s, 1H), 8.00 (s, 1H), 7.95 (m, 2H), 7.76 (d, 1H), 7.44 (brs, 1H), 7.15 (brs, 1H), 6.82 (s, 1H), 4.65 (brs, 2H), 3.22 (s, 2.5H), 2.96 (s, 0.5H).

EXAMPLE 99

This compound was made by substituting indole-3-carboxylic acid for nicotinic acid in EXAMPLE 95. $^1$H NMR (500 MHz, $D_2O$/DMSO-$d_6$) δ 8.01 (s, 1H), 7.95 (m, 4H), 7.88 (d, 1H), 7.74 (brs, 1H), 7.54 (brs, 1H), 7.49 (d, 1H), 7.23 (dd, 1H), 7.17 (dd, 1H), 7.02 (brs, 1H), 4.71 (brs, 2H), 3.24 (s, 3H).

EXAMPLE 100

This compound was made by substituting 4-oxo-4,5,6,7-tetrahydrobenzo[b]furan-3-carboxylic acid for nicotinic acid in EXAMPLE 95. $^1$H NMR (500 MHz, $D_2O$/DMSO-$d_6$) δ 7.96 (m, 4H), 7.85 (d, 1H), 7.70 (d, 1H), 7.38 (brs, 1H), 4.67 (brs, 2H), 2.94 (m, 2H), 2.87 (s, 3H), 2.48 (m, 2H), 2.13 (m, 2H).

EXAMPLE 101

This compound was made by substituting 6-chloro-2H-1-benzopyran-3-carboxylic acid for nicotinic acid in EXAMPLE 95. $^1$H NMR (500 MHz, $D_2O$/DMSO-$d_6$) δ 7.96 (m, 4H), 7.88 (brs, 1H), 7.43 (s, 1H), 7.30 (m, 2H), 6.90 (m, 2H), 4.89 (s, 2H), 4.61 (brs, 2H), 3.18 (br s, 2H), 2.84 (brs, 1H).

EXAMPLE 102

This compound was made by substituting 4-methoxybenzoic acid for nicotinic acid in EXAMPLE 95. $^1$H NMR (500 MHz, $D_2O$/DMSO-$d_6$) δ 7.95 (m, 4H), 7.80 (brs, 1H), 7.51 (brs, 2H), 7.15 (m, 1H), 7.02 (brs, 1H), 4.64 (brs, 2H), 3.80 (s, 3H), 3.03 (brs, 3H).

EXAMPLE 103

This compound was made by substituting 2-chlorobenzoic acid for nicotinic acid in EXAMPLE 95. $^1$H NMR (500 MHz, $D_2O$/DMSO-$d_6$) δ 7.95 (m, 4H), 7.56 (d, 1H), 7.37-7.51 (m, 5H), 4.75 (brs, 1.33H), 4.39 (s, 0.67H), 3.03 (s, 1H), 2.96 (s, 2H).

EXAMPLE 104

This compound was made by substituting (4-methylpiperazin-1-yl)acetic acid for nicotinic acid in EXAMPLE 95. $^1$H NMR (500 MHz, $D_2O$/DMSO-$d_6$) δ 7.99 (s, 1H), 7.96 (m, 2H), 7.86 (d, 1H), 7.37 (brs, 1H), 7.32 (d, 1H), 4.55 (s, 2H), 4.39 (s, 0.67H), 3.91 (brs, 2H), 3.33 (brs, 4H), 3.18 (m, 4H), 3.05 (s, 3H).

EXAMPLE 105

This compound was made by substituting 3-ethoxypropionic acid for nicotinic acid in EXAMPLE 95. $^1$H NMR (500 MHz, $D_2O$/DMSO-$d_6$) δ 7.99 (s, 1H), 7.94 (m, 2H), 7.75 (s, 1H), 7.33 (s, 1H), 7.12 (d, 1H), 4.59 (s, 0.5H), 4.50 (s, 1.5H), 3.64 (t, 2H), 3.44 (q, 2H), 3.07 (s, 2.25H), 2.84 (s, 0.75H), 2.67 (t, 2H), 1.08 (t, 3H).

EXAMPLE 106

This compound was made by substituting 1-aminocarbonyl-1-cyclopropanecarboxylic acid for nicotinic acid in EXAMPLE 95. $^1$H NMR (500 MHz, $D_2O$/DMSO-$d_6$) δ 7.99 (s, 1H), 7.95 (m, 2H), 7.80 (s, 1H), 7.51 (s, 1H), 7.28 (d, 1H), 4.52 (s, 2H), 3.03 (s, 3H), 1.34 (m, 2H), 1.18 (m, 2H).

EXAMPLE 107

This compound was made by substituting 2-(benzyloxy)acetic acid for nicotinic acid in EXAMPLE 95. $^1$H NMR (500 MHz, $D_2O$/DMSO-$d_6$) δ 7.99 (s, 1H), 7.95 (m, 2H), 7.80 (s, 1H), 7.36 (m, 4H), 7.30 (m, 2H), 7.19 (d, 1H), 4.55 (s, 2H), 4.51 (s, 2H), 4.33 (s, 2H), 3.06 (s, 3H).

EXAMPLE 108

This compound was made by substituting 4-methoxycyclohexanecarboxylic acid for nicotinic acid in EXAMPLE 95. $^1$H NMR (500 MHz, $D_2O$/DMSO-$d_6$) δ 7.99 (s, 1H), 7.94 (m, 2H), 7.73 (s, 1H), 7.33 (d, 1H), 7.08 (m, 1H), 4.47 (s, 2H), 3.41 (m, 1H), 3.24 (s, 1.5H), 3.20 (s, 1.5H), 3.10 (s, 3H), 2.72 (m, 0.5H), 2.64 (m, 0.5H), 2.05 (m, 1H), 1.85 (m, 1H), 1.63 (m, 1H), 1.61 (m, 1H), 1.46 (m, 4H).

EXAMPLE 109

This compound was made by substituting 4-phenylbutanoic acid for nicotinic acid in EXAMPLE 95. $^1$H NMR (500 MHz, $D_2O$/DMSO-$d_6$) δ 7.98 (s, 1H), 7.94 (m, 2H), 7.73 (s, 1H), 7.38 (s, 1H), 7.28 (dd, 2H), 7.20 (d, 2H), 7.14 (t, 1H), 7.07 (brs, 1H), 4.49 (s, 2H), 3.02 (s, 3H), 2.64 (t, 2H), 2.43 (t, 2H), 1.83 (m, 2H).

EXAMPLE 110

This compound was made by substituting (4-methylphenoxy)acetic acid for nicotinic acid in EXAMPLE 95. $^1$H NMR (500 MHz, $D_2O$/DMSO-$d_6$) δ 8.00 (s, 1H), 7.95 (m, 2H), 7.79 (d, 1H), 7.27 (s, 1H), 7.07 (m, 3H), 6.84 (d, 2H), 4.89 (s, 2H), 4.53 (s, 2H), 3.08 (s, 3H), 2.22 (s, 3H).

EXAMPLE 111

This compound was made by substituting N-(2-furoyl)glycine for nicotinic acid in EXAMPLE 95. $^1$H NMR (500 MHz, $D_2O$/DMSO-$d_6$) δ 7.99 (s, 1H), 7.94 (m, 2H), 7.83 (s, 1H), 7.79 (s, 1H), 7.33 (s, 1H), 7.21 (d, 1H), 7.14 (d, 1H), 6.66 (d, 1H), 4.53 (s, 2H), 4.20 (s, 2H), 3.10 (s, 3H).

EXAMPLE 112

This compound was made by substituting (2-thienyl)butanoic acid for nicotinic acid in EXAMPLE 95. $^1$H NMR (500 MHz, $D_2O$/DMSO-$d_6$) δ 7.99 (s, 1H), 7.94 (m, 2H), 7.73 (s, 1H), 7.37 (s, 1H), 7.28 (d, 1H), 7.07 (d, 1H), 6.94 (d, 1H), 6.84 (s, 1H), 4.49 (s, 2H), 3.03 (s, 3H), 2.86 (t, 2H), 2.48 (t, 2H), 1.88 (m, 2H).

EXAMPLE 113

This compound was made by substituting 1-pyrrolidinepropanoic acid for Boc-isonipecotic acid in EXAMPLE 92. $^1$H NMR (300 MHz, DMSO-$d_6$) δ 7.98 (m, 5H), 7.83 (d, 1H), 7.34 (s, 1H), 7.28 (d, 1H), 4.61 (0.5H), 4.55 (s, 1.5H), 3.54 (m, 2H), 3.39 (t, 2H), 3.07 (s, 2.25H), 3.06 (m, 2H), 2.92 (t, 2H), 2.87 (s, 0.75H), 2.06 (m, 2H), 1.99 (m, 2H).

EXAMPLE 114

This compound was made by substituting 1-morpholinepropanoic acid for Boc-isonipecotic acid in EXAMPLE 92. $^1$H NMR (300 MHz, DMSO-$d_6$) δ 7.99 (s, 1H), 7.96 (m, 4H), 7.83 (d, 1H), 7.34 (d, 1H), 7.28 (d, 1H), 4.61 (s, 0.5H), 4.55 (s, 1.5H), 3.96 (m, 2H), 3.68 (m, 2H), 3.45 (m, 2H), 3.40 (t, 2H), 3.12 (m, 2H), 3.08 (s, 2.25H), 2.96 (t, 2H), 2.86 (s, 0.75H).

EXAMPLE 115A

This compound was made by substituting benzylamine for methylamine.HCl in EXAMPLE 89.

EXAMPLE 115B

This compound was made by substituting 1-morpholinepropanoic acid for Boc-isonipecotic acid and EXAMPLE 115A for EXAMPLE 89 in EXAMPLE 92. $^1$H NMR (300 MHz, DMSO-$d_6$) δ 8.04 (s, 1H), 8.01 (s, 7H), 7.62 (br m, 2H), 7.54 (d, 1H), 7.31 (d, 1H), 7.13 (d, 1H), 5.26 (s, 2H), 4.63 (s, 0.5H), 4.59 (s, 1.5H), 3.90 (m, 4H), 3.42 (t, 2H), 3.05 (t, 2H), 1.76 (m, 4H).

EXAMPLE 116A

This compound was made by substituting propylamine for methylamine hydrochloride in EXAMPLE 89.

EXAMPLE 116B

This compound was made by substituting 1-morpholinepropanoic acid for Boc-isonipecotic acid and EXAMPLE 116A for EXAMPLE 89 in EXAMPLE 92. $^1$H NMR (300 MHz, DMSO-$d_6$) δ 7.96 (s, 1H), 7.92 (m, 3H), 7.83 (d, 1H), 7.25 (m, 1H), 7.21 (s, 1H), 7.10 (d, 1H), 4.51 (s, 2H), 3.87 (m, 4H), 3.35 (m, 4H), 3.22 (m, 6H), 3.08 (m, 2H), 1.81 (m, 2H), 1.18 (t, 3H).

EXAMPLE 117A

A solution of methyl N-Boc-isonipecotic acid (1.24 g) in THF (20 mL) at −78° C. was treated with 1.5M LDA in cyclohexane (4.1 mL), stirred for 30 minutes at 0° C., treated with methyl iodide (0.635 mL), stirred at room temperature for 18 hours and concentrated. The concentrate was flash chromatographed on silica gel with 20% ethyl acetete/hexanes.

EXAMPLE 117B

A solution of EXAMPLE 117A (1.3 g) and LiOH.$H_2O$ (1 g) in THF (40 mL), methanol (15 mL) and water (15 mL) was stirred for 24 hours, poured into $NaH_2PO_4$ solution (100 mL) and extracted with ethyl acetate. The extract was washed with brine, dried ($Na_2SO_4$) and concentrated.

EXAMPLE 117C

This compound was made by substituting EXAMPLE 117B for Boc-isonipecotic acid in EXAMPLE 92. $^1$H NMR (300 MHz, DMSO-$d_6$) δ 8.04 (s, 1H), 8.00 (m, 3H), 7.87 (dd, 1H), 7.35 (br m, 2H), 7.22 (dd, 1H), 4.59 (s, 2H), 3.53 (m, 2H), 3.35 (m, 2H), 3.19 (m, 2H), 3.15 (s, 3H), 2.11 (m, 2H), 1.44 (s, 9H), 1.34 (s, 3H).

EXAMPLE 118

This compound was made by substituting EXAMPLE 117C for EXAMPLE 92 in EXAMPLE 93. $^1$H NMR (300 MHz, DMSO-$d_6$) δ 9.05 (brs, 1H), 8.98 (brs, 1H), 8.02 (s, 1H), 7.95 (m, 3H), 7.40 (br m, 2H), 7.33 (d, 1H), 7.21 (m, 1H), 4.57 (s, 2H), 3.17 (s, 3H), 3.10 (m, 2H), 2.95 (m, 2H), 2.24 (m, 2H), 1.72 (m, 2H), 1.32 (s, 3H).

EXAMPLE 119

This compound was made by substituting Boc-4-phenylpiperidine-4-carboxylic acid for Boc-isonipecotic acid in EXAMPLE 92. $^1$H NMR (300 MHz, DMSO-$d_6$) δ 8.00 (s, 1H), 7.95 (m, 4H), 7.39 (m, 3H), 7.30 (m, 4H), 7.04 (m, 1H), 4.49 (s, 2H), 3.78 (m, 2H), 3.13 (s, 3H), 2.56 (m, 2H), 2.34 (m, 2H), 1.79 (m, 2H), 1.39 (s, 9H).

EXAMPLE 120

This compound was made by substituting EXAMPLE 119 for EXAMPLE 92 in EXAMPLE 93. $^1$H NMR (300 MHz, DMSO-$d_6$) δ 9.04 (brs, 2H), 8.01 (s, 1H), 7.96 (m, 4H), 7.44 (m, 3H), 7.31 (m, 4H), 7.02 (m, 1H), 4.54 (s, 2H), 3.52 (m, 2H), 3.17 (s, 3H), 2.82 (m, 2H), 2.10 (m, 2H), 1.67 (m, 2H).

EXAMPLE 121

This compound was made by substituting 1-(4-pyridinyl)-4-piperidinecarboxylic acid for Boc-isonipecotic acid in EXAMPLE 92. $^1$H NMR (300 MHz, DMSO-$d_6$) δ 8.13 (br m, 2H), 7.90 (s, 1H), 7.87 (m, 3H), 7.85 (dd, 1H), 7.75 (dd, 1H), 6.85 (d, 4H), 4.56 (s, 1H), 4.43 (s, 1H), 4.00 (m, 2H), 3.10 (s, 1.5H), 2.95 (m, 3H), 2.82 (s, 1.5H), 1.75 (m, 1H), 1.64 (m, 3H).

EXAMPLE 122

This compound was made by substituting 1-(4-cyanophenyl)-4-piperidinecarboxylic acid for Boc-isonipecotic acid in EXAMPLE 92. $^1$H NMR (300 MHz, DMSO-$d_6$) δ 7.88 (m, 4H), 7.73 (m, 2H), 7.55 (dd, 2H), 7.02 (dd, 2H), 6.87 (d, 1H), 6.85 (s, 1H), 4.56 (s, 1H), 4.43 (s, 1H), 3.97 (m, 2H), 3.10 (s, 1.5H), 2.96 (m, 3H), 2.82 (s, 1.5H), 1.76 (m, 1H), 1.64 (m, 3H).

EXAMPLE 123

This compound was made by substituting 1-(4-acetylphenyl)-4-piperidinecarboxylic acid for Boc-isonipecotic acid in EXAMPLE 92. $^1$H NMR (300 MHz, DMSO-$d_6$) δ 7.87 (m, 4H), 7.79 (m, 4H), 6.97 (dd, 2H), 6.85 (d, 1H), 6.83 (s, 1H), 4.56 (s, 1H), 4.43 (s, 1H), 3.97 (m, 2H), 3.10 (s, 1.5H), 2.98 (m, 2H), 2.91 (m, 1H), 2.82 (s, 1.5H), 1.76 (m, 1H), 1.64 (m, 3H).

EXAMPLE 124

A solution of EXAMPLE 73 (100 mg), cyclohexanecarboxamide (84 mg), TFA (0.049 mL) and triethylsilane (0.106 mL) in toluene (2 mL) at 100° C. was stirred for 72 hours, cooled and concentrated. The concentrate was flash chromatographed on silica gel with 1% acetic acid/ethyl acetate. $^1$H NMR (300 MHz, DMSO-$d_6$) δ 9.55 (brs, 1H), 8.32 (brs, 1H), 7.97 (s, 1H), 7.93 (m, 3H), 7.82 (brs, 1H), 7.32 (s, 1H), 7.16 (s, 1H), 4.24 (d, 2H), 3.10 (m, 1H), 2.21 (m, 2H), 1.99 (s, 3H), 1.72 (m, 4H), 1.30 (m, 4H).

EXAMPLE 125

This compound was made by substituting benzamide for cyclohexanecarboxamide in EXAMPLE 124. $^1$H NMR (300 MHz, DMSO-$d_6$) δ 9.35 (d, 1H), 8.90 (m, 1H), 7.91 (m, 4H), 7.76 (s, 1H), 7.49 (m, 4H), 7.25 (m, 1H), 7.18 (m, 1H), 6.91 (m, 1H), 4.45 (d, 2H).

EXAMPLE 126

This compound was made by substituting benzyl carbamate for cyclohexanecarboxamide in EXAMPLE 124. $^1$H NMR (300 MHz, DMSO-$d_6$) δ 8.87 (brs, 1H), 7.87 (s, 3H), 7.73 (d, 1H), 7.59 (t, 1H), 7.37 (m, 4H), 7.25 (m, 1H), 7.20 (dd, 1H), 7.02 (s, 1H), 6.89 (s, 1H), 5.07 (s, 2H), 4.18 (d, 2H).

EXAMPLE 127A

A solution of 1-acetylisonipecotoyl chloride (1.5 g) in dioxane (50 mL) was treated with ammonia for 10 minutes, stirred for 18 hours, diluted with diethyl ether, washed with water and brine and dried ($Na_2SO_4$), filtered and concentrated.

EXAMPLE 127B

This compound was made by substituting EXAMPLE 127A for cyclohexanecarboxamide in EXAMPLE 124. $^1$H NMR (300 MHz, DMSO-$d_6$) δ 9.50 (brs, 1H), 8.48 (brs, 1H), 8.01 (s, 1H), 7.95 (s, 3H), 7.85 (brs, 1H), 7.25 (s, 2H), 4.30 (m, 2H), 3.82 (m, 1H), 3.46 (m, 2H), 3.04 (m, 1H), 2.57 (m, 1H), 1.99 (s, 3H), 1.76 (m, 2H), 1.52 (m, 1H), 1.41 (m, 1H).

EXAMPLE 128

A solution of EXAMPLE 89 (67 mg), acetyl chloride (10 μL) and 2,6-lutidine (17 μL) in DMF (1 mL) was stirred for 1 hour and chromatographed on silica gel with 10% methanol/ethyl acetate. $^1$H NMR (300 MHz, DMSO-$d_6$) δ 8.01 (s, 2H), 7.94 (s, 3H), 7.75 (brs, 1H), 7.39 (brs, 1H), 7.16 (d, 1H), 4.55 (s, 0.5H), 4.48 (s, 1.5H), 3.05 (s, 2.25H), 2.80 (s, 0.75H), 2.11 (s, 2.25H), 2.09 (s, 0.75H).

EXAMPLE 129

This compound was made by substituting cyclohexanecarbonyl chloride for acetyl chloride in EXAMPLE 128. $^1$H NMR (300 MHz, DMSO-$d_6$) δ 8.01 (s, 2H), 7.94 (s, 3H), 7.65 (brs, 1H), 7.39 (m, 1H), 7.01 (d, 1H), 4.60 (s, 0.5H), 4.47 (s, 1.5H), 3.10 (s, 2.25H), 2.83 (s, 0.75H), 2.68 (m, 1H), 1.70 (m, 4H), 1.17 (m, 6H).

EXAMPLE 130

This compound was made by substituting benzoyl chloride for acetyl chloride in EXAMPLE 128. $^1$H NMR (300 MHz, DMSO-$d_6$) δ 8.01 (s, 1H), 7.94 (m, 5H), 7.63 (d, 1H), 7.50 (m, 5H), 7.41 (brs, 1H), 7.18 (m, 1H), 4.69 (s, 1.5H), 4.48 (s, 0.5H), 2.96 (s, 2.25H), 2.73 (s, 0.75H).

EXAMPLE 131

A solution of EXAMPLE 93 (57 mg), methoxyacetic acid (13 mg), HOBt.$H_2O$ (19 mg), 1.2 mol/g polymer-supported DCC (304 mg) and diisopropylethylamine (0.063 mL) in DMA (2 mL) was stirred for 18 hours and filtered. The filtrate was taken up in water (25 mL) and extracted with ethyl acetate. The extract was washed with water and concentrated. The concentrate was flash chromatographed on silica gel with 10% methanol/1% acetic acid/89% ethyl acetate. $^1$H NMR (500 MHz, DMSO-$d_6$) δ 7.92 (m, 4H), 7.85 (brs, 1H), 7.75 (d, 1H), 7.13 (brs, 1H), 7.04 (brs, 1H), 4.58 (d, 0.67H), 4.48 (d, 1.33H), 4.33 (m, 1H), 4.11 (m, 1H), 4.04 (m, 1H), 3.29 (s, 3H), 3.12 (s, 2H), 3.01 (m, 2H), 2.82 (s, 1H), 2.69 (m, 1H), 1.75 (m, 2H), 1.61 (m, 1H), 1.52 (m, 1H), 1.40 (m, 1H).

EXAMPLE 132

This compound was made by substituting butanoic acid for methoxyacetic acid in EXAMPLE 131. $^1$H NMR (500 MHz, $D_2O$/pyridine-$d_5$) δ 8.03 (d, 1H), 7.91 (s, 1H), 7.83 (m, 2H), 7.48 (dd, 1H), 6.96 (s, 1H), 5.00 (m, 2H), 4.82 (d, 1H), 3.82 (dd, 1H), 3.30 (m, 0.5H), 3.20 (s, 1.5H), 3.19 (m, 0.5H), 3.11 (s, 1.5H), 3.02 (m, 1H), 2.75 (m, 1H), 2.24 (dt, 2H), 1.77-1.99 (m, 4H), 1.67 (m, 2H), 0.92 (t, 3H).

EXAMPLE 133

This compound was made by substituting 2-methylbutanoic acid for methoxyacetic acid in EXAMPLE 131. $^1$H NMR (500 MHz, $D_2O$/pyridine-$d_5$) δ 8.03 (d, 1H), 7.91 (s, 1H), 7.82 (m, 2H), 7.49 (dd, 1H), 6.98 (d, 1H), 4.99 (m, 2H), 4.79 (d, 1H), 4.02 (dd, 1H), 3.30 (m, 0.5H), 3.21 (s, 1.5H), 3.19 (m, 0.5H), 3.11 (s, 1.5H), 3.03 (m, 1H), 2.82 (m, 1H), 2.66 (m, 1H), 1.86-2.05 (m, 3H), 1.82 (m, 2H), 1.40 (m, 1H), 1.13 (m, 1H), 0.87 (m, 3H).

EXAMPLE 134

This compound was made by substituting 4,4,4-trifluorobutanoic acid for methoxyacetic acid in EXAMPLE 131. $^1$H NMR (500 MHz, $D_2O$/pyridine-$d_5$) δ 8.02 (d, 1H), 7.91 (s, 1H), 7.82 (m, 2H), 7.47 (dd, 1H), 6.98 (d, 1H), 4.99 (m, 2H), 4.77 (d, 1H), 3.83 (dd, 1H), 3.30 (m, 0.5H), 3.20 (s, 1.5H), 3.17 (m, 0.5H), 3.11 (s, 1.5H), 3.02 (m, 1H), 2.75 (m, 1H), 2.58-2.73 (m, 4H), 1.77-1.99 (m, 4H).

EXAMPLE 135

This compound was made by substituting (methylthio)acetic acid for methoxyacetic acid in EXAMPLE 131. $^1$H NMR (500 MHz, $D_2O$/pyridine-$d_5$) δ 8.03 (d, 1H), 7.91 (s, 1H), 7.82 (m, 2H), 7.47 (dd, 1H), 6.98 (d, 1H), 4.99 (m, 2H), 4.75 (d, 1H), 3.95 (dd, 1H), 3.52 (s, 1H), 3.47 (s, 1H), 3.29 (m, 0.5H), 3.20 (s, 1.5H), 3.17 (m, 0.5 H), 3.11 (s, 1.5H), 3.04 (m, 1H), 2.77 (m, 1H), 2.21 (s, 1.5 H), 2.19 (s, 1.5 H), 1.77-1.99 (m, 4H).

EXAMPLE 136

This compound was made by substituting 2-tetrahydrofuroic acid for methoxyacetic acid in EXAMPLE 131. $^1$H NMR (500 MHz, D$_2$O/pyridine-d$_5$) δ 8.03 (d, 1H), 7.92 (s, 1H), 7.83 (m, 2H), 7.48 (dd, 1H), 7.00 (d, 1H), 4.96 (m, 2H), 4.74 (d, 1H), 4.69 (m, 1H), 4.07 (m, 1H), 3.96 (m, 1H), 3.81 (m, 1H), 3.27 (m, 0.5H), 3.19 (s, 1.5H), 3.17 (m, 0.5 H), 3.10 (s, 1.5H), 3.03 (m, 1H), 2.77 (m, 1H), 2.21 (m, 1H), 1.70-1.99 (m, 7H).

EXAMPLE 137

This compound was made by substituting 3-butynoic acid for methoxyacetic acid in EXAMPLE 131. $^1$H NMR (500 MHz, D$_2$O/pyridine-d$_5$) δ 8.03 (d, 1H), 7.92 (s, 1H), 7.82 (m, 2H), 7.48 (dd, 1H), 7.01 (s, 1H), 4.97 (m, 2H), 4.78 (d, 1H), 3.81 (dd, 1H), 3.28 (m, 0.5H), 3.19 (s, 1.5H), 3.14 (m, 0.5 H), 3.10 (s, 1.5H), 3.01 (m, 1H), 2.75 (m, 1H), 2.67 (m, 2H), 2.54 (m, 3H), 1.76-1.99 (m, 4H).

EXAMPLE 138

This compound was made by substituting 3-nitropropanoic acid for methoxyacetic acid in EXAMPLE 131. $^1$H NMR (500 MHz, D$_2$O/pyridine-d$_5$) δ 8.02 (d, 1H), 7.92 (s, 1H), 7.81 (m, 2H), 7.45 (d, 1H), 6.96 (s, 1H), 5.03 (m, 4H), 4.70 (d, 1H), 3.93 (dd, 1H), 3.30 (m, 1H), 3.17 (s, 1.5H), 3.14 (m, 2H), 3.09 (s, 1.5H), 3.02 (m, 1H), 2.72 (m, 1H), 1.75-1.99 (m, 4H).

EXAMPLE 139

This compound was made by substituting cyclopropanecarboxylic acid for methoxyacetic acid in EXAMPLE 131. $^1$H NMR (500 MHz, D$_2$O/pyridine-d$_5$) δ 8.04 (d, 1H), 7.92 (s, 1H), 7.82 (m, 2H), 7.49 (dd, 1H), 7.01 (d, 1H), 4.96 (m, 2H), 4.79 (d, 1H), 4.25 (dd, 1H), 3.31 (m, 0.5H), 3.19 (s, 1.5H), 3.15 (m, 0.5H), 3.10 (s, 1.5H), 3.00 (m, 1H), 2.78 (m, 1H), 1.77-2.02 (m, 5H), 1.09 (m, 2H), 0.71 (m, 2H).

EXAMPLE 140

This compound was made by substituting cyclopropylacetic acid for methoxyacetic acid in EXAMPLE 131. $^1$H NMR (500 MHz, D$_2$O/pyridine-d$_5$) δ 8.04 (d, 1H), 7.92 (s, 1H), 7.82 (m, 2H), 7.49 (dd, 1H), 7.01 (d, 1H), 4.97 (m, 2H), 4.82 (d, 1H), 3.86 (dd, 1H), 3.30 (m, 0.5H), 3.20 (s, 1.5H), 3.15 (m, 0.5H), 3.10 (s, 1.5H), 3.03 (m, 1H), 2.74 (m, 1H), 2.30 (dd, 2H), 1.77-2.02 (m, 4H), 1.14 (m, 1H), 0.51 (m, 2H), 0.25 (m, 2H).

EXAMPLE 141

This compound was made by substituting cyclohexanecarboxylic acid for methoxyacetic acid in EXAMPLE 131. $^1$H NMR (500 MHz, D$_2$O/pyridine-d$_5$) δ 8.04 (d, 1H), 7.92 (s, 1H), 7.82 (m, 2H), 7.50 (d, 1H), 7.01 (d, 1H), 4.97 (m, 2H), 4.86 (d, 1H), 4.02 (dd, 1H), 3.31 (m, 0.5H), 3.21 (s, 1.5H), 3.15 (m, 0.5H), 3.11 (s, 1.5H), 3.04 (m, 1H), 2.76 (m, 1H), 2.60 (m, 1H), 2.03 (m, 1H), 1.92 (m, 2H), 1.78 (m, 3H), 1.65 (m, 4H), 1.56 (m, 1H), 1.25 (m, 2H), 1.12 (m, 1H).

EXAMPLE 142

A solution of EXAMPLE 93 (58 mg) in DMA (0.33 mL) was treated with propanal (70 mg) in dichloromethane (0.17 mL) and methanol (0.17 mL) then with acetic acid (0.03 mL) and 2.5 mol/g MP-cyanoborohydride resin (120 mg), stirred at 50° C. for 24 hours and filtered. The resin was washed with methanol, and the filtrate was concentrated. The concentrate was purified by reverse-phase HPLC with water/CH$_3$CN/ 0.1% TFA. $^1$H NMR (500 MHz, D$_2$O/pyridine-d$_5$) δ 8.05 (d, 1H), 7.90 (s, 1H), 7.85 (m, 2H), 7.42 (d, 1H), 6.98 (s, 1H), 4.95 (m, 2H), 3.87 (dd, 1H), 3.75 (m, 2H), 3.38 (ddd, 2H), 3.18 (s, 1.5H), 3.10 (m, 2H), 3.04 (s, 1.5H), 2.44 (m, 1H), 2.33 (m, 2H), 2.15 (m, 1H), 1.80 (m, 2H), 0.83 (t, 3H).

EXAMPLE 143

This compound was made by substituting phenylacetaldehyde for propanal in EXAMPLE 142. $^1$H NMR (500 MHz, D$_2$O/pyridine-d$_5$) δ 8.04 (d, 1H), 7.90 (s, 1H), 7.83 (m, 2H), 7.44 (d, 1H), 7.37-7.26 (m, 5H), 6.97 (s, 1H), 4.94 (m, 2H), 3.79 (dd, 2H), 3.70 (m, 1H), 3.36 (m, 1H), 3.29 (m, 2H), 3.22 (m, 2H), 3.18 (s, 1.5H), 3.12 (m, 1H), 3.05 (s, 1.5H), 2.49 (d, 1H), 2.29 (d, 2H), 2.09 (d, 1H).

EXAMPLE 144

This compound was made by substituting 2,6,6-trimethyl-1-cyclohexene-1-acetaldehyde for propanal in EXAMPLE 142. $^1$H NMR (500 MHz, D$_2$O/pyridine-d$_5$) δ 8.04 (d, 1H), 7.98 (s, 1H), 7.84 (m, 2H), 7.44 (d, 1H), 6.96 (s, 1H), 4.94 (m, 2H), 3.83 (dd, 2H), 3.36 (m, 2H), 3.21 (s, 1.5H), 3.10 (m, 2H), 3.06 (s, 1.5H), 2.90 (ddd, 1H), 2.65 (m, 1H), 2.49 (m, 2H), 2.20 (m, 1H), 1.82 (m, 2H), 1.66 (d, 3H), 1.48 (m, 3H), 1.35 (m, 3H), 1.02 (s, 3H), 1.01 (s, 3H).

EXAMPLE 145

This compound was made by substituting benzyloxyacetaldehyde for propanal in EXAMPLE 142. $^1$H NMR (500 MHz, D$_2$O/pyridine-d$_5$) δ 8.04 (d, 1H), 7.90 (s, 1H), 7.84 (m, 2H), 7.26-7.44 (m, 6H), 6.97 (d, 1H), 4.98 (s, 1H), 4.90 (d, 1H), 4.57 (d, 2H), 3.89 (dd, 2H), 3.62 (m, 2H), 3.55 (m, 1H), 3.38 (dd, 1H), 3.27 (dd, 1H), 3.17 (s, 1.5H), 3.15 (m, 1H), 3.07 (s, 1.5H), 3.00 (dt, 1H), 2.45 (d, 1H), 2.31 (d, 1H), 2.16 (d, 1H), 2.00 (d, 1H).

EXAMPLE 146

This compound was made by substituting 3-(5-methyl-2-furyl)butyraldehyde for propanal in EXAMPLE 142. $^1$H NMR (500 MHz, D$_2$O/pyridine-d$_5$) δ 8.05 (d, 1H), 7.90 (s, 1H), 7.84 (m, 2H), 7.44 (d, 1H), 6.98 (d, 1H), 6.09 (d, 1H), 6.01 (d, 1H), 4.96 (s, 1H), 4.89 (d, 1H), 3.70 (m, 2H), 3.26 (m, 2H), 3.20 (s, 1.5H), 3.15 (m, 2H), 3.05 (s, 1.5H), 3.02 (m, 1H), 2.92 (m, 1H), 2.47 (m, 2H), 2.30 (m, 2H), 2.21 (s, 3H), 2.15 (m, 2H), 1.25 (d, 3H).

EXAMPLE 147A

This compound was made by substituting EXAMPLE 34C for EXAMPLE 67 in EXAMPLE 68.

EXAMPLE 147B

This compound was made by substituting EXAMPLE 147A for EXAMPLE 68 in EXAMPLE 73.

EXAMPLE 147C

This compound was made by substituting EXAMPLE 147B for EXAMPLE 73 in EXAMPLE 89.

EXAMPLE 147D

This compound was made by substituting EXAMPLE 147C for EXAMPLE 89 and 1-acetylpiperidine-4-carboxylic acid for Boc-isonipecotic acid in EXAMPLE 92. $^1$H NMR (300 MHz, DMSO-$d_6$) δ 7.99 (d, 1H), 7.92 (m, 3H), 7.66 (d, 2H), 7.42 (d, 2H), 7.24 (m, 2H), 7.16 (m, 2H), 4.63 (d, 0.67H), 4.53 (d, 1.33H), 4.35 (dd, 1H), 3.80 (dd, 1H), 3.15 (s, 2H), 3.09 (m, 1H), 2.99 (m, 1H), 2.86 (s, 1H), 2.60 (t, 1H), 1.98 (s, 3H), 1.69 (m, 1H), 1.57 (m, 2H), 1.37 (m, 1H).

EXAMPLE 148

This compound was made by substituting EXAMPLE 147C for EXAMPLE 89 and 1-pyrrolidinepropanoic acid for Boc-isonipecotic acid in EXAMPLE 92. $^1$H NMR (300 MHz, DMSO-$d_6$) δ 7.97 (d, 1H), 7.88 (s, 2H), 7.70 (m, 1H), 7.62 (dd, 1H), 7.39 (d, 2H), 7.25 (m, 2H), 7.18 (m, 2H), 7.01 (d, 1H), 4.51 (d, 1H), 4.14 (d, 1H), 3.75 (m, 2H), 3.44 (m, 2H), 3.05 (s, 1.5H), 2.86 (s, 1.5H), 2.45 (m, 2H), 2.30 (m, 2H), 1.66 (m, 2H), 1.55 (m, 2H).

EXAMPLE 149

This compound was made by substituting EXAMPLE 147C for EXAMPLE 89 and 1-morpholinepropanoic acid for Boc-isonipecotic acid in EXAMPLE 92. $^1$H NMR (300 MHz, DMSO-$d_6$) δ 7.97 (d, 1H), 7.88 (m, 3H), 7.67 (d, 1H), 7.62 (dd, 2H), 7.37 (d, 2H), 7.25 (m, 2H), 7.16 (m, 2H), 7.01 (d, 1H), 4.50 (d, 2H), 3.52 (m, 2H), 3.45 (m, 2H), 3.35 (m, 8H), 3.05 (s, 1.5H), 2.87 (s, 1.5H).

EXAMPLE 150A

This compound was made by substituting EXAMPLE 43B for 5-chloro-2-hydroxyacetophenone in EXAMPLE 67.

EXAMPLE 150B

This compound was made by substituting EXAMPLE 150A for EXAMPLE 67 in EXAMPLE 68.

EXAMPLE 150C

This compound was made by substituting EXAMPLE 150B for EXAMPLE 68 in EXAMPLE 73.

EXAMPLE 150D

This compound was made by substituting EXAMPLE 150C for EXAMPLE 73 in EXAMPLE 89. $^1$H NMR (300 MHz, DMSO-$d_6$) δ 7.88 (m, 3H), 7.64 (d, 1H), 7.16 (d, 1H), 6.84 (s, 1H), 3.97 (s, 2H), 2.81 (m, 1H), 2.49 (s, 3H), 1.90 (m, 2H), 1.75 (m, 2H), 1.56 (m, 4H).

EXAMPLE 151

This compound was made by substituting EXAMPLE 150D for EXAMPLE 89 and 1-acetylpiperidine-4-carboxylic acid for Boc-isonipecotic acid in EXAMPLE 92. $^1$H NMR (300 MHz, DMSO-$d_6$) δ 8.00 (s, 1H), 7.94 (m, 3H), 7.34 (brs, 2H), 6.98 (d, 1H), 6.64 (brs, 1H), 4.65 (s, 0.5H), 4.47 (s, 1.5H), 4.35 (m, 1H), 3.80 (m, 1H), 3.12 (s, 2.25H), 2.94 (m, 3H), 2.83 (s, 0.75H), 2.61 (t, 1H), 1.99 (s, 3H), 1.42-1.75 (m, 12H).

EXAMPLE 152

This compound was made by substituting EXAMPLE 150D for EXAMPLE 89 and 1-pyrrolidinepropanoic acid for Boc-isonipecotic acid in EXAMPLE 92. $^1$H NMR (300 MHz, DMSO-$d_6$) δ 7.87 (s, 2H), 7.82 (s, 1H), 7.56 (d, 1H), 6.99 (d, 1H), 6.77 (d, 1H), 4.51 (s, 0.67H), 4.44 (s, 1.33H), 3.42 (m, 2H), 3.14 (t, 2H), 3.00 (s, 1H), 2.86 (t, 2H), 2.78 (s, 2H), 1.94 (m, 2H), 1.71 (m, 2H), 1.59 (m, 2H).

EXAMPLE 153

A solution of 1.03 mol/g TFP resin (86 mg) diisopropylethylamine (46 µL), n-propylsulfonyl chloride (39 mg) in dichloromethane (3 mL) and DMA (2 mL) was stirred overnight and filtered. The filtrant was washed with DMA, THF and DMA, treated with a solution of EXAMPLE 89 (65 mg) and diisopropylethylamine (32 mg) in DMA (2 mL), stirred at 80° C. for 20 hours, cooled and filtered. The filtrate was resuspended in DMA (3 mL), agitated for 5 minutes and filtered and concentrated. The concentrate was purified by reverse-phase HPLC with 0.01M HCl/CH$_3$CN. $^1$H NMR (500 MHz, D$_2$O/DMSO-$d_6$) δ 7.94 (m, 3H), 7.91 (d, 1H), 7.39 (s, 1H), 4.35 (s, 2H), 3.18 (t, 2H), 2.80 (s, 3H), 1.73 (qt, 2H), 1.01 (t, 3H).

EXAMPLE 154

This compound was made by substituting benzylsulfonyl chloride for n-propylsulfonyl chloride in EXAMPLE 153. $^1$H NMR (500 MHz, D$_2$O/DMSO-$d_6$) δ 7.88 (s, 2H), 7.83 (s, 1H), 7.78 (d, 1H), 7.42 (m, 5H), 7.09 (d, 1H), 6.89 (s, 1H), 4.52 (s, 2H), 4.15 (s, 2H), 2.70 (s, 3H).

EXAMPLE 155

This compound was made by substituting 4-chlorobenzylsulfonyl chloride for n-propylsulfonyl chloride in EXAMPLE 153. $^1$H NMR (500 MHz, D$_2$O/DMSO-$d_6$) δ 7.89 (m, 4H), 7.80 (s, 1H), 7.47 (m, 3H), 7.11 (d, 1H), 6.99 (s, 1H), 4.55 (s, 2H), 4.18 (s, 2H), 2.73 (s, 3H).

EXAMPLE 156

This compound was made by substituting 3-fluorobenzenesulfonyl chloride for n-propylsulfonyl chloride in EXAMPLE 153. $^1$H NMR (500 MHz, D$_2$O/DMSO-$d_6$) δ 7.98 (s, 1H), 7.95 (m, 3H), 7.72 (d, 2H), 7.69 (dd, 1H), 7.67 (dd, 1H), 7.51 (s, 1H), 7.35 (d, 1H), 4.26 (s, 2H), 2.74 (s, 3H).

EXAMPLE 157

This compound was made by substituting 3-methoxybenzenesulfonyl chloride for n-propylsulfonyl chloride in EXAMPLE 153. $^1$H NMR (500 MHz, D$_2$O/DMSO-$d_6$) δ 7.94 (m, 4H), 7.85 (d, 1H), 7.61 (dd, 1H), 7.44 (d, 1H), 7.28 (m, 3H), 4.22 (s, 2H), 3.85 (s, 3H), 2.73 (s, 3H).

EXAMPLE 158

This compound was made by substituting 2-chlorobenzenesulfonyl chloride for n-propylsulfonyl chloride in EXAMPLE 153. $^1$H NMR (500 MHz, D$_2$O/DMSO-$d_6$) δ 8.03

(d, 1H), 7.95 (m, 3H), 7.86 (d, 1H), 7.71 (s, 1H), 7.69 (dd, 1H), 7.58 (dd, 1H), 7.36 (s, 1H), 7.30 (d, 1H), 4.51 (s, 2H), 2.88 (s, 3H).

EXAMPLE 159

This compound was made by substituting 4-n-propylbenzenesulfonyl chloride for n-propylsulfonyl chloride in EXAMPLE 153. $^1$H NMR (500 MHz, D$_2$O/DMSO-d$_6$) δ 7.93 (m, 4H), 7.84 (d, 1H), 7.73 (d, 2H), 7.49 (d, 2H), 7.24 (d, 1H), 4.19 (s, 2H), 2.72 (s, 3H), 2.65 (t, 2H), 1.61 (qt, 2H), 0.90 (t, 3H).

EXAMPLE 159

This compound was made by substituting 2-naphthylenesulfonyl chloride for n-propylsulfonyl chloride in EXAMPLE 153. $^1$H NMR (500 MHz, D$_2$O/DMSO-d$_6$) δ 8.47 (s, 1H), 8.17 (m, 2H), 8.06 (d, 1H), 7.95 (m, 3H), 7.86 (m, 2H), 7.71 (m, 2H), 7.37 (m, 2H), 4.30 (s, 2H), 2.80 (s, 3H).

EXAMPLE 160

This compound was made by substituting 4-trifluoromethoxybenzenesulfonyl chloride for n-propylsulfonyl chloride in EXAMPLE 153. $^1$H NMR (500 MHz, D$_2$O/DMSO-d$_6$) δ 7.98 (d, 1H), 7.94 (m, 4H), 7.91 (d, 1H), 7.62 (d, 2H), 7.29 (s, 1H), 7.28 (d, 1H), 4.25 (s, 2H), 2.76 (s, 3H).

EXAMPLE 161

This compound was made by substituting 5-methyl-1-phenyl-1H-pyrazole-4-sulfonyl chloride for n-propylsulfonyl chloride in EXAMPLE 153. $^1$H NMR (500 MHz, D$_2$O/DMSO-d$_6$) δ 8.05 (s, 1H), 7.94 (s, 2H), 7.91 (brs, 2H), 7.61 (m, 2H), 7.57 (m, 3H), 7.37 (brs, 1H), 7.34 (d, 1H), 4.26 (s, 2H), 2.78 (s, 3H), 2.49 (s, 3H).

The foregoing is meant to illustrate the invention but not to limit it. Variations and changes obvious to one skilled in the art are intended to be within the scope of the invention as defined in the claims.

We claim:
1. A compound selected from:
tert-butyl 4-(((5-chloro-3-(4-(2-chloro-5-(trifluoromethyl)phenyl)-5-cyano-6-oxo-1,6-dihydropyridin-2-yl)-2-hydroxybenzyl)(methyl)amino)carbonyl)-1-piperidinecarboxylate;
N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide;
1-acetyl-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-N,4-dimethyl-4-piperidinecarboxamide;
tert-butyl 4-(((5-chloro-3-(4-(2-chloro-5-(trifluoromethyl)phenyl)-5-cyano-6-oxo-1,6-dihydropyridin-2-yl)-2-hydroxybenzyl)(methyl)amino)carbonyl)-4-phenyl-1-piperidinecarboxylate;
N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-phenyl-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(4-pyridinyl)-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-1-(4-cyanophenyl)-N-methyl-4-piperidinecarboxamide;
1-(4-acetylphenyl)-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide;
1-acetyl-N-(5-chloro-3-(4-(2-chloro-5-(trifluoromethyl)phenyl)-5-cyano-6-oxo-1,6-dihydropyridin-2-yl)-2-hydroxybenzyl)-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-1-(methoxyacetyl)-N-methyl-4-piperidinecarboxamide;
1-butyryl-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(2-methylbutanoyl)-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(4,4,4-trifluorobutanoyl)-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(4,4,4-trifluorobutanoyl)-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(tetrahydro-2-furanylcarbonyl)-4-piperidinecarboxamide;
1-(3-butynoyl)-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(3-nitropropanoyl)-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-1-(cyclopropylcarbonyl)-N-methyl-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-1-(cyclopropylacetyl)-N-methyl-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-1-(cyclohexylcarbonyl)-N-methyl-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-propyl-4-piperidinecarboxamide;
N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(2-phenylethyl)-4-piperidinecarboxamide;

N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(2-(2,6,6-trimethyl-1-cyclohexen-1-yl)ethyl)-4-piperidinecarboxamide;

1-(2-(benzyloxy)ethyl)-N-(5-chloro-3-(4-(2-chloro-5-(trifluoromethyl)phenyl)-5-cyano-6-oxo-1,6-dihydropyridin-2-yl)-2-hydroxybenzyl)-N-methyl-4-piperidinecarboxamide;

N-(5-chloro-3-(4-(2-chloro-5-(trifluoromethyl)phenyl)-5-cyano-6-oxo-1,6-dihydropyridin-2-yl)-2-hydroxybenzyl)-N-methyl-1-(3-(5-methyl-2-furyl)butyl)-4-piperidinecarboxamide;

1-acetyl-N-((4'-chloro-5-(4-(2-chloro-5-(trifluoromethyl)phenyl)-5-cyano-6-oxo-1,6-dihydropyridin-2-yl)-4-hydroxy(1,1'-biphenyl)-3-yl)methyl)-N-methyl-4-piperidinecarboxamide;

1-acetyl-N-(3-(4-(2-chloro-5-(trifluoromethyl)phenyl)-5-cyano-6-oxo-1,6-dihydropyridin-2-yl)-5-cyclopentyl-2-hydroxybenzyl)-N-methyl-4-piperidinecarboxamide;

and therapeutically acceptable salt thereof.

\* \* \* \* \*

UNITED STATES PATENT AND TRADEMARK OFFICE
CERTIFICATE OF CORRECTION

PATENT NO.       : 7,910,742 B2
APPLICATION NO.  : 11/529845
DATED            : March 22, 2011
INVENTOR(S)      : Michael D. Wendt et al.

It is certified that error appears in the above-identified patent and that said Letters Patent is hereby corrected as shown below:

Column 59 part of Claim 1, Line 56 revise – "zyl)-N,4-dimethyl-4-piperidinecarboxamide;" to read as --zyl)-3-(4-morpholinyl)-N-propylpropanamide;--

Column 59 part of Claim 1 – Insert after Line 56 --N-(5-chloro-3-(4-(2-chloro-5-(trifluoromethyl)phenyl)-5-cyano-6-oxo-1,6-dihydropyridin-2-yl)-2-hydroxybenzyl)-N,4-dimethyl-4-piperidinecarboxamide;--

Signed and Sealed this
Eleventh Day of October, 2011

David J. Kappos
*Director of the United States Patent and Trademark Office*